US011260416B2

(12) United States Patent
Wilkerson et al.

(10) Patent No.: US 11,260,416 B2
(45) Date of Patent: Mar. 1, 2022

(54) EJECTOR DEVICES, METHODS, DRIVERS, AND CIRCUITS THEREFOR

(71) Applicant: Eyenovia, Inc., New York, NY (US)

(72) Inventors: Jonathan Ryan Wilkerson, Raleigh, NC (US); Iyam Lynch, Boone, NC (US); Jeffrey Parrott, Boone, NC (US); Charles Eric Hunter, Boone, NC (US)

(73) Assignee: Eyenovia, Inc., New York, NY (US)

( * ) Notice: Subject to any disclaimer, the term of this patent is extended or adjusted under 35 U.S.C. 154(b) by 13 days.

(21) Appl. No.: 16/434,428

(22) Filed: Jun. 7, 2019

(65) Prior Publication Data

US 2020/0094285 A1    Mar. 26, 2020

Related U.S. Application Data

(62) Division of application No. 15/397,795, filed on Jan. 4, 2017, now abandoned, which is a division of
(Continued)

(51) Int. Cl.
*B05B 17/06* (2006.01)
*H01L 41/04* (2006.01)
(Continued)

(52) U.S. Cl.
CPC ........ *B05B 17/0607* (2013.01); *A61F 9/0008* (2013.01); *A61M 11/005* (2013.01);
(Continued)

(58) Field of Classification Search
CPC ............ B05B 17/0607; B05B 17/0676; B05B 17/0646; A61F 9/0008; A61M 11/005;
(Continued)

(56) References Cited

U.S. PATENT DOCUMENTS 3,892,235 A   7/1975   Van Amerongen et al.
4,533,082 A   8/1985   Maehara et al.
(Continued)

FOREIGN PATENT DOCUMENTS

CA   1339281 C   8/1997
CA   2394664 A1   6/2000
(Continued)

OTHER PUBLICATIONS

Santvliet et al., "Determinants of Eye Drop Size," *Survey of Ophthalmology*, Mar.-Apr. 2004, vol. 49, pp. 197-211.
(Continued)

*Primary Examiner* — Qingzhang Zhou
*Assistant Examiner* — Joel Zhou
(74) *Attorney, Agent, or Firm* — Mintz Levin Cohn Ferris Glovsky and Popeo, P.C.

(57) ABSTRACT

In a piezoelectric ejector assembly, a piezoelectric actuator is attached to an ejector mechanism, while a drive signal generator and a controller are coupled to the actuator. The drive signal generator is configured to generate a drive signal for driving the actuator to oscillate the ejector assembly. The controller is configured to control the drive signal generator to drive the actuator at a resonant frequency of the ejector assembly, and an auto-tuning circuit is provided to define the optimum drive signal frequency.

8 Claims, 49 Drawing Sheets

Related U.S. Application Data application No. 13/895,055, filed on May 15, 2013, now Pat. No. 9,539,604.

(60) Provisional application No. 61/722,584, filed on Nov. 5, 2012, provisional application No. 61/722,556, filed on Nov. 5, 2012, provisional application No. 61/647,359, filed on May 15, 2012.

(51) Int. Cl.

| | |
|---|---|
| *H01L 41/09* | (2006.01) |
| *B41J 2/045* | (2006.01) |
| *B41J 2/14* | (2006.01) |
| *B05B 17/00* | (2006.01) |
| *G01H 13/00* | (2006.01) |
| *A61F 9/00* | (2006.01) |
| *A61M 11/00* | (2006.01) |

(52) U.S. Cl.
CPC ...... *B05B 17/0646* (2013.01); *B05B 17/0676* (2013.01); *B41J 2/0452* (2013.01); *B41J 2/04541* (2013.01); *B41J 2/04551* (2013.01); *B41J 2/04581* (2013.01); *B41J 2/14233* (2013.01); *G01H 13/00* (2013.01); *H01L 41/042* (2013.01); *H01L 41/0973* (2013.01); *B41J 2202/15* (2013.01)

(58) Field of Classification Search
CPC ..... G01H 13/00; B41J 2/0452; B41J 2/04541; B41J 2/04551; B41J 2/04581; B41J 2/14233; B41J 2202/15; H01L 41/042; H01L 41/0973

See application file for complete search history.

(56) References Cited

U.S. PATENT DOCUMENTS

| | | | |
|---|---|---|---|
| 5,024,355 A | 6/1991 | Jouillat et al. | |
| 5,130,598 A | 7/1992 | Verheyen | |
| 5,296,673 A | 3/1994 | Smith | |
| 5,359,350 A | 10/1994 | Nakano | |
| 5,406,503 A | 4/1995 | Williams, Jr. et al. | |
| 5,518,179 A | 5/1996 | Humberstone et al. | |
| 5,607,410 A | 3/1997 | Branch | |
| 5,630,793 A | 5/1997 | Rowe | |
| 5,984,448 A | 11/1999 | Yanagawa | |
| 6,011,062 A | 1/2000 | Schneider et al. | |
| 6,111,335 A * | 8/2000 | Acatrinei | G01R 29/22 310/316.03 |
| 6,530,370 B1 | 3/2003 | Heinonen | |
| 6,550,472 B2 | 4/2003 | Litherland et al. | |
| 6,921,020 B2 | 7/2005 | Ivri | |
| 6,976,639 B2 | 12/2005 | Williams et al. | |
| 7,367,334 B2 | 5/2008 | Faison, Jr. et al. | |
| 7,448,559 B2 | 11/2008 | Le Maner et al. | |
| 7,828,232 B2 | 11/2010 | Oomori et al. | |
| 7,883,031 B2 | 2/2011 | Collins, Jr. et al. | |
| 7,954,486 B2 | 6/2011 | Papania et al. | |
| 7,954,730 B2 | 6/2011 | Ng | |
| 8,012,136 B2 | 9/2011 | Collins, Jr. et al. | |
| 8,205,971 B2 | 6/2012 | Newton et al. | |
| 8,485,503 B2 | 7/2013 | Lei | |
| 8,545,463 B2 | 10/2013 | Collins, Jr. et al. | |
| 8,676,543 B2 * | 3/2014 | Wolf | G01D 15/00 702/190 |
| 8,684,980 B2 | 4/2014 | Hunter et al. | |
| 8,733,935 B2 | 5/2014 | Ballou, Jr. et al. | |
| 9,087,145 B2 | 7/2015 | Ballou, Jr. et al. | |
| 9,279,177 B2 | 3/2016 | Choi et al. | |
| 9,463,486 B2 | 10/2016 | Wilkerson et al. | |
| 10,639,194 B2 | 5/2020 | Hunter et al. | |
| 10,646,373 B2 | 5/2020 | Hunter et al. | |
| 2002/0085067 A1 | 7/2002 | Palifka et al. | |
| 2002/0196575 A1 | 12/2002 | Harmer | |
| 2003/0116642 A1 | 6/2003 | Williams et al. | |
| 2004/0039355 A1 | 2/2004 | Gonzalez et al. | |
| 2004/0163641 A1 | 8/2004 | Tyvoll et al. | |
| 2004/0215157 A1 | 10/2004 | Peclat et al. | |
| 2004/0256487 A1 | 12/2004 | Collins, Jr. et al. | |
| 2005/0121171 A1 | 6/2005 | Mukasa | |
| 2005/0200688 A1 | 9/2005 | Silverbrook | |
| 2005/0211797 A1 | 9/2005 | Abergel et al. | |
| 2005/0286346 A1 | 12/2005 | Croft | |
| 2006/0011737 A1 | 1/2006 | Amenos et al. | |
| 2006/0039715 A1 | 2/2006 | Rimai et al. | |
| 2006/0209129 A1 | 9/2006 | Onozawa | |
| 2006/0243820 A1 | 11/2006 | Ng | |
| 2007/0119968 A1 | 5/2007 | Collins et al. | |
| 2007/0211212 A1 | 9/2007 | Bennwik | |
| 2008/0011875 A1 | 1/2008 | Sipinski | |
| 2008/0043061 A1 | 2/2008 | Glezer et al. | |
| 2008/0169725 A1 | 7/2008 | Yu | |
| 2008/0237366 A1 | 10/2008 | Ehlert et al. | |
| 2008/0303850 A1 | 12/2008 | Shin et al. | |
| 2009/0035591 A1 | 2/2009 | Nishikawa et al. | |
| 2009/0108707 A1 | 4/2009 | Mahoney, III | |
| 2009/0114742 A1 | 5/2009 | Collins, Jr. | |
| 2009/0149829 A1 | 6/2009 | Collins, Jr. | |
| 2009/0167812 A1 | 7/2009 | Asai et al. | |
| 2009/0212133 A1 | 8/2009 | Collins, Jr. | |
| 2009/0272818 A1 | 11/2009 | Valpey et al. | |
| 2010/0066204 A1 | 3/2010 | Hayashi et al. | |
| 2010/0111843 A1 | 5/2010 | Boyden et al. | |
| 2010/0211408 A1 | 8/2010 | Park et al. | |
| 2010/0222752 A1 | 9/2010 | Collins, Jr. et al. | |
| 2010/0324852 A1 | 12/2010 | Wolf et al. | |
| 2011/0175971 A1 | 7/2011 | Newton et al. | |
| 2011/0233302 A1 | 9/2011 | Lin et al. | |
| 2011/0254901 A1 | 10/2011 | Sakai | |
| 2012/0062840 A1 | 3/2012 | Ballou, Jr. et al. | |
| 2012/0070467 A1 | 3/2012 | Ballou, Jr. et al. | |
| 2012/0111963 A1* | 5/2012 | Gordon | A61M 16/14 239/3 |
| 2012/0143152 A1 | 6/2012 | Hunter et al. | |
| 2013/0150812 A1 | 6/2013 | Hunter et al. | |
| 2013/0172830 A1 | 7/2013 | Hunter et al. | |
| 2013/0299607 A1 | 11/2013 | Wilkerson et al. | |
| 2013/0334335 A1 | 12/2013 | Wilkerson et al. | |
| 2014/0336618 A1 | 11/2014 | Wilkerson et al. | |
| 2014/0361095 A1 | 12/2014 | Haran | |
| 2016/0296367 A1 | 10/2016 | Ivri | |
| 2017/0136484 A1 | 5/2017 | Wilkerson et al. | |
| 2017/0151088 A1 | 6/2017 | Ballou, Jr. et al. | |
| 2017/0182510 A1 | 6/2017 | Wilkerson et al. | |
| 2019/0053945 A1 | 2/2019 | Hunter et al. | |
| 2020/0094285 A1 | 3/2020 | Wilkerson et al. | |
| 2020/0197218 A1 | 6/2020 | Newell et al. | |

FOREIGN PATENT DOCUMENTS

| | | |
|---|---|---|
| CA | 2458596 A1 | 3/2003 |
| CA | 2500252 A1 | 4/2004 |
| CA | 2709928 A1 | 7/2009 |
| CN | 1483225 A | 3/2004 |
| CN | 1854503 A | 11/2006 |
| CN | 101137446 A | 3/2008 |
| CN | 101274850 A | 10/2008 |
| CN | 101479046 A | 7/2009 |
| CN | 101843944 A | 9/2010 |
| CN | 101910608 A | 12/2010 |
| CN | 102180013 A | 9/2011 |
| EP | 0424685 | 5/1991 |
| EP | 0424686 | 5/1991 |
| EP | 1 219 314 B1 | 3/2004 |
| EP | 1865311 | 12/2007 |
| EP | 2 253 322 A1 | 11/2010 |
| FR | 2 934 128 A1 | 1/2010 |
| JP | S48018270 | 6/1973 |
| JP | S62-142110 A | 6/1987 |
| JP | H0712362 | 2/1995 |
| JP | H0712362 B2 | 2/1995 |
| JP | 2938176 B2 | 8/1999 |

(56) References Cited

FOREIGN PATENT DOCUMENTS

| JP | 2938179 | 8/1999 |
|---|---|---|
| JP | 2003516199 | 5/2006 |
| JP | 2008-515625 A | 5/2008 |
| JP | 2009056315 | 3/2009 |
| JP | 4294150 | 7/2009 |
| JP | 2012-508129 A | 4/2012 |
| WO | WO 93/15850 | 8/1993 |
| WO | WO 95/15822 | 6/1995 |
| WO | WO 98/08479 | 5/1998 |
| WO | WO 99/18901 | 4/1999 |
| WO | WO 2008/056435 | 5/2008 |
| WO | WO-2010/141118 A2 | 12/2010 |
| WO | WO 2011/009133 | 1/2011 |
| WO | WO-2011/058955 A1 | 5/2011 |
| WO | WO-2011/083379 A1 | 7/2011 |
| WO | WO-2011/142766 A1 | 11/2011 |
| WO | WO 2012/009696 | 1/2012 |
| WO | WO-2012/009702 A1 | 1/2012 |
| WO | WO 2012/009706 | 1/2012 |
| WO | WO 2012/119702 | 1/2012 |

OTHER PUBLICATIONS

Brown et al., "The Preservation of Ophthalmic Preparations," *Journal of the Society of Cosmetic Chemists*, 1965, vol. 16, pp. 369-393.
U.S. Appl. No. 13/882,962, filed May 1, 2013, US 2014-0336618.
U.S. Appl. No. 15/197,033, filed Jun. 29, 2016, US 2017-0136484.
U.S. Appl. No. 16/621,564, filed Dec. 11, 2019, US 2020-0197218.
U.S. Appl. No. 16/962,608, filed Jul. 16, 2020, US 2020-0337896.
U.S. Appl. No. 17/119,905, filed Dec. 11, 2020, US 2021-0177650.
PCT/US2020/020656, Mar. 2, 2020, WO 2020/180793 A1.
PCT/US2020/064648, Dec. 11, 2020, WO 2021/119513 A1.

* cited by examiner

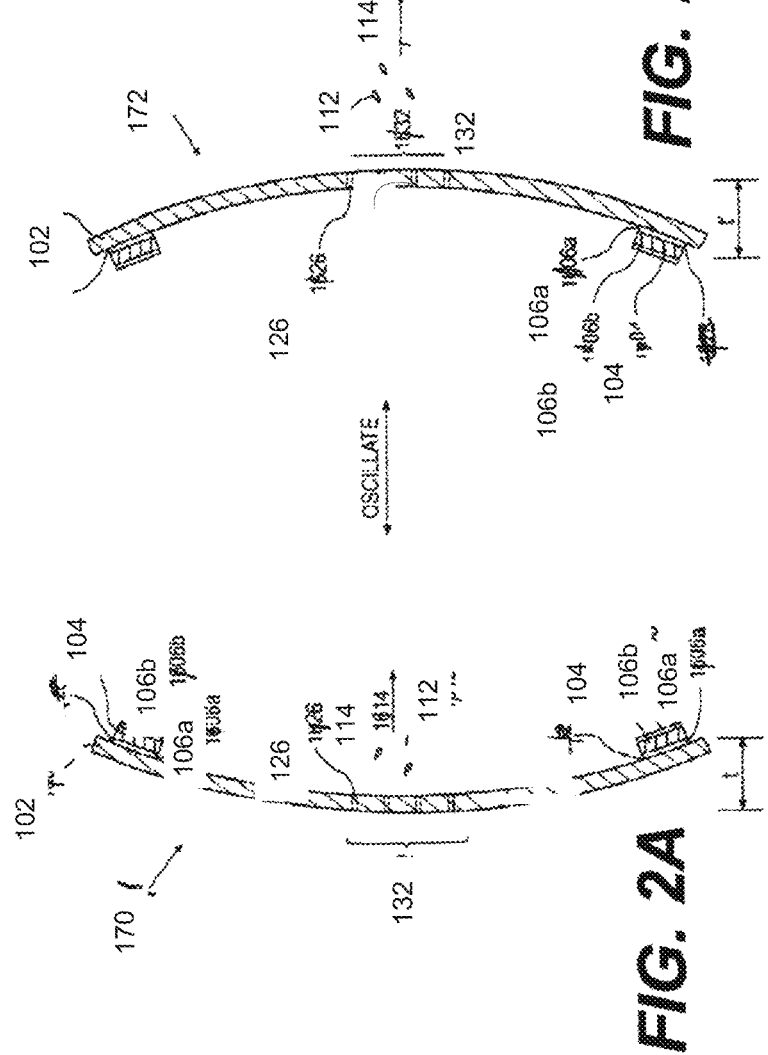

TIME SHIFT TO GET PHASE SHIFT

EJECTOR DEVICES, METHODS, DRIVERS, AND CIRCUITS THEREFOR

RELATED APPLICATIONS

This application is a division of U.S. patent application Ser. No. 15/397,795, filed Jan. 4, 2017, entitled "Ejector Devices, Methods, Drivers, and Circuits Therefor", now abandoned, which is a division of U.S. patent application Ser. No. 13/895,055, filed May 15, 2013, entitled "Ejector Devices, Methods, Drivers, and Circuits Therefor", now U.S. Pat. No. 9,539,604, which claims the benefit of the filing date of U.S. Application Nos. 61/647,359, filed May 15, 2012, entitled "Methods, Drivers and Circuits for Ejector Devices and Systems", 61/722,556, filed Nov. 5, 2012, entitled "Ejector Device and Resonance Function Driver Therefor", and 61/722,584, filed Nov. 5, 2012, entitled "On Demand Droplet Generation Device", the contents of which are herein incorporated by reference in their entireties.

FIELD OF THE DISCLOSURE

The systems, methods and apparatuses disclosed herein relate generally to the field of electromechanical systems. More specifically, the systems, methods and apparatuses described herein may be used to drive, monitor and control a droplet generation ejector system.

BACKGROUND OF THE DISCLOSURE

Piezoelectric actuators are electronic components that undergo mechanical distortion when voltage is applied across them. Under the influence of voltage, the crystalline structure of the piezoelectric material, e.g. ceramic, is affected such that the piezoelectric material will change shape. For example, if an alternating electric field is applied to a piezoelectric material, it will vibrate (contracting and expanding) at the frequency of the applied signal. This property of piezoelectric materials can be exploited to produce effective actuators—electronic components that can be used to displace a mechanical load. As voltage is applied to a piezoelectric actuator, the resulting change in the piezoelectric material's shape and size displaces the mechanical load. The electrical signals applied to a piezoelectric actuator are commonly either single-tone, i.e., single-frequency, or square-wave inputs.

In certain configurations, when a drive signal having sufficient voltage and appropriate frequency/frequencies is applied to a piezoelectric actuator, the piezoelectric actuator may induce movement in a mechanical load such as a fluid, generating droplets of the fluid, which may be ejected as a stream of droplets. During generation of an ejected stream of droplets, improved piezoelectric drivers, driver systems and methods of driving are generally desirable.

SUMMARY OF THE DISCLOSURE

The present disclosure is directed to a droplet ejector device and method of driving such a device. The droplet ejector device may comprise an actuator coupled to a droplet generator plate to define an ejector assembly, and driver and feedback circuits. The droplet generator plate may include a plurality of openings in fluid communication with a fluid reservoir, to be loaded with the fluid. The driver circuit is in signal communication with the actuator, and configured to drive the actuator based on a drive waveform. The feedback circuit is in signal communication with the actuator and the driver circuit, and is configured to determine a relaxation time based on a feedback signal indicative of oscillation of the fluid-loaded droplet generator plate. The drive waveform comprises a first drive sequence separated from a second drive sequence by a relaxation period based on the relaxation time of the fluid-loaded droplet generator plate and actuator.

Further, according to the disclosure there is provided a driver circuit and a drive signal or drive waveform for a piezoelectric ejector device or of a droplet generator that may be included in a piezoelectric device.

BRIEF DESCRIPTION OF THE DRAWINGS

FIGS. 2A and 2B are cross-sectional views of one embodiment of an activated ejector plate for an ejector assembly of the disclosure.

DETAILED DESCRIPTION

Figure 1:
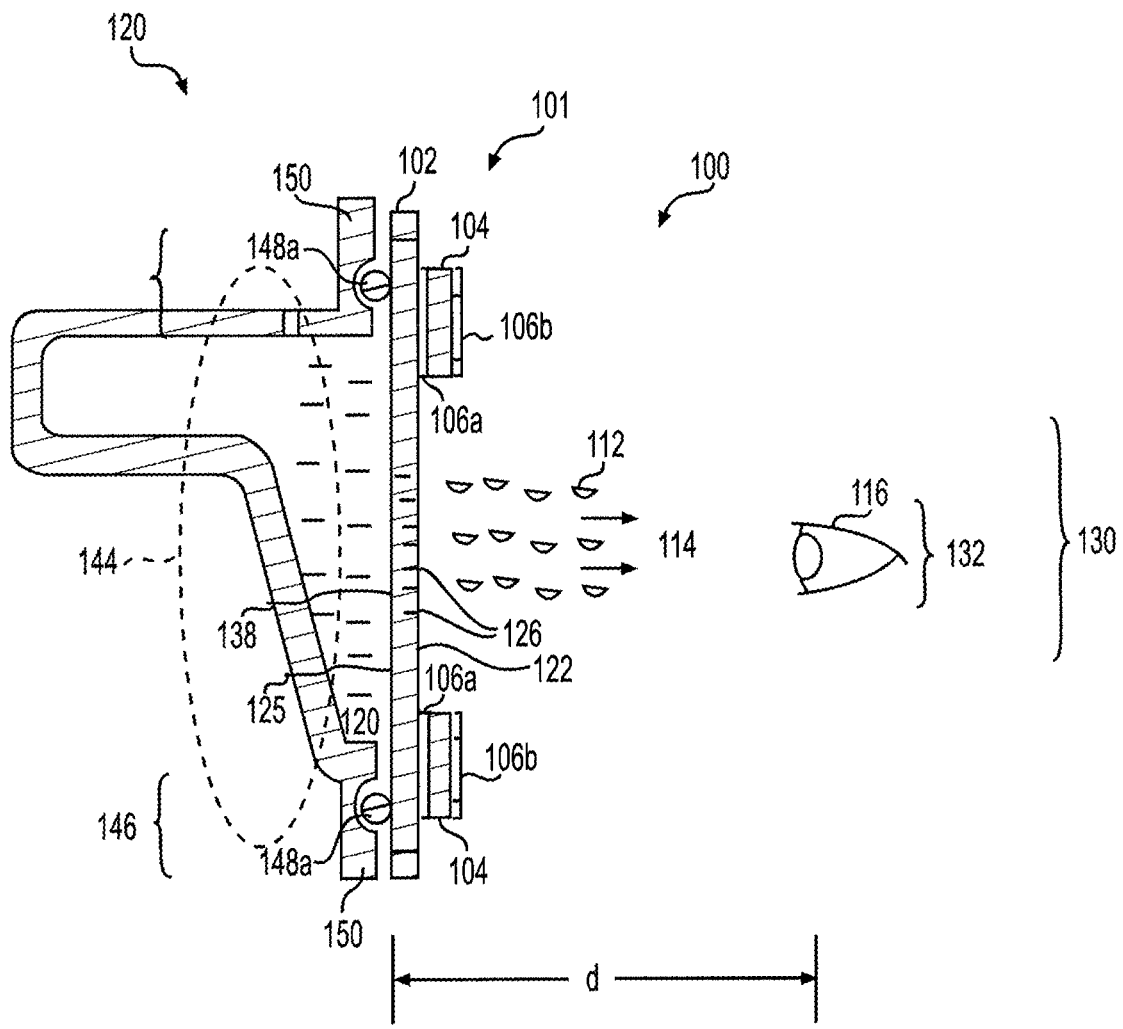
FIG. 1 shows a cross-sectional view of one embodiment of an ejector assembly of the disclosure.

The present disclosure generally relates to ejector devices, and methods for their use in the delivery of fluids. In particular, the present disclosure relates to ejector devices and methods useful in the delivery of fluids for ophthalmic, topical, oral, nasal, or pulmonary use, including the delivery of ophthalmic fluids to the eye. In droplet on demand operations, one or more fluid drops may be ejected at a given time, using the systems and method described herein to achieve the ejector displacements and velocities necessary to deliver the fluid in droplet form, with desired mass transfer rates and fluid dosages, and with reduced beading and ejector occlusion.

By way of background, in high volume droplet generation and ejector systems, fluid can bead on the surface of the ejector, occluding the droplet generating openings and reducing mass transfer, sometimes for periods of time up to several seconds or even minutes. Thus fluid beading and related effects may make it difficult to provide the necessary fluid ejection velocity over a pattern of ejector openings or nozzles. These challenges are particularly relevant when operating in low velocity modes, or unfavorable eigenmode shapes. Eigenmodes or normal modes of an oscillating system are patterns of vibration or motion in which all parts of the system move sinusoidally with the same frequency and with a fixed phase relation. The motion described by the normal modes are called resonance. The frequencies of the normal modes of a system are known as its natural frequencies or resonant frequencies. A physical object, such as a building, bridge or molecule or, as in this case, a fluid ejector mechanism, has a set of normal modes that depend on its structure, materials and boundary conditions. The ejected fluid may also form evaporative films on the ejector surface, which can substantially degrade ejector performance.

In certain embodiments, the ejector devices include an ejector mechanism (for instance an ejector plate and droplet generator plate coupled to an actuator), which generates a directed stream of droplets of fluid, and a fluid supply arrangement for loading the ejector mechanism. For ease of reference, the combination of the ejector mechanism and fluid supply arrangement will be referred to herein as an ejector assembly. Suitable fluids include, without limitation, solutions, suspensions and emulsions, which have viscosities in a range capable of droplet formation using an ejector mechanism. Suitable fluids also include, without limitation, fluids containing pharmaceutical and medicament products.

In order to achieve mass deposition of droplets of a fluid in high volume droplet generation and ejection systems, continuous fluid ejection via jetting may be utilized. Continuous jetting allows the mass deposition of larger volumes of fluid (for example, in the 0.5-30 uL range) by the generation and ejection of large numbers of small droplets.

However, ejecting a stream of droplets in continuous mode may result in beading due to chaotic jets, satellite droplet recapture, and inductive and triboelectric charging effects, among others. Once formed, a fluid bead located over an ejector opening may grow, e.g., as a result of pumping action, eventually wetting the exterior surface of the ejector openings, e.g., due to Coulomb attraction or mechanical motion. In addition to the momentum of the oscillating ejector mechanism, the fluid itself also adds to the momentum, which can build during continuous ejection mode, or when an insufficient relaxation period is provided between periods of oscillation and ejection, as is discussed below.

As such, according to the disclosure, improved droplet generation and ejection techniques are provided in order to drive the piezoelectric actuator (or other actuator) to reduce, minimize or eliminate fluid beading on the ejector surface, and over the ejector openings. The disclosure also provides improved droplet generation and ejection techniques which suppress or prevent the formation of films of incompletely ejected fluid on the surface of the ejection assembly, and on other components necessary to maintain performance over periods of extended use.

Different techniques of stopping or reducing fluid momentum build-up during continuous jet operation are disclosed, in order to suppress or prevent beading through electrical drive signal timing and piezoelectric energy cancellation or active damping. These techniques are applicable to a range of suitable drive signal types, including, but not limited to, sinusoidal, square, ramp, chirp, amplitude modulated and frequency modulated drive signals and waveforms, and combinations of such waveforms.

In embodiments of these techniques, droplets may be formed from fluid contained in a reservoir coupled to an ejector mechanism. The ejector mechanism and reservoir may be disposable or reusable, and the components may be packaged in a housing of an ejector device, such as those described in U.S. Provisional Application Nos. 61/569,739, 61/636,559, 61/636,565, 61/636,568, 61/642,838, 61/642,867, 61/643,150 and 61/584,060, and in U.S. patent application Ser. Nos. 13/184,446, 13/184,468 and 13/184,484, the contents of which are incorporated herein by reference.

Referring to FIG. 1, for example, the ejector assembly 100 may include an ejector mechanism 101 and reservoir 120. The ejector mechanism 101 may include an oscillating plate arrangement with ejector plate 102 integrally formed with a centrally located generator plate section that includes the ejector openings 126, as in this embodiment, or the ejector plate 102 may be coupled to a separate generator plate, which can be activated by the piezoelectric actuator 104 that forms part of the ejector mechanism. For convenience, both embodiments will be referred to as having a droplet generator 132. The actuator 104 vibrates or otherwise displaces the ejector plate 102 to deliver fluid 110 from a reservoir 120, either as a single droplet 112 (droplet on demand) from one or more openings 126, or as a stream of droplets 112 ejected from one or more openings 126, along a direction 114.

In some applications, ophthalmic fluid may be ejected toward an eye 116, for example of a human adult or child, or an animal. The fluid may contain a pharmaceutical agent to treat a discomfort, condition, or disease of the human or an animal, either in the eye or on skin surface, or in a nasal or pulmonary application.

The location of the attachment of the actuator 104 to the ejector plate 102 may also affect operation of ejector assembly 100, and the creation of single droplets or streams thereof. In the implementation of FIG. 1, for example, the actuator 104 (or a number of individual actuator components 104) may be coupled to a peripheral region of the ejector plate 102, on a surface 122 opposite the reservoir 120.

Central region 130 of the ejector plate 102, in this embodiment, includes an ejection region 132 with one or more openings 126, through which fluid 110 passes to form droplets 112. Ejection region (or droplet generator) 132 may occupy a portion of the central region 130, for example the center, or the ejection hole pattern of ejection region 132 may occupy substantially the entire area of central region 130. Further, the open end 138 of the reservoir may correspond substantially to the size of ejection region 132, or, as in this embodiment, the open region 138 may be larger than the ejection region 132.

As shown in FIG. 1, ejector plate 102 is disposed over or in fluid communication with the open end 138 of the reservoir 120, containing fluid 110. For example, the reservoir 120 can be coupled to the ejector plate 102 along a peripheral region 146 of the first major surface 125, using a suitable seal or coupling such as O-ring 148a arranged in a groove formed in the reservoir wall 150. A portion 144 of reservoir housing may also be provided in the form of a collapsible bladder. However, the disclosure is not so limited, and any suitable bladder or reservoir may be used.

When a voltage is applied across electrodes 106a and 106b on opposite surfaces 136 and 134 of the actuator 104, ejector plate 102 deflects to change to a relatively more concave shape 170 or a relatively more convex shape 172, as shown in FIGS. 2A and 2B, respectively depending on the polarity of the voltage.

When driven with an alternating voltage, the actuator 104 operates to alternatingly reverse the convex and concave shapes 170 and 172 of ejector plate 102, inducing periodic movement (oscillation) of ejector plate 102. Droplets 112 are formed at apertures or openings 126, as described above, with the oscillatory motion of ejection region 132 causing one or more droplets 112 to be ejected along fluid delivery (ejection) direction 114, for example in a single-droplet (droplet on demand) application, or as a stream of droplets.

The drive voltage and frequency may be selected for improved performance of the ejection mechanism, as described above. In some embodiments, the oscillation frequency of actuator 104 may be selected at or near a resonance frequency of the ejector plate 102, or at one or more frequencies selected to oscillate ejector plate 102 at such a resonance via superposition, interference, or resonant coupling.

When operated at or near resonant frequency, ejector plate 102 may amplify the displacement of ejector region (droplet generator) 132, decreasing the relative power requirements of the actuator, as compared to a direct-coupling design. The damping factor of the resonance system, including the actuator 104, ejector plate 102 and any fluid-filled droplet generator, may also be selected to be greater than the piezoelectric actuator input power, in order to reduce fatigue and increase service life without substantial failure.

Figure 3A:
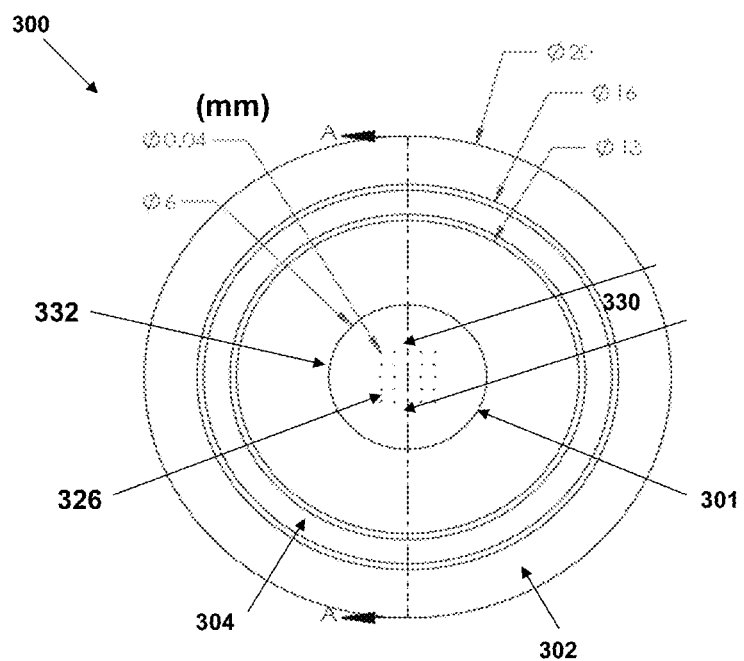
FIG. 3A is a schematic view of one embodiment of an ejector mechanism for an ejector assembly, of the disclosure in a symmetric configuration.

Examples of ejector assemblies are illustrated in U.S. Provisional Patent Application No. 61/569,739, "Ejector Mechanism, Ejector Device, and Methods of Use," filed Dec. 12, 2011, which is incorporated by reference herein. In one particular embodiment, ejector plate mechanism 100 may include a rotationally symmetric ejector plate 102 coupled to an annular actuator 104, for example as shown in FIG. 3A, and as described in U.S. Provisional Patent Application No. 61/636,565, "Centro-Symmetric Lead Free Ejector Mechanism, Ejector Device, and Methods of Use," filed Apr. 20, 2012, also incorporated by reference herein. However, the disclosure is not so limited.

In the particular configuration of FIG. 3A, the ejector mechanism 300 includes a separate generator plate 301 attached to an ejector plate 302. The actuator 304 incorporates one or more individual piezoelectric devices or other actuator elements, as described above, for driving the rotationally symmetric ejector plate 302, but in this embodiment comprises an annular structure. Drop generator (ejector) region 332 of ejector plate 302 includes a pattern of openings 326 in center region 330, and is driven via the actuator 304 by means of a suitable drive signal generator circuit as described below. Examples of techniques for generating drive voltages are illustrated in U.S. Provisional Patent Application No. 61/647,359, "Methods, Drivers and Circuits for Ejector Devices and Systems," filed May 15, 2012, as incorporated by reference herein.

Figure 3B:
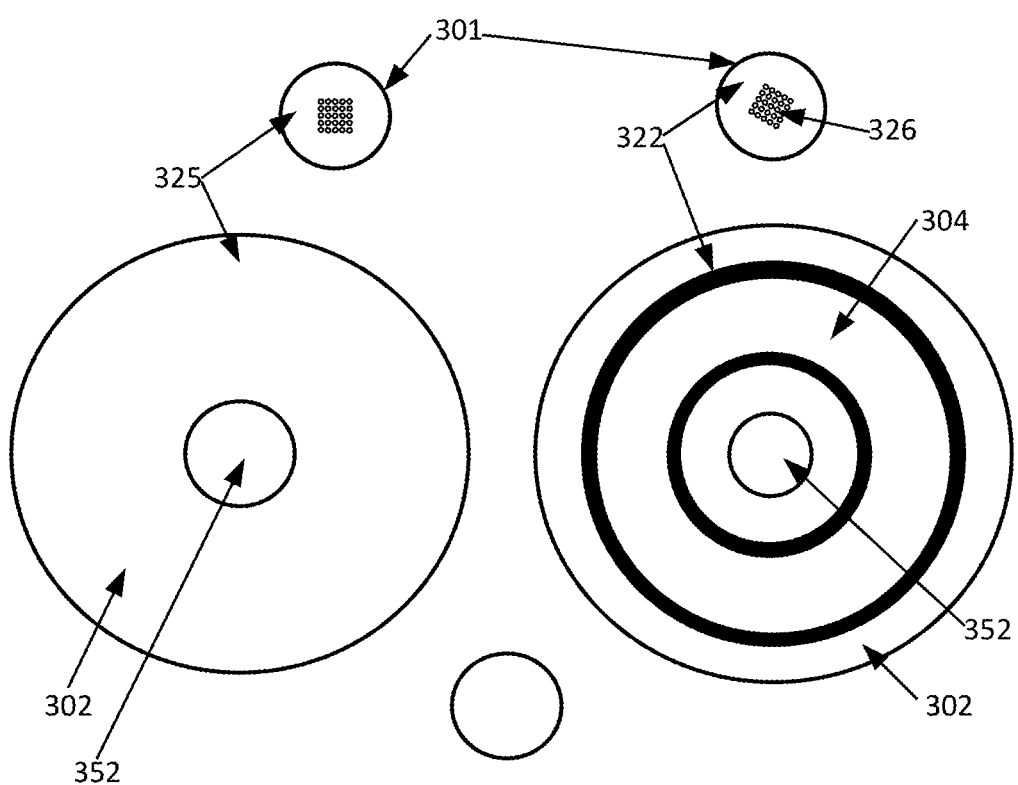
FIG. 3B is a dismantled view of an embodiment of a symmetric ejector mechanism of the disclosure.

FIG. 3B is a dismantled view of the symmetric ejector mechanism 300. In this embodiment, the ejector plate 302 utilizes a discrete (separate) drop generator element (ejector region) 301, as shown on the left and right of FIG. 3B from the back (face down) surface 325 and front (face up) surface 322, respectively. Drop generator element 301 is mechanically coupled to ejector plate 302 over central aperture 352, and includes a pattern of openings 326 configured to generate a stream of fluid droplets when driven by generator-plate type actuator 304, as described above.

Figure 3C:
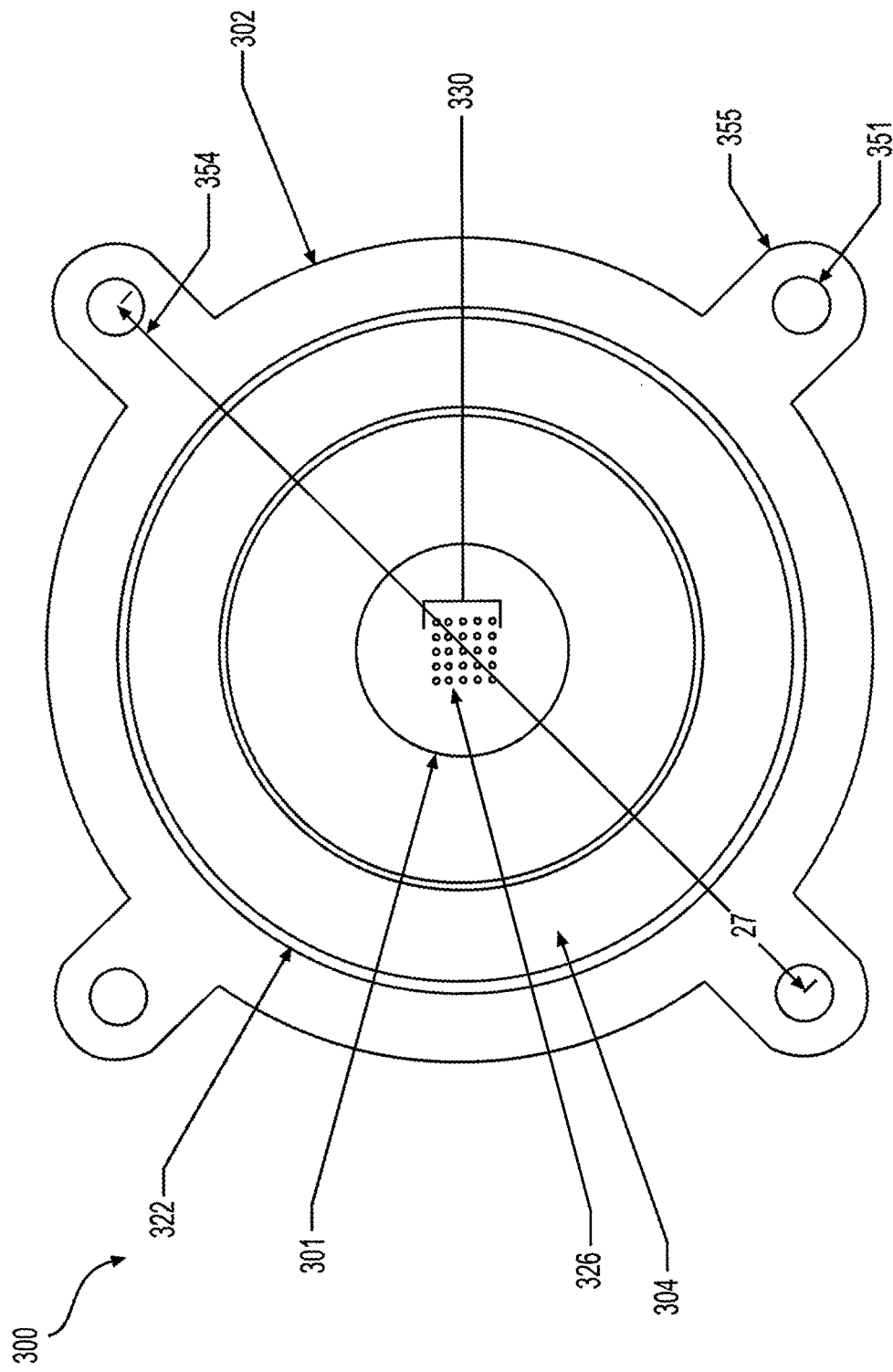
FIG. 3C is a plan view of an embodiment of a symmetric ejector mechanism of the disclosure.

FIG. 3C is a plan view of a symmetric ejector mechanism 300. Ejector mechanism 300 includes ejector plate 302, to which is attached actuator 304 and droplet generator 301. The droplet generator includes a pattern of openings 326 in central region 330, as described above. The ejector mechanism 300 may be coupled to a fluid reservoir or other ejection device component via apertures 351 in symmetrically arranged tab-type mechanical coupling elements 355, or using another suitable connection as described above with respect to FIG. 1.

As shown in FIG. 3C, the ejector plate 302 may have a dimension 354 of about 21 mm, or in a range of about 10 mm or less to about 25 mm or more, depending upon application. Suitable materials for ejector plate 302 and drop generator 301 include, but are not limited to, flexible stress and fatigue-resistant metals such as stainless steel.

For orientation purposes, the different elements of ejector mechanism 300 as shown in FIGS. 3A-3C may be described relative to the location of the reservoir such as reservoir 320 described above with respect to FIG. 1. In general, the proximal elements of mechanism 300 are located closer to fluid reservoir 120 (FIG. 1) and the distal elements are located farther from fluid reservoir 120, as defined along the droplet stream or ejection direction 114.

Figure 4:
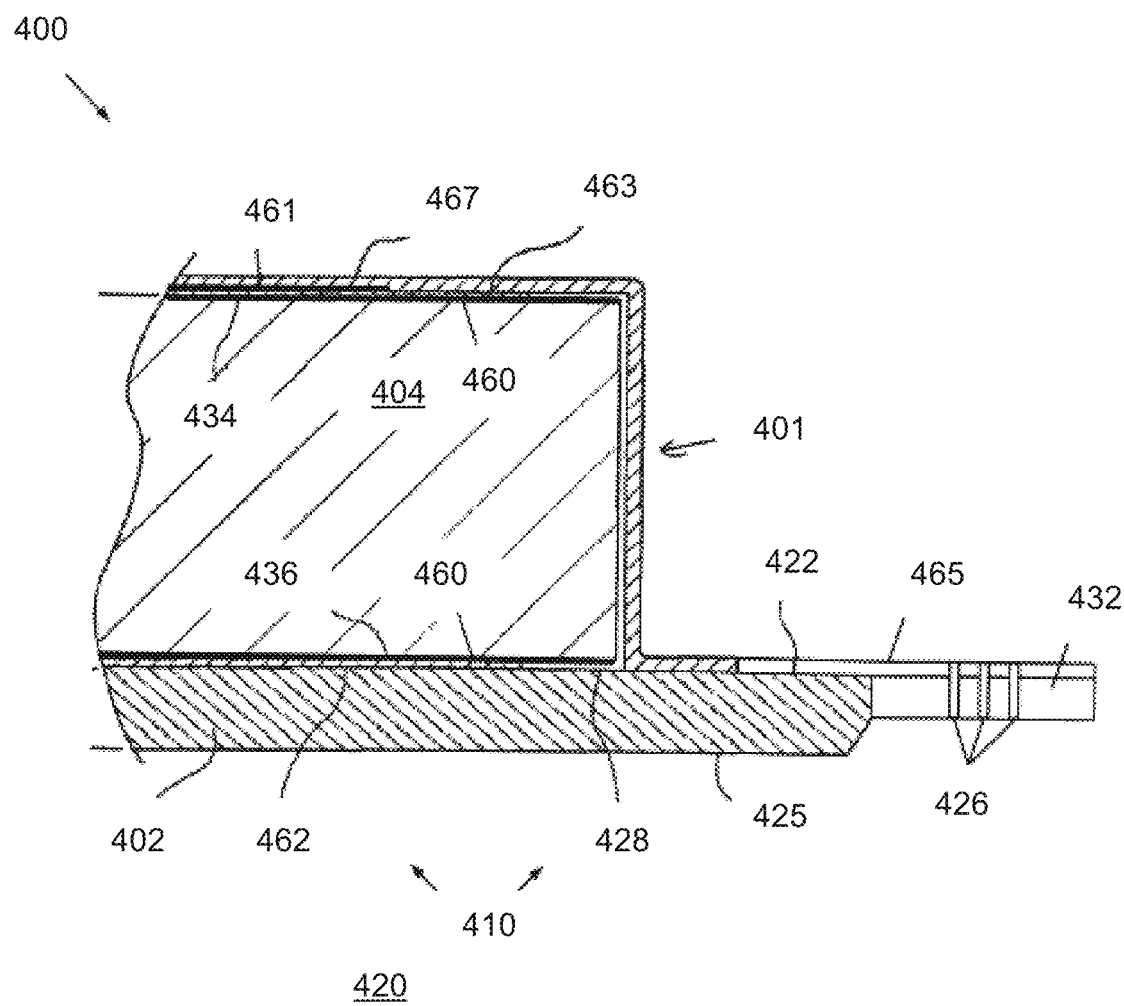
FIG. 4 is a cross-sectional view through part of an embodiment of an ejector mechanism of the disclosure.

In the particular embodiment of FIG. 4, the ejector assembly 400 includes an ejector mechanism 400 that comprises oscillating ejector plate 402 with first major (proximal) surface 425 adjacent fluid reservoir 420, and second major (distal) surface 422 opposite fluid reservoir 420. Piezoelectric actuator 404, in this embodiment, is formed as a distal element, with reservoir 420 attached to the proximal surface 425 of oscillating plate 402. Alternatively, actuator 404 may be coupled to ejector plate 402 on the distal surface 425 around the reservoir 420.

Proximal and distal surfaces 436 and 434 of actuator 404 are provided with conducting layers 460, for example to provide bottom and top electrodes 106a and 106b (FIG. 1) for drive signals, as described above. As shown in FIG. 4, conducting layer 460 on proximal surface 436 of actuator 404 is separated from distal surface or side 422 of ejector plate 402 by a dielectric layer 462, allowing the oscillating ejector plate 402 to be grounded and electrically isolated from conducting layer 460 of actuator 404. On the distal side 434 of the actuator, an additional dielectric layer 462 may be provided to space a metallization layer 461 from the top conducting layer (or drive electrode) 460. This electrically isolates metallization layer 461 allowing the metallization layer to serve as an electrically isolated electrode for back EMF (electromotive force) measurements in certain embodiments of the disclosure. In other embodiments separate contacts for back EMF measurements may be eliminated by using the voltage levels on the electrodes 106a, 106b as is discussed further below.

As shown in FIG. 4, oscillating ejector plate 402 is positioned in fluid communication with reservoir 420, and proximal surface or side 425 is in contact with fluid 410. An additional coating layer 463 may be formed over the exposed (top and side) surfaces of actuator 404, and may include at least part of distal surface 422 of ejector plate 402, in order to prevent contact between the actuator 404 and any fluid 410 ejected from reservoir 420. In some implementations, one or both of ejector plate 402 and generator plate (or ejector region) 432 may also be coated with an inert, medical grade, non-toxic, non-reactive, and optionally acid-, base-, and solvent-resistant material 465, or another material having a suitable combination of such properties.

Coatings 463 and 465 may be the same or different, and applied individually or in any combination, for example by sputtering, vapor deposition, physical vapor deposition (PAD), chemical vapor deposition (COD), electrostatic powder deposition, or any suitable combination of such techniques. Coatings 463 and 465 may include polymer materials such as polypropylene, nylon, and high density polyethylene (HDPE), TEFLON® material and other conformal coatings, and metal coating materials including, but not limited to, gold, platinum, and palladium. Coatings 463 and 465 may be selected to adhere sufficiently to prevent delamination when vibrating at a high frequency, as applied to any combination of surfaces of oscillating ejector plate 402, generator plate 432 and actuator 404, either individually or together, in a thickness range of about 0.1 µm or less to about 500 µm or more.

In order to drive the actuator of the piezoelectric mechanism, a drive signal or drive waveform needs to be generated by a driver circuit. In providing such a drive signal, a number of factors were considered in accordance with the present disclosure. In particular, a variety of factors can affect the velocity of the displaced mechanical load, including the drive signal frequency and amplitude as well as the quality factor of the mechanical resonance at said frequency. As the drive signal frequency, amplitude, or both are increased, the displacement velocity of the mechanical load increases. However, higher operating frequencies, while increasing displacement velocity, also have a higher average power. The additional power required to operate at high frequencies may not be desirable in certain applications. Piezoelectric materials and piezoelectric driven devices exhibit resonance regions where mechanical actuation becomes maximized. It is often desirable to provide an electrical actuation signal at these frequencies to cause maximum displacement of the piezoelectric element or piezoelectric mechanism (e.g., the piezoelectric element coupled to a load such as an ejector plate and fluid filled generator plate) using the least amount of electrical energy possible. However, at resonance, piezoelectric devices become either fully or partially resistive, dissipating a large amount of energy in the piezoelectric. They also lose the beneficial energy dissipation properties of capacitive mode operation and reduce their efficiency in resonant converter circuits. Thus, there remains a need for improved apparatuses, methods and systems, as described herein, which provide maximum displacement and displacement velocity of mechanical loads coupled to piezoelectric actuators, while simultaneously enhancing the energy efficiency of the system. This is particularly important in battery operated systems in which the available power may be limited. According to the invention, the fluid filled ejector mechanism is treated as a membrane with a membrane mode of vibration different from the piezo itself. While resonance of the piezo is the frequency with the highest movement/mechanical drive power of the ceramic itself, there are membrane modes which are not based on the ceramic/piezo resonance itself. The piezo simply generates the forcing function, and the lower the loss in the membrane the higher the movement. When the system is driven in one of these membrane modes the piezo can be nearly a perfect capacitor allowing high Q amplification of an input voltage or current with the piezo as the capacitor. This greatly reduces energy consumption and allows delivery of a much higher voltage and current to the device, without heating the piezoelectric.

In addition, a variety of factors can change the resonant properties and electrical characteristics of piezoelectric devices, such as the drive signal applied to the piezoelectric, the mechanical load coupled to the piezoelectric, or even the ambient temperature, pressure and humidity surrounding the piezoelectric. A piezoelectric originally driven to operate at a resonant frequency may drift out of resonance because of one or more of these factors, which cause less efficient operation of the piezoelectric, and potentially reduced displacement of the mechanical load. Thus, there remains a need for apparatuses, methods and systems, as described herein, which can detect the resonances of electromechanical systems comprising piezoelectric actuators and their associated mechanical loads, and when these systems are no longer operating in a resonance mode, to provide corrective action to bring the piezoelectric actuator and/or the mechanical load back into resonance.

According to the present disclosure, there is provided a method and circuit to track maximum displacement, or resonant modes, in order to compensate for temperature, humidity, and pressure variations, and manufacturing tolerances. Furthermore, tracking of resonances without the use of an isolated feedback electrode is described herein, using the actuator electrodes as part of the feedback portion of the resonant system. By eliminating the separate isolated feedback electrodes spray is appreciably increased by 10-50% depending on the device. In one embodiment, this technique is used with a full bridge circuit and a Q factor sweep with resonant converter circuits as is discussed in greater detail below.

In certain embodiments of the disclosure, means are provided for exciting, detecting, and characterizing an electrical and/or mechanical resonance of a piezoelectric element or several coupled elements, or of an ejector mechanism. When an electromechanical mechanism such as an ejector mechanism becomes resonant, energy is stored in the electromechanical mechanism and released at a different rate than in a non-resonant electromechanical, electrical, or mechanical mechanism. Furthermore, the resonance of the electromechanical mechanism will act as an integrator of electrical signals in time, allowing a number of unique signatures to be generated depending on the electrical signal applied.

In certain embodiments, an electrical signal, which could be a single tone, multi-tone, chirp, arbitrary waveform, or any electrical signal containing one or more frequencies is applied to a piezoelectric element. The circuit generating the electrical signal can be any circuit that delivers electrical power, or voltage and current, at the intended electrical signal frequency(s). The electrical signal is applied for a defined amount of time and then stopped suddenly. The electrical signal remaining in the piezoelectric is then measured by either current, voltage, or power measurement and either recorded for mathematical processing such as by way of an FFT (Fourier Transform) or applied directly to an analog energy integration circuit. The analog integrator can be switched on and off to correlate against a defined waveform or can simply integrate all energy stored in the ejector. Signatures of the electromechanical resonance are obtained which are dependent on the original electrical signal and the mechanical and electrical properties of the electromechanical system. [00106] Furthermore, and particularly with respect to droplet ejector systems, in order to generate droplets of the appropriate size and having sufficient ejection velocity, the drive signal to the piezoelectric must be sizeable. Batteries, which could be conveniently attached to a droplet generator ejection system, do not produce sufficient voltage to drive the piezoelectric. Thus, there remains a need for systems, methods and apparatuses for powering droplet generation ejection systems while maintaining the ease and portability of battery packs.

Figure 5:
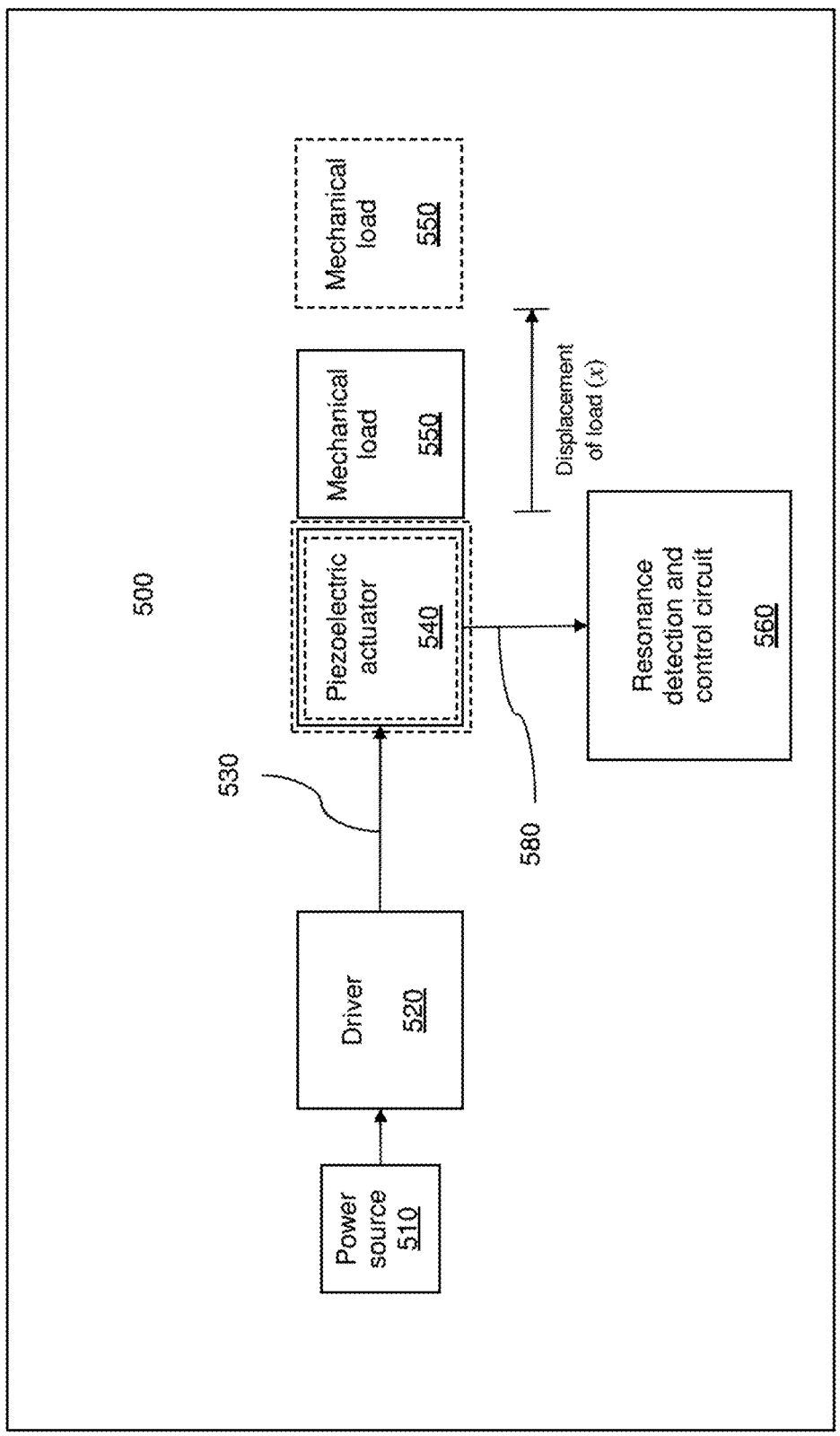
FIG. 5 is a block diagram of one embodiment of a system for driving and controlling a piezoelectric actuator according to the present disclosure.

FIG. 5 shows one embodiment of a system 500 for use of a piezoelectric actuator 540, e.g., as might be used in a droplet generator system. As shown on FIG. 5, the system 500 may comprise a power source 510, such as a battery; an electronic driver 520, i.e., the circuitry responsible for generating the drive voltage or signal 530 to a piezoelectric actuator 540; the piezoelectric actuator 540; and the mechanical load 550 to which the piezoelectric actuator 540 is coupled. The piezoelectric actuator 540 may be used to drive a variety of mechanical loads 550, such as a droplet generator plate to form fluid droplets as described in U.S. Provisional Application Nos. 61/569,739, 61/636,559, 61/636,565, 61/636,568, 61/642,838, 61/642,867, 61/643,150 and 61/584,060, and in U.S. patent application Ser. Nos. 13/184,446, 13/184,468 and 13/184,484, the contents of which are incorporated herein by reference, and as described above.

In certain embodiments, as shown on FIG. 5, it may also be desirable to couple a resonance detection and control circuit 560 to the piezoelectric actuator 540. This circuit 560 can be used to detect when the entire electromechanical mechanism 570 (actuator 540 and load 550) is no longer operating in a resonance mode, i.e., the mode in which the mechanism 570 produces the greatest or increased mechanical displacement of the load 550. The circuit 560 may also provide feedback to the driver 520 to control the frequency, for instance to bring it back to resonant frequency. Other embodiments of power sources, drivers, converters and waveforms in accordance with the disclosure are presented in the incorporated references.

As is discussed in further detail below, in one embodiment, a full bridge circuit is used to drive the piezoelectric ejector mechanism. The potential (voltage) on each side of the piezoelectric element is alternated between the power supply voltage, which may be the output of a boost converter, resonant converter, buck-boost converter, transformer, or voltage converter, and ground to allow portable operation at a given frequency. By driving the piezoelectric for as little as a cycle at a single frequency, energy is stored in the piezoelectric ejector mechanism which is released back into the circuit in the form of a voltage if the drive signal is stopped.

Thus, when the drive signal is halted, the piezoelectric operates dominantly as a signal source rather than a load. The energy of the electromechanical mechanism (ejector mechanism with its piezoelectric element) must go either back into the electrical circuitry as a voltage or be dissipated through friction and electrical loss in the mechanical system.

Three cases exist which determine how the electromechanical energy is removed and or dissipated. If the circuit attached to the ejector is open (tri-stated), the piezoelectric will trade energy through oscillation with driver FET capacitances or simply dissipate through mechanical loss and internal electrical loss. The circuit connected to the ejector could also be shorted, which causes the ejector to quickly dump its energy into the system ground. Instead, the circuit could present a finite electrical load to the ejector, which causes a controlled evanescent oscillation.

In the open and finite load cases, sampling the output voltage of the ejector provides a measure of the ejector mechanism movement, which is correlated to fluid ejection. Current sampling can be used in the case of a short to provide movement tracking. No feedback electrode is required in any of these cases, thereby avoiding having to provide a separate metallization layer such as the layer 461 in the FIG. 4 embodiment.

Power source 510 may be any suitable power source, including a suitable battery, capable of powering the driver 520. Although not shown, system 500 may include more than one power source, or an alternative, or back-up, power source, if desired. Depending on the characteristics of the power source 510, it may be necessary to boost the output voltage of the power source 510 in order to ultimately power the piezoelectric actuator 540.

Figure 6:
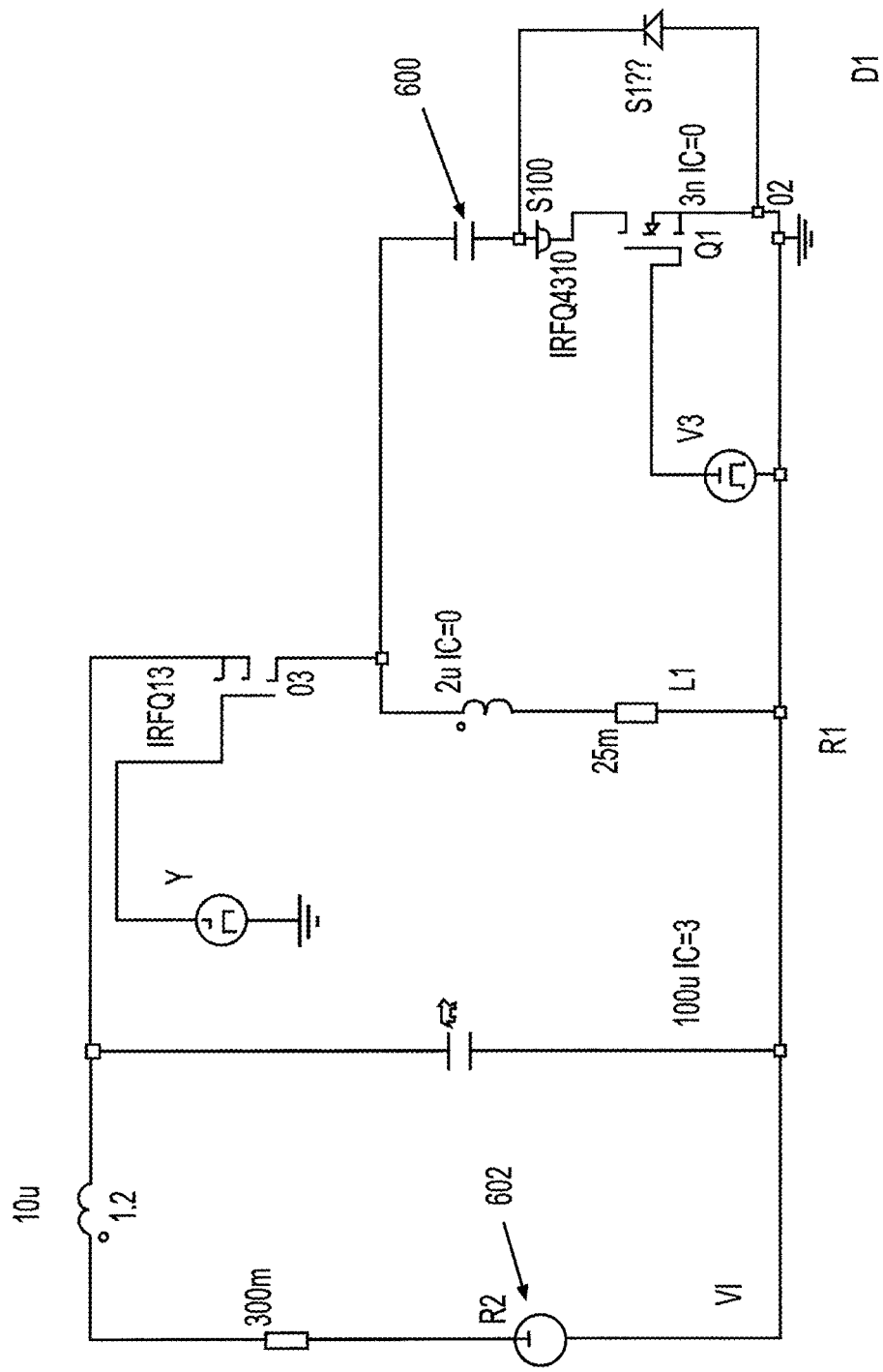
FIG. 6 is a schematic circuit diagram of a modified buck-boost converter of the disclosure.

As discussed above, in some embodiments according to the present disclosure, the output voltage from power source 510 may be boosted, e.g., by a boost converter or a buck-boost converter with a piezoelectric actuator 540 as a load. One embodiment of a modified buck-boost converter of the disclosure is shown in FIG. 6.

This converts DC-AC rather than DC-DC. It serves to dump charge onto a capacitor (defined by the piezoelectric actuator 600) then takes all that charge and funnels it back into the battery 602. Fast recovery diodes D1, D3 may be included to prevent body diode failure. The driver may include a P-MOSFET T1 connected in series with an inductor L1 from power input to ground, a piezoelectric connected between the series connection of the inductor L1 and P-MOS T1 and an N-MOS T2 connected to ground. The N-MOS T2 should have a fast recovery diode D1 to prevent body-diode failure. When the P-MOSFET T1 switches off, current continues to flow through the inductor L1 so output voltage above the N-MOSFET T2 drops negative and current conducts through the diode D1 in parallel with the N-MOSFET. All of the current deposits onto the piezoelectric and the voltage over the piezoelectric goes from zero to a value determined by the current ramping through the inductor L1. The voltage may be calculated based on the charge contained by the current in the inductor L1 according to the equation: $V=Q/C$, where Q is the charge and C is the capacitance (V is voltage). In one embodiment, at the end of the cycle, the N-MOSFET D2 may be switched on to take the piezoelectric voltage back to ground. This cycle may be repeated at the intended drive frequency. The circuit with its buck-boost converter may be more efficient (50% less current use or better) as compared to boost converters while producing an equivalent voltage. This takes substantially less current for the same drive voltage. However, a drawback with the use of this configuration is that it is limited to about an 80-100 Volt amplitude signal due to the drain to source voltage Vds limits of the FETs.

Figure 7:
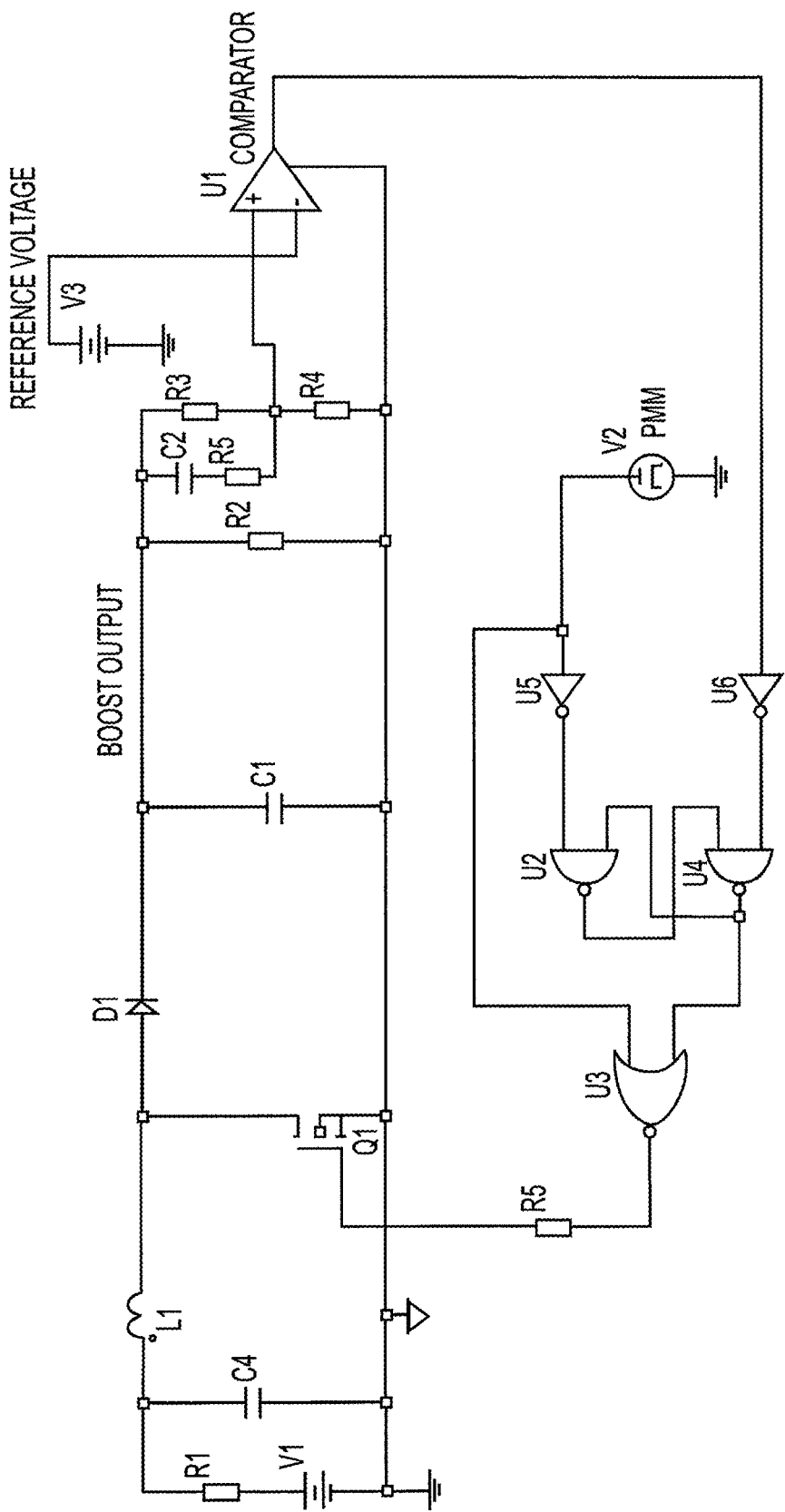
FIG. 7 is a schematic circuit diagram of one embodiment of a modified boost converter of the disclosure used to convert battery voltages from 2 to 3 volts up to as high as 60 V output to drive a full bridge and/or a resonant converter.
Figure 8:
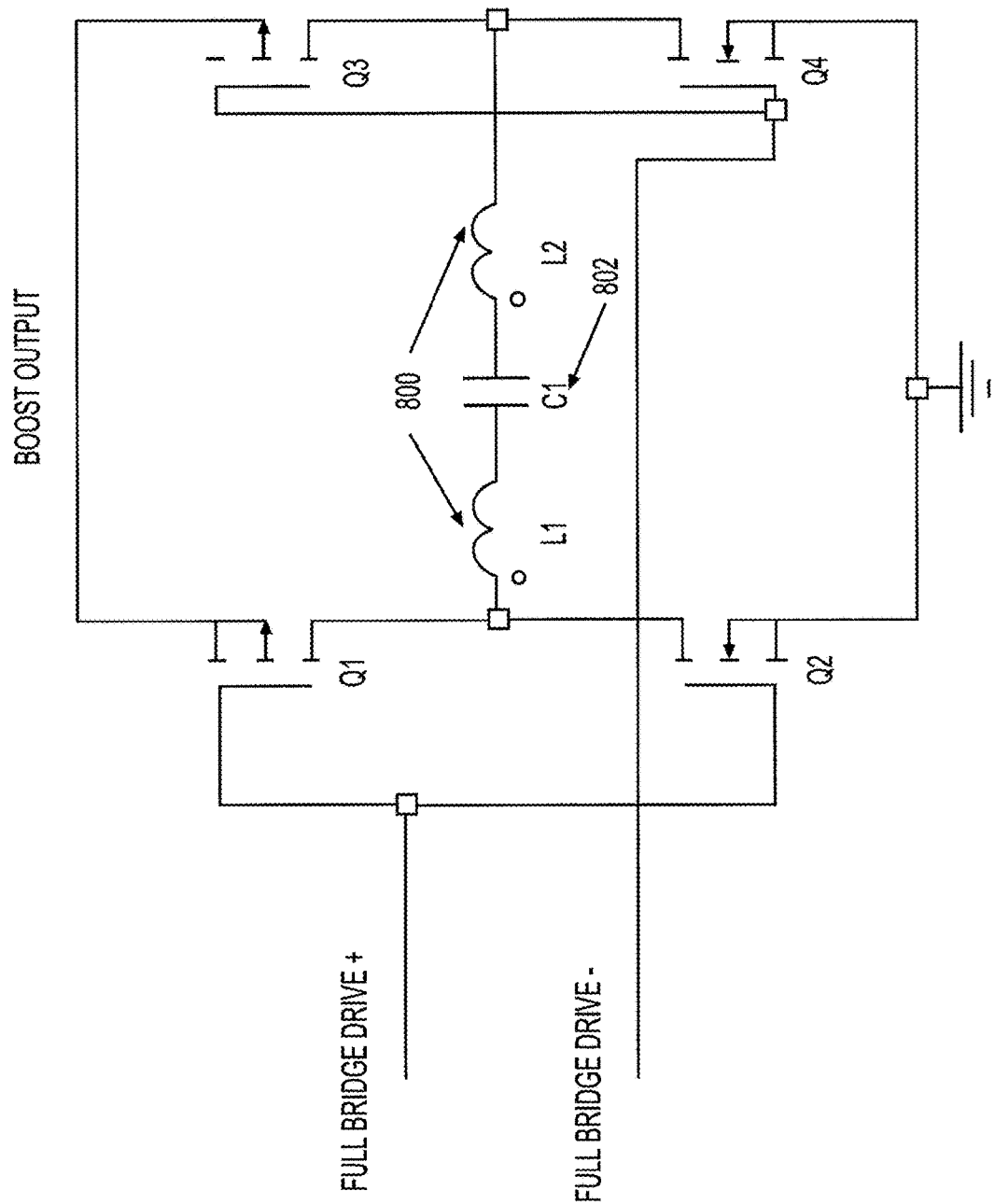
FIG. 8 is a schematic circuit diagram of one embodiment of a driving a resonant converter of the disclosure.

In another embodiment a modified boost converter (shown in FIG. 7) used with a full bridge (discussed further below with respect to FIG. 15) and driving a resonant converter (shown in FIG. 8) was used to increase signal amplitude and provide desired overshoot capabilities (i.e., 100-170 Volts). The embodiment of a resonant converter shown in FIG. 8 includes one or more inductors 800. The inductors are added to create a resonant converter for increased voltage amplification over the piezoelectric actuator (depicted by the capacitor 802), which functions as the load. Thus in this embodiment a full bridge is used to drive a resonant tank, which functions as a resonant converter without the final DC portion in a DC-AC-DC transition.

Figure 9:
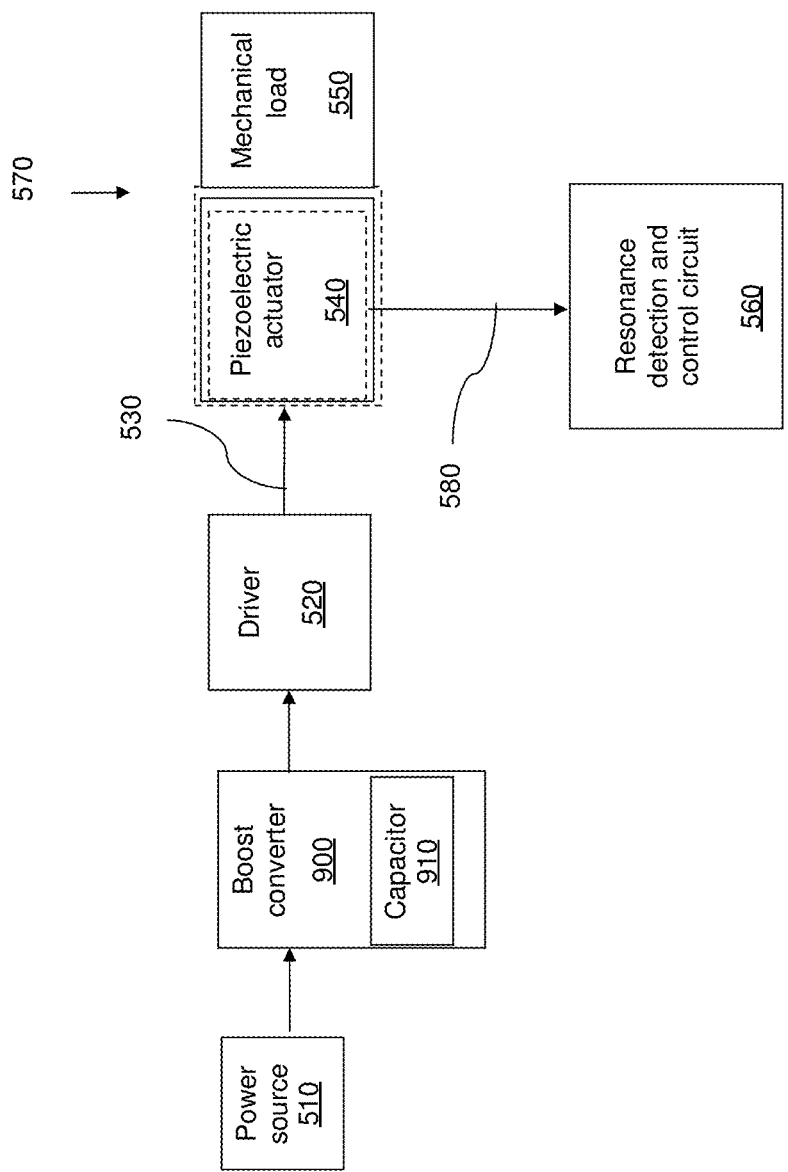
FIG. 9 is a block diagram of one embodiment of a driver of the disclosure making use of a boost converter.

One embodiment of a driver circuit making use of a boost converter is shown in FIG. 9. Like elements will be referred to using the same reference numerals in the various embodiments discussed below. As shown in the embodiment of FIG. 9, the power source 510 may be coupled to a boost converter 900, which, in turn, includes or is coupled to a charge-holding capacitor 910. The boost converter 900 may be used to step up the supply voltage from the power source 510 and to charge the capacitor 910 in order to supply the charge and voltage necessary to drive the piezoelectric actuator 540. The boost converter 900 changes voltage to allow the correct E-field to be applied to piezoelectric actuator 540, thus, voltage rather than power may be boosted. By way of non-limiting example, a power supply 510 may supply 2.7 V to the boost converter 900, providing a capacitor 910 output voltage of up to 60 V. Other embodiments of power sources in accordance with the disclosure are presented herein. A feedback signal 580 is used by a resonance detection and control circuit 560 to determine resonance frequencies and optionally to provide feedback to control the frequencies provided by the driver 520.

Driver 520 according to the present disclosure may generally be configured to produce and control the drive signal 530 to the piezoelectric actuator 540. Additional embodiments of drivers 520 according to the present disclosure are discussed below. Depending on the desired characteristics of the overall mechanism 570, the driver 520 may be operated in any of several different modes. For example, in certain embodiments, drivers 520 as described herein may be configured to create multi-tone drive signals 530 which operate (1) at two or more frequencies outside mechanical/electrical resonances where the beat frequencies are at mechanical resonances, as described in further detail below in the section titled "Envelope Mode", or (2) at two or more frequencies of separate mechanical resonances, as described in further detail below in the section entitled "Bessel Mode". It will, of course, be understood that these drivers may also be configured to drive a single frequency, such as a single resonant frequency. The drivers may also provide square waves to drive a single mode or multiple modes with square wave harmonics to induce increased mechanism velocity. Specific implementations are now discussed.

In one embodiment, it may be desirable to drive the piezoelectric actuator 540 so as to increase the displacement of the mechanical load 550, while simultaneously preserving the capacitive effect of the piezoelectric actuator 540 and minimizing overall power consumption. In one embodiment, a driver may operate in an "envelope mode". In such an embodiment, the driver 520 may be configured so as to operate at two or more frequencies outside mechanical/electrical resonances where the beat frequencies are at mechanical resonances.

As described previously, in certain implementations, piezoelectric actuators may be driven in resonance to provide maximum displacement of the mechanical load. Thus, the drive signal 530 may be based on integer multiples of a resonant frequency, i.e., the piezoelectric actuator 540 may be driven harmonically. However, without being limited by theory, it will be understood by those skilled in the art that signals having higher fundamental operating frequencies may result in increased electrical power consumption, since as the impedance of the load changes with frequency, certain higher operating frequencies may have the effect that the piezoelectric actuator behaves more like a resistor than a capacitor. In certain embodiments of the disclosure, the driver 520 may alternatively combine two or more signals to drive the piezoelectric actuator 540. The frequencies and amplitudes of the input signals may be selected so as to produce increased displacement of the mechanical load, while simultaneously preserving beneficial energy and circuit benefits, such as nearly ideal capacitive behavior. Signal characteristics selection may depend, for example, on the desired displacement of the mechanical load.

Figure 10:
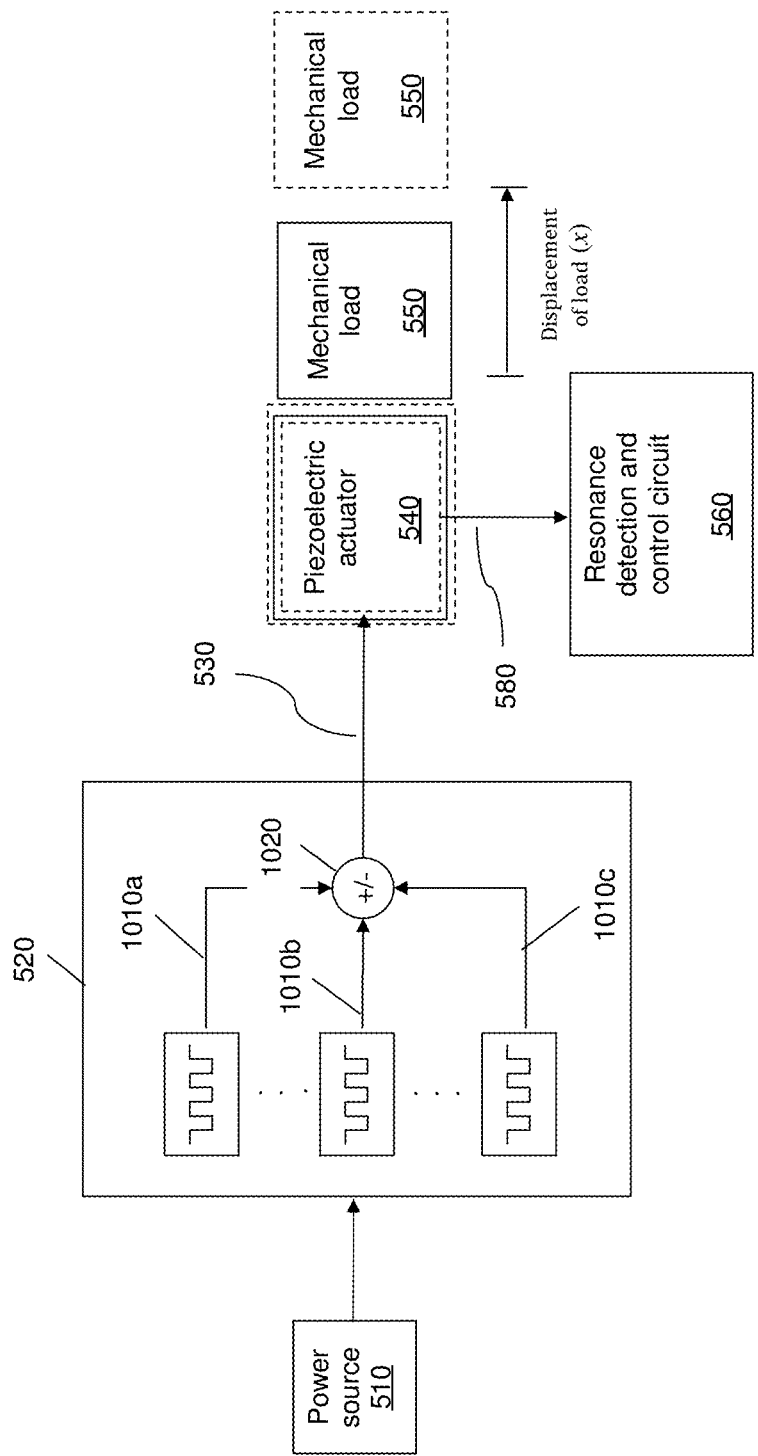
FIG. 10 is a block diagram of one embodiment of a multi-tone driver and resonance detection and control circuit according to the present disclosure.

In general, as shown on FIG. 10, driver 520 according to the current disclosure may comprise two or more input signals 1010*a*, 1010*b*, 1010*c*, etc., coupled to a combining circuit 1020. The combining circuit 1020 may be any form of electronics suitable for combining two or more electric signals into a combined two-tone or multi-tone drive signal 530, e.g., electronics suitable for producing the sum and/or the difference of all or a subset of the input signals 1010*a*, 1010*b*, 1010*c*, etc. The combined drive signal 530 may be coupled directly to the piezoelectric actuator 540, or, optionally, coupled to an impedance matching circuit (not shown) which is then coupled to the piezoelectric actuator 540. This allows for impedance matching (i.e., of the piezoelectric actuator 540 to the output impedance of the driver circuit).

The frequencies of the input signals 1010*a*, 1010*b*, 1010*c*, etc., may be selected so as to optimize certain characteristics of the system. For example, by driving the piezoelectric actuator 540 with two (or more) non-resonant frequencies, energy dissipation in the piezoelectric actuator 540 can be minimized. In one particular embodiment, it may be desirable to indirectly drive the piezoelectric actuator 540 into resonance by selecting the input signals 1010*a*, 1010*b*, 1010*c*, etc., such that the difference or sum of the two or more frequencies, i.e., the frequencies of the one or more combined drive signals 530, equal one or more resonant frequencies of the piezoelectric actuator 540. Without being limited by theory, it will be understood that when two or more electric signals having different frequencies are combined, they will periodically constructively and destructively interfere at difference, sum, and cross-modulation frequencies.

Figure 11:
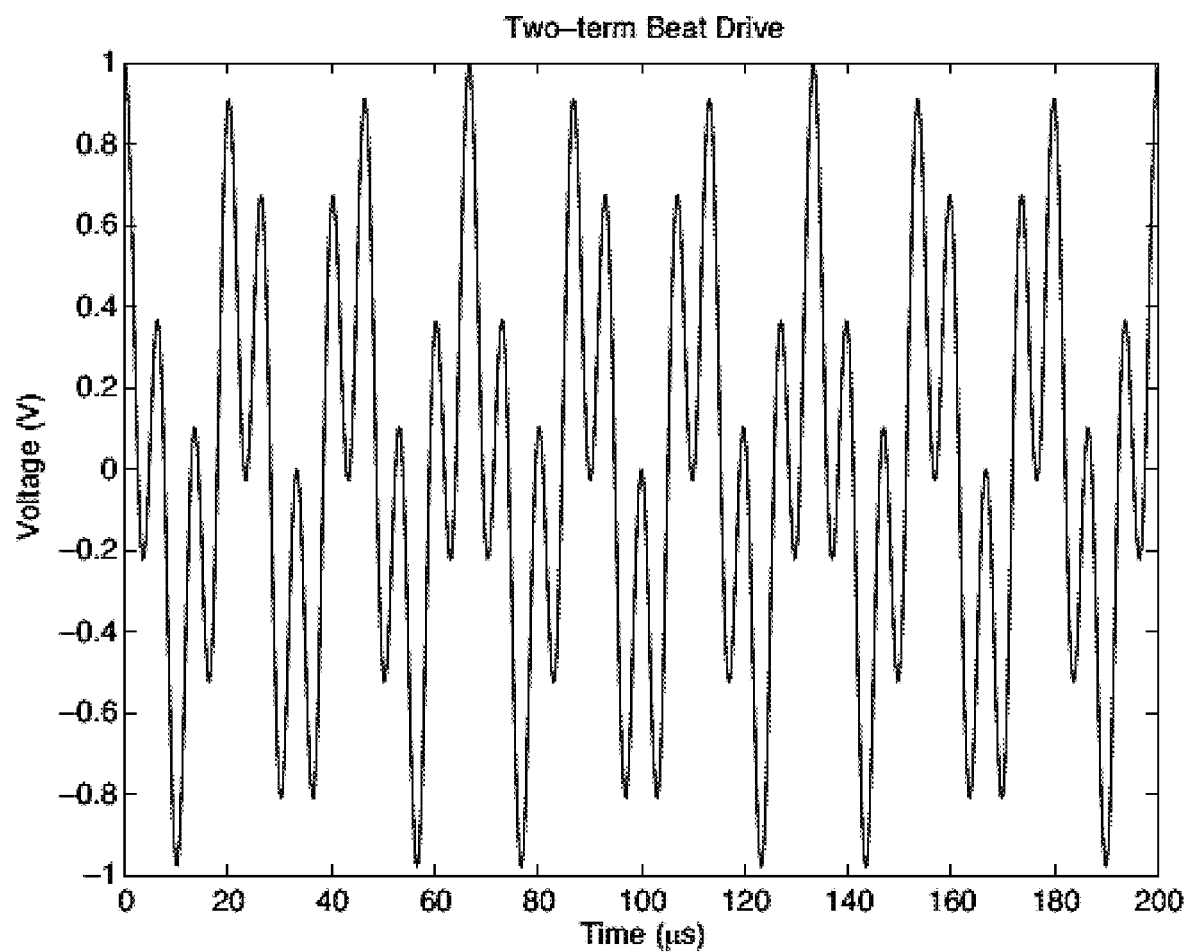
FIG. 11 shows the time-varying voltage output of one embodiment of a two-tone driver according to the disclosure.

This property of interference can be exploited, in combination with amplitude and phase-weighting, such that that the resulting constructive and destructive interference occurs to provide one or more resonant frequencies of the piezoelectric actuator 540 and result in maximum physical displacement x of the load 550. In this manner, the driver 520 may indirectly cause resonant mechanical motion in the piezoelectric actuator 540. FIG. 11 shows the time-varying voltage output 530 of one example of a two-tone driver 520. In one embodiment, the two or more input signals 1010*a*, 1010*b*, 1010*c*, etc., (each having non-resonant frequencies) could be driven at the same combined maximum amplitude as a single-mode drive. This may result in decreased electrical power consumption as compared to the single-mode drive, because the individual signals are at lower frequencies than the resonant frequency. Thus the piezoelectric material benefits from the combined higher frequency since a piezoelectric material has higher impedance at lower frequencies than at the resonant frequency.

Furthermore, by driving the piezoelectric actuator 540 with two or more non-resonant frequencies, the electrical properties of the piezoelectric actuator 540 can be kept completely capacitive while still resulting in mechanical resonance and increased displacement. This allows the piezoelectric actuator 540 to be used directly in resonant converters, further reducing energy losses in the piezoelectric actuator 540 by recapturing the energy in one or more inductors.

Drivers operating in an "envelope mode" according to the embodiments of the present disclosure may improve droplet ejection and lower power consumption in piezoelectric droplet ejector systems. They may additionally extend the range of fluid viscosities which can be ejected from a droplet ejector system. Exemplary operating frequencies in such applications may range from 1 KHz to 5 MHz, such as, for example, 43 kHz and 175 kHz. Using drivers as described herein, the system can support multiple high-displacement frequencies which reduce fluid beading and increase the range of viscosities the system can eject.

In another embodiment, a driver according to the present disclosure may operate in a "Bessel mode". Driver 120 may be configured to operate at two or more frequencies of separate mechanical resonances.

Similar to the operation mode described above, and as shown on FIG. 10, a driver 520 according to the current disclosure may comprise two or more input signals 1010*a*, 1010*b*, 1010*c*, etc., coupled to a combining circuit 1020. The combining circuit 1020 may be any form of electronics suitable for combining two or more electric signals into a combined two-tone or multi-tone drive signal 530, e.g., electronics suitable for producing the sum and/or the difference of all or a subset of the input signals 1010*a*, 1010*b*, 1010*c*, etc. The combined drive signal 530 may be coupled directly to the piezoelectric actuator 540, or, optionally, coupled to an impedance matching circuit (not shown) which is then coupled to the piezoelectric actuator 540. This allows for matching the impedance of the load (i.e., the piezoelectric actuator 540) to the impedance of the driver circuit 520. In order to determine resonance, a feedback signal 580 is used by a resonance detection and control circuit 560 to determine resonance frequencies and optionally to provide feedback to control the frequencies provided by the driver 520.

In embodiments where driver 520 operates in a Bessel mode, the frequencies of the input signals 1010*a*, 1010*b*, 1010*c*, etc., differ from those described above for the envelope mode, such that different characteristics of the system are optimized. In envelope mode implementations, the input signals 1010*a*, 1010*b*, 1010*c*, etc., are specifically selected at non-resonant frequencies which will combine to produce resonant beat frequencies as shown in FIG. 11. In Bessel mode embodiments, for reasons which are described in further detail below, the input signals 1010*a*, 1010*b*, 1010*c*, etc., themselves are at distinct resonance frequencies of the piezoelectric actuator 540 and mechanical load 550. Furthermore, drivers operating in a Bessel mode are optimized to work specifically with non-rectangular loads 550.

Without being limited by theory, it is generally understood that resonance modes of an electromechanical system are assumed to be integer multiples of the resonant frequency, i.e., at harmonics. However, when either the mechanical load 550 or the piezoelectric actuator 540 itself is non-rectangular, the eigenmodes of the ejector mechanism, i.e., the frequencies at which the entire mechanism vibrates simultaneously, do not occur at integer multiples that can be easily generated using harmonic electrical signals 530. This prevents optimum drive of piezoelectric actuator 540 and mechanical load 550 for shapes that are not rectangular. Rather, for circular, or roughly circular, mechanical loads 550, the resonance frequencies occur at Bessel frequencies, i.e., a resonant frequency multiplied by the solutions of the Bessel function. Thus, for embodiments operating in a Bessel mode, the driver 520 may be optimized to provide maximum displacement of circular, or roughly circular, mechanical loads 550, by using two or more input signals 1010a, 1010b, 1010c, etc., having Bessel frequencies.

In certain embodiments, the amplitudes and frequencies of the input signals 1010a, 1010b, 1010c, etc., may be selected such that the system 500 provides improved displacement of the mechanical load 550 at the lower resonant frequency and improved displacement velocity of the mechanical load 550 at the higher resonant frequency. For example, in droplet generator applications, Bessel mode input signals 1010a, 1010b, 1010c, etc., can be driven with amplitude weighting among distinct eigenmodes with desirable shape factors to optimize both mechanical displacement of liquid medication and the velocity of droplet displacement while maintaining an optimum phasing relationship to the electrical drive signal 520 in order to facilitate maximize fluid ejection. By combining two (or more) input signals 1010a, 1010b, 1010c, etc., selected in this manner, the overall quality of the system may be enhanced—the lower frequency mode can enhance the higher frequency mode—and the overall power in each signal can be reduced as compared to a single-mode signal.

By way of example only, a droplet ejector mechanism may have Bessel resonance modes at 50 kHz and 165 kHz. Driving at 50 kHz alone provides 5 μm of displacement; driving at 165 kHz alone provides 800 nm of displacement of the ejector mechanism, but also provides higher velocity and improved spray characteristics. However, in a system according to the present disclosure, both modes may be driven simultaneously. Running both signals at half-power provides both 2.5 μm of displacement from the 50 kHz mode and another 400 nm of displacement from the 165 kHz mode, for a total of 2.9 μm—significantly higher than the 800 nm the 165 kHz signal alone could provide—but with the improved displacement velocity and spray characteristics associated with the 165 kHz signal. In addition, spray is boosted periodically at the beat frequencies, 215 kHz (i.e., the sum of the signals) and 115 kHz (i.e., the difference of the signals). This increases the peak velocity of the system and the range of viscosities the droplet ejector mechanism can eject while suppressing fluid beading.

One having ordinary skill in the art will understand that this is but one example of a combination of modes, and that many other modes of operation could be selected to satisfy differing system requirements. Each bessel mode (different frequency) has a certain velocity and displacement. Thus lower frequency modes have lower velocity, but may have a higher displacement.

According to the present disclosure, the spray is due to a combination of displacement and frequency (velocity). Both aspects can be augmented by using multiple frequencies. In one embodiment, for example, by reducing the amplitude of each electrical drive frequency by one half, the total displacement seen with a droplet ejector mechanism operating at 391 kHz can be increased by over 1700 nm due to the lower-frequency, higher-displacement low-spray mode, while maintaining the correct electrical and mechanical phasing for resonant ejection. In addition, the amount of energy required to power high-viscosity fluid ejection is lowered as compared to the use of single-mode drivers.

As shown, with respect to FIG. 10, drivers operating in both envelope mode and Bessel mode, as described herein, may be implemented using the same logical and electronic components. As described above, the operation of system 500—i.e., in envelope mode or Bessel mode—is a function of the frequencies and amplitudes of the signals applied to the circuitry, as well as the mechanical resonance quality factor.

Figure 12:
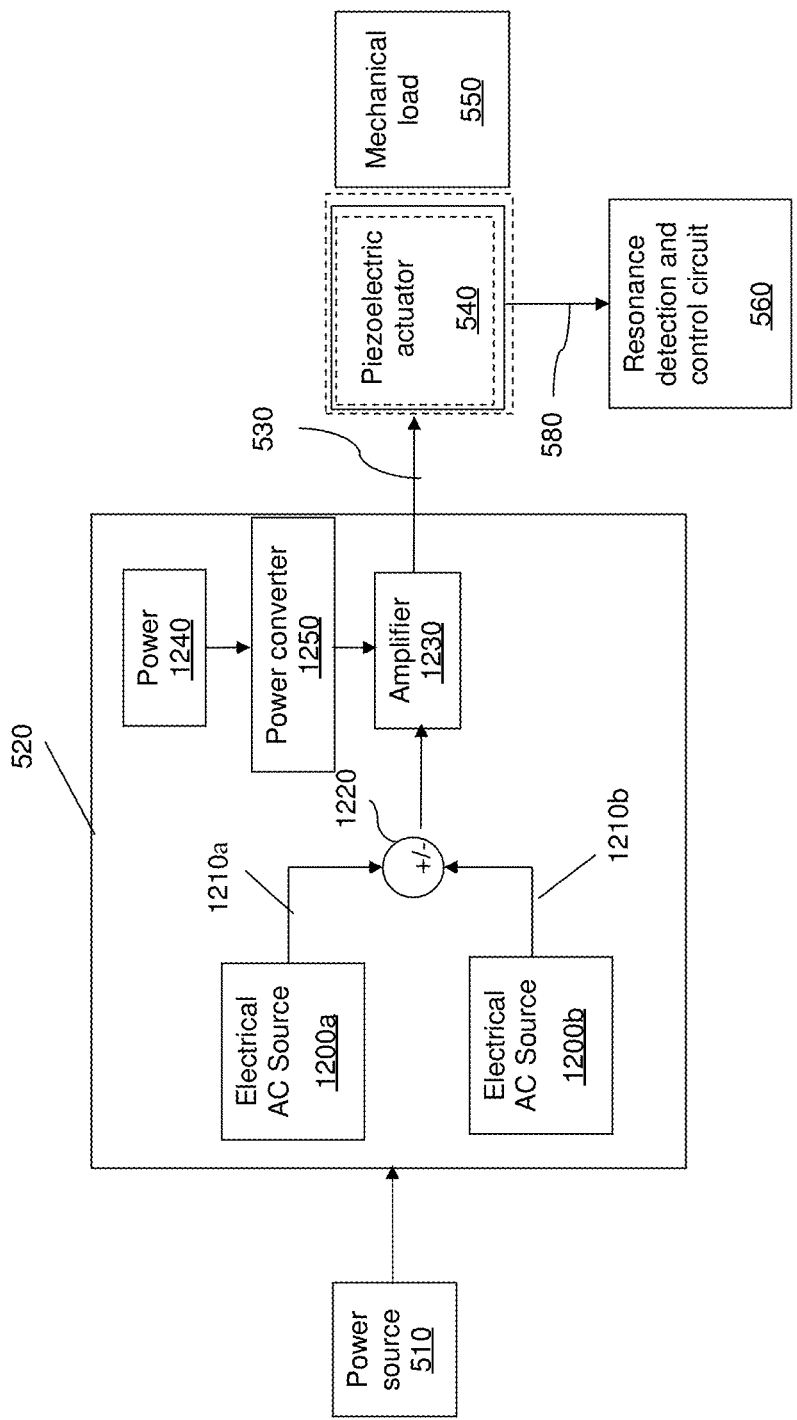
FIG. 12 is a block diagram of another embodiment of a multi-tone driver and resonance detection and control circuit according to the present disclosure.

Other embodiments of the driver are discussed below. In the embodiment of FIG. 12 a driver 520 provides electrical signals 1210a, 1210b by means of electrical alternating current (AC) sources 1200a, 1200b which are then summed by a frequency mixer 1220. These AC sources may be selected so as to generate each signal 1210a, 1210b with the desired frequency and amplitude. In one embodiment, the combined signal 1220 may be coupled to an amplifier 1230, which may be powered by the power source 510, or alternatively by a separate power source 1240, which may be coupled to a power converter 1250 such as an AC/DC converter or a DC/DC converter in the event that a large output voltage, current, or power is needed for actuation of the piezoelectric actuator 540. Such an amplifier 1230 may be linear or nonlinear and can be single-ended or differential. A feedback signal 580 is used by a resonance detection and control circuit 560 to determine resonance frequencies and optionally to provide feedback to control the frequencies provided by the AC sources 1200a, 1200b.

Figure 13:
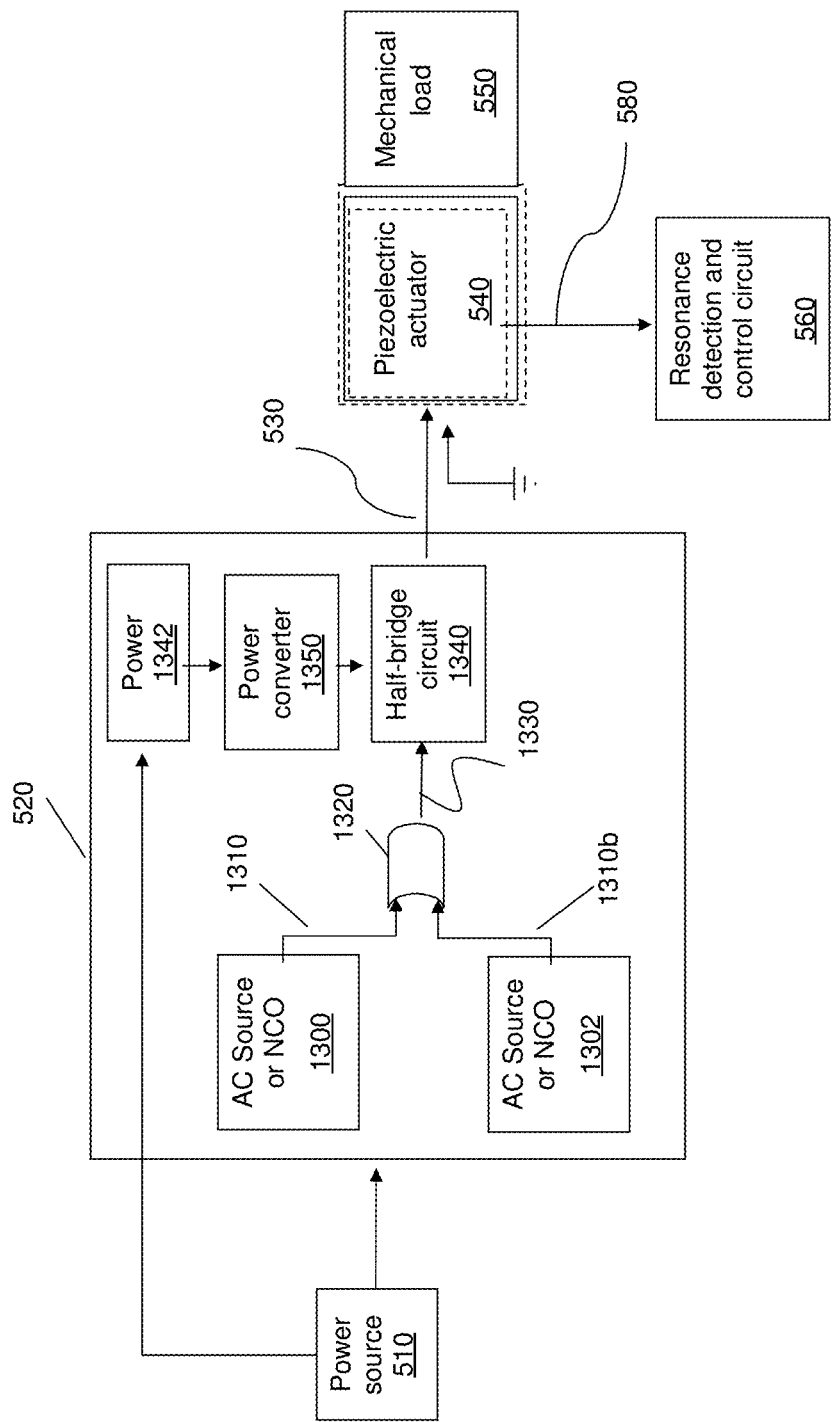
FIG. 13 is a block diagram of yet another embodiment of a multi-tone driver and resonance detection and control circuit according to the present disclosure.

FIG. 13 shows another implementation of a driver 520 according to the current disclosure. In this embodiment, the driver 520 may comprise one or more electrical sources or numerically controlled oscillators (NCOs) 1300, 1302 with distinct frequencies 410a, 410b. The signals 1310a, 1310b generated by these sources 1300, 1302 can then be summed digitally in an OR gate or other digital logic 1320 to create a multi-frequency signal similar to performing a pulse-width modulation (PWM). Then, as shown in FIG. 13, the resultant signal 1330 may be used to drive a half-bridge circuit 1340 to generate a single-ended drive signal 130 across the piezoelectric 150. The bridge circuit 1340 may be fed from the power source 110 or a separate power source 1342, optionally via a power converter 1350. A feedback signal 580 is used by a resonance detection and control circuit 560 to determine resonance frequencies and optionally to provide feedback to control the frequencies provided by the NCOs 1300, 1302.

Figure 14:
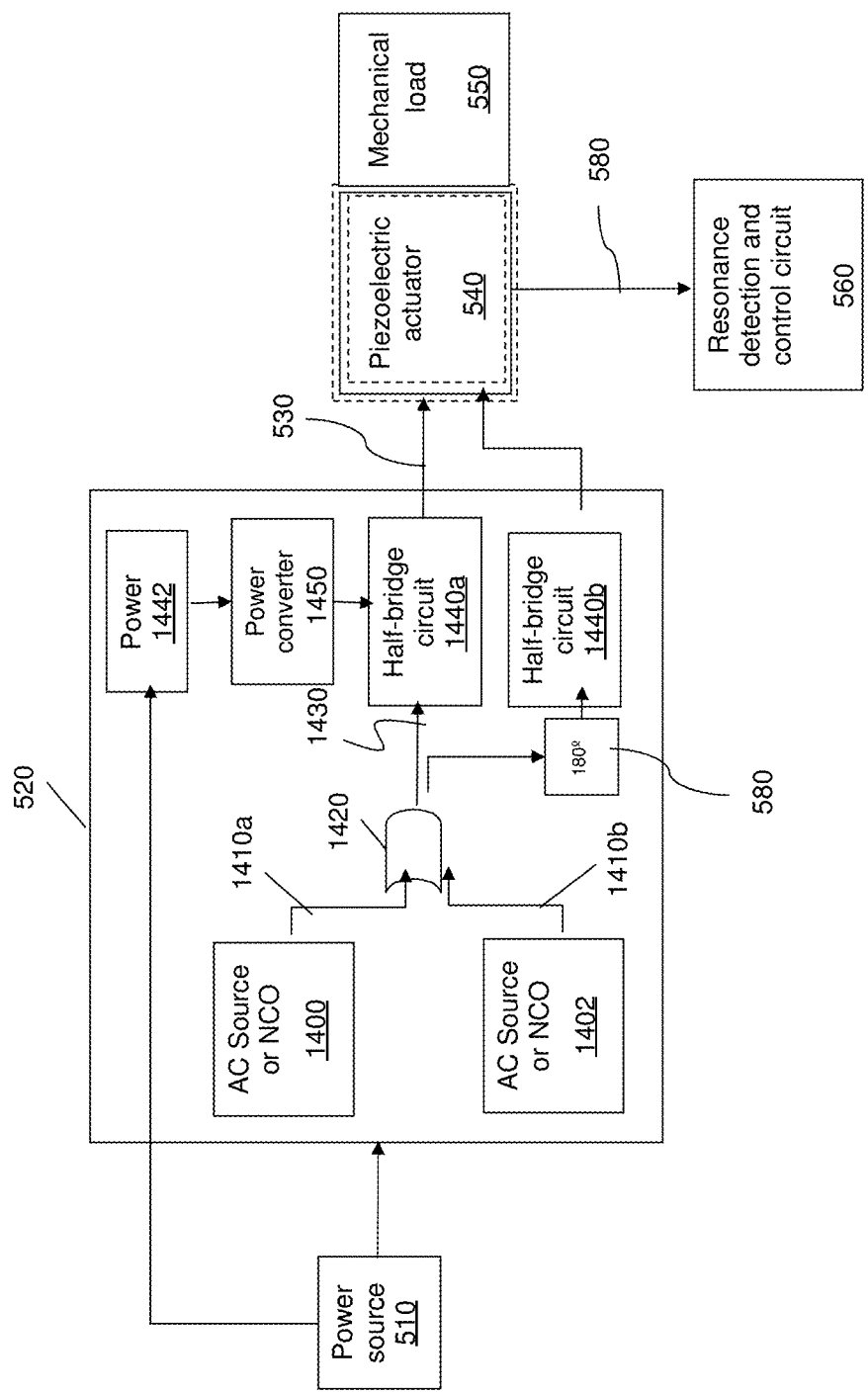
FIG. 14 is a block diagram of yet another embodiment of a multi-tone driver and resonance detection and control circuit according to the present disclosure.

In another embodiment, shown in FIG. 14, the driver 520 may again comprise one or more electrical sources or numerically controlled oscillators (NCOs) 1400, 1402 with distinct frequencies 1410a, 1410b. The signals 1410a, 1410b generated by these sources 1400, 1402 can be summed digitally in an OR gate or other digital logic 1420 to create a multi-frequency pulse-width modulated (PWM)

signal. Then, as shown in FIG. 14, the resultant signal 1430 may be used to drive two half-bridge circuits 1440a and 1440b, the half-bridge circuit 1440b being fed via an inverter 1480 to provide an anti-phase version of the output 1430, in order to form a full-bridge drive. The bridge circuits 1440a, 1440b may be fed from the power source 110 or a separate power source 1442, optionally via a power converter 1450. A feedback signal 580 is used by a resonance detection and control circuit 560 to determine resonance frequencies and optionally to provide feedback to control the frequencies provided by the NCOs 1400, 1402.

Figure 15:
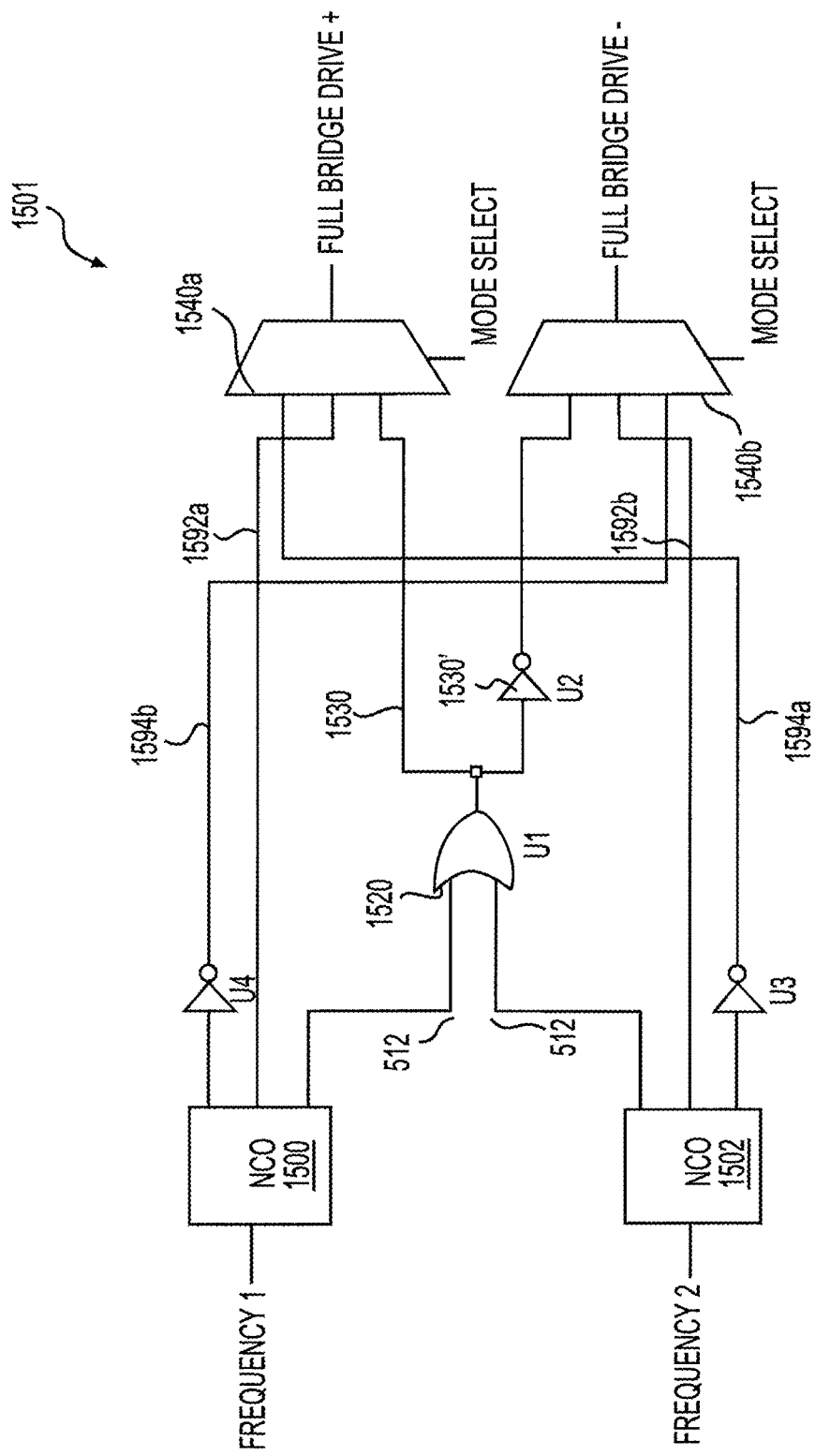
FIG. 15 is a schematic circuit diagram of one embodiment of a driver according to the present disclosure.
Figure 16:
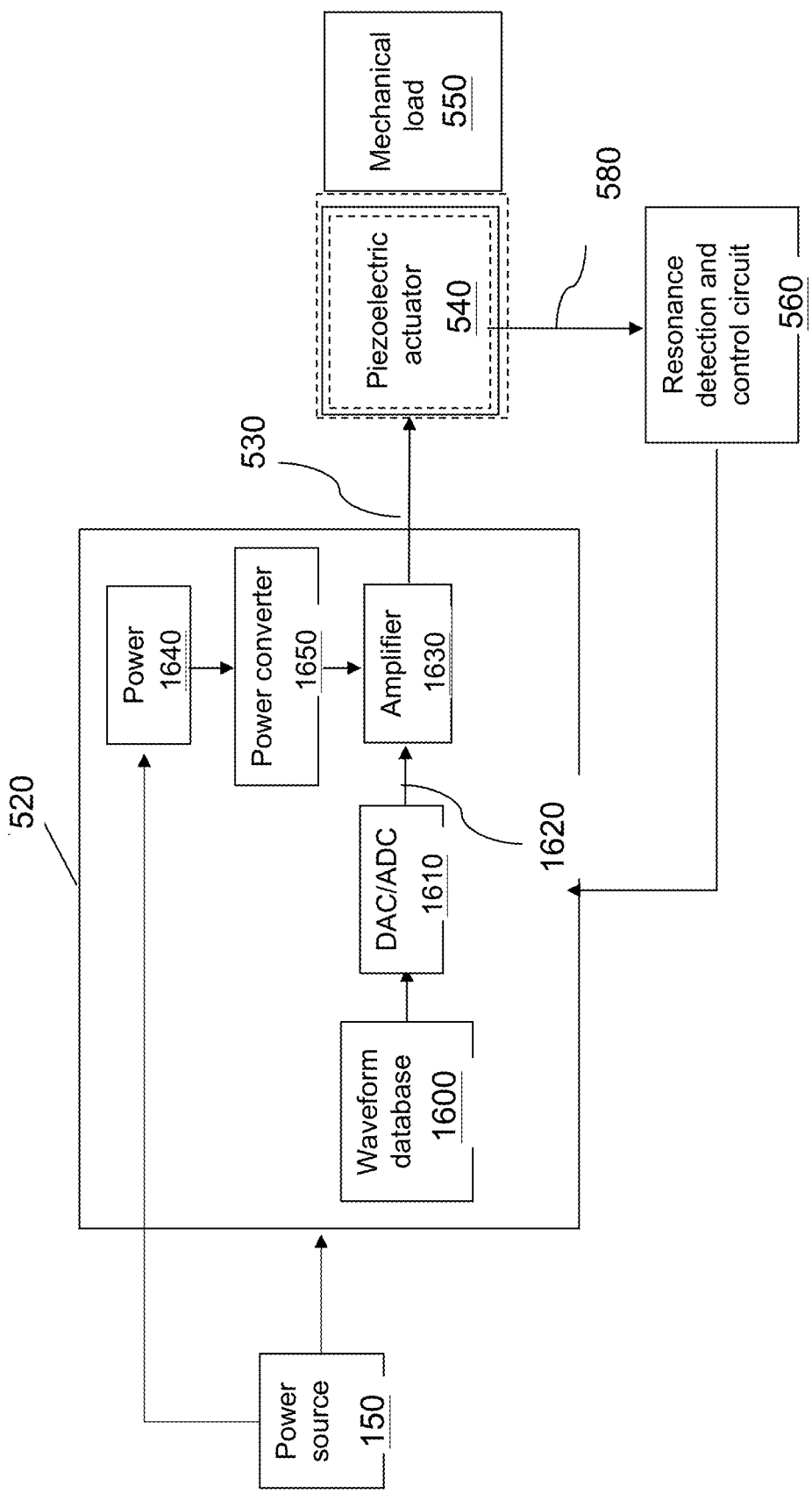
FIG. 16 is a block diagram of yet another embodiment of a multi-tone driver and resonance detection and control circuit according to the present disclosure.

One having ordinary skill in the art will understand that two separate sources and appropriate logic may be used to control the phasing and dead time between half-bridge drives. FIG. 15 shows one embodiment of a circuit diagram implementing such a full-bridge drive 1501, wherein multiplexers 1590a, 1590b receive additional non-inverted control line inputs 1592a, 1592b, respectively, and inverted control lines 1594a, 1594b, respectively from the NCO's. The multiplexers 1592a, 1592b allow either a mixed two frequency signal to drive a full bridge, or separate frequencies to drive each half of a full bridge. The control lines allow different modes of operation, e.g., using a single NCO and inverter to drive both halves of a full bridge at a single frequency, or using two NCO's in the shown configuration at the same frequency but in anti-phase. FIG. 16 shows yet another embodiment of a driver 520 according to the current disclosure. In this embodiment, the driver 520 comprises a waveform database 1600 for example incorporating a digital representation of a drive signal 530. The waveform database 1600 may be utilized to generate an arbitrary single-tone or multi-tone digital waveform signal for a digital-to-analog converter (DAC) 1610 for conversion into a corresponding electrical signal 1620. This signal 1620 may be boosted by an appropriately powered amplifier 1630 (powered by the power supply 510 or by a separate power supply 1640, as shown on FIG. 16). The amplifier 1630 may be linear or nonlinear, and can be single-ended or differential. The resultant drive signal 530 is then applied to a piezoelectric actuator 540 in order to drive a mechanical load 550, for example a fluid-loaded ejector plate or an ejector plate with fluid-filled droplet generator. Feedback signal 580 is used by a resonance detection and control circuit 560 to determine resonance frequencies and optionally to provide feedback to control the selection of frequency(s) provided by the database 1600.

Figure 17:
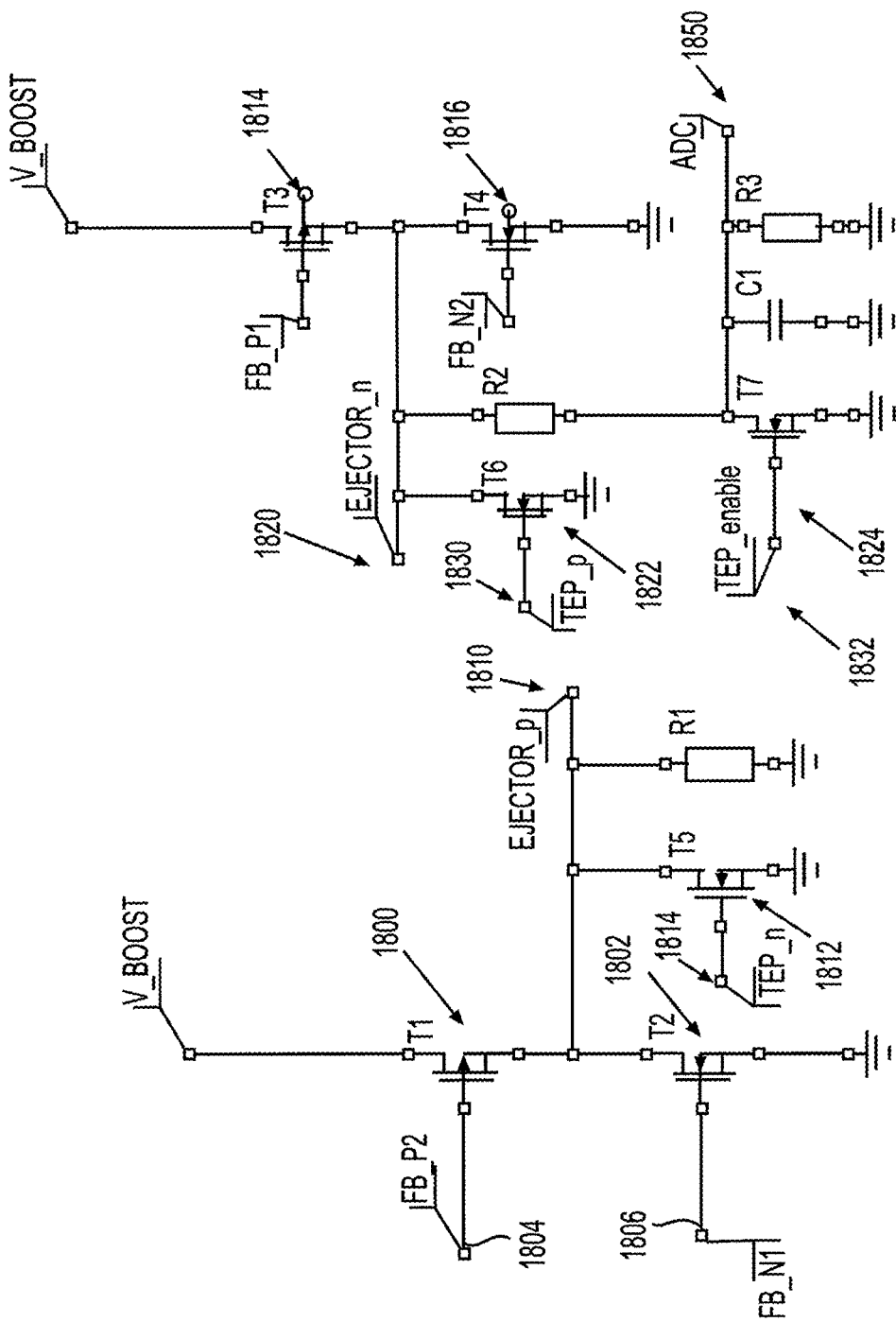
FIG. 17 is a circuit diagram of one embodiment of a full bridge circuit with a TEP measurement circuit.

FIG. 17 shows a circuit diagram of one embodiment of a driver 120 circuit according to the current disclosure providing a full bridge driver and resonance measurement circuit. In this embodiment, the driver 120 comprises a first PMOS/NMOS pair 1800,1802, which switches a positive voltage, Vboost, between the electrodes of a piezoelectric actuator (ejector) at the system drive frequency using the drive signal 1804 and inverted drive signal 1806. The first PMOS/NMOS pair 1800/1802 drives a first or positive side of the actuator by means of signal 1810. The drive frequency may range, e.g., from 1 Hz to 10 MHz, and the Vboost voltage may range, e.g., from 6 Volts to 75 Volts. The voltage on the output 1810 is controlled by means of a transistor 1812, which is controlled by a Time-Energy-Product (TEP) feedback signal 1814, as part of a TEP measurement circuit that is shown in enlarged view in FIG. 18. This allows for the signal from the driver to be decoupled for purposes of monitoring the output signal from the piezoelectric actuator as is discussed in more detail below.

The driver further includes a second PMOS/NMOS pair 1814, 1816 to drive a second or negative side of the actuator by means of a signal 1820. The drive voltage 1820 to the driver is controlled by turning off transistor 1822. During monitoring of the output voltage from the piezoelectric actuator, the transistor 1822 is briefly turned on to prevent driver voltage from passing through to the ADC (not shown but its location is indicated by reference numeral 1850). As is discussed in greater detail below, the transistor 1822 is then turned off and transistor 1824 is turned off by TEP enable signal 1832, to allow the output voltage to pass through to the ADC (not shown). Transistor 1824 can also be driven at the original signal drive frequency via the TEP enable signal 1832 to provide a correlated output signal.

Figure 18:
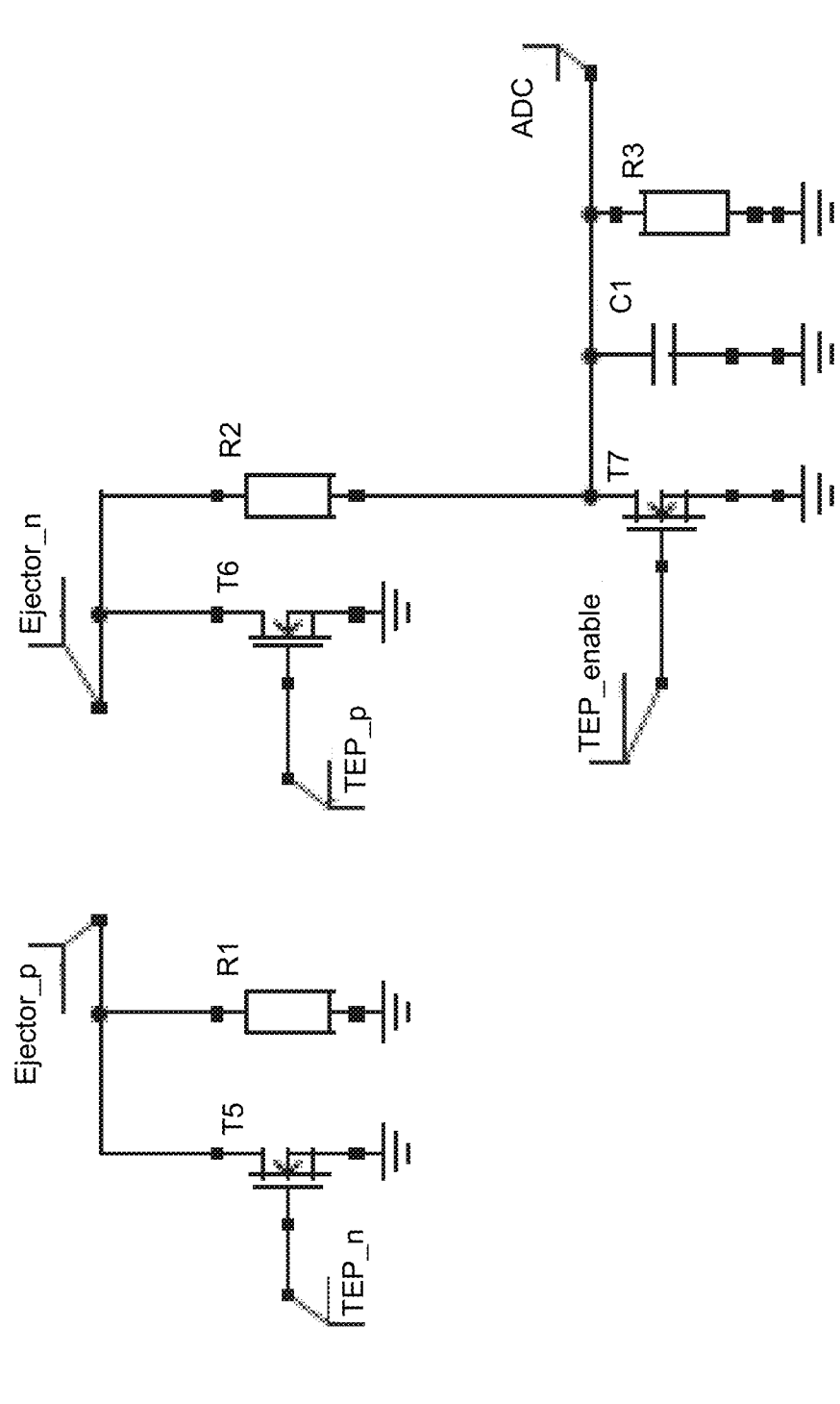
FIG. 18 is an enlarged view of the TEP measurement portion of the circuit of FIG. 17.

FIG. 18 shows the voltage control circuitry of FIG. 17 in an enlarged view. The circuit is differentially balanced by providing equal resistances R1 and R2. The TEP_enable 1832 keeps the T7 transistor 1824 on during drive. This keeps the 45 V+ from reaching the ADC, which has a maximum input of VDD<=6V. Resistor R2 and capacitor C1 form an integrator circuit to measure ejector ringdown.

The signals TEP_n 1814 and TEP_p 1830 short the signals Ejector p 1810 and Ejector n 1820, respectively for a brief period of time after the drive is cut off to drain the voltage to a low enough level to avoid blowing up the ADC. Thereafter, the TEP_n 1814 remains on connecting Ejector_p 1810 through transistor T5 1812 to ground. The signal TEP_p 1830 cuts off transistor T6 1822, switching Ejector_n into the ADC port path. The TEP_enable 1832 either disables transistor T7 1824 or drives it at the original drive frequency for correlation. The RC integrator in front of the ADC simply integrates the output signal and the ADC samples at a specified time to get a value for the amplitude of the energy in the TEP signal.

Figure 19:
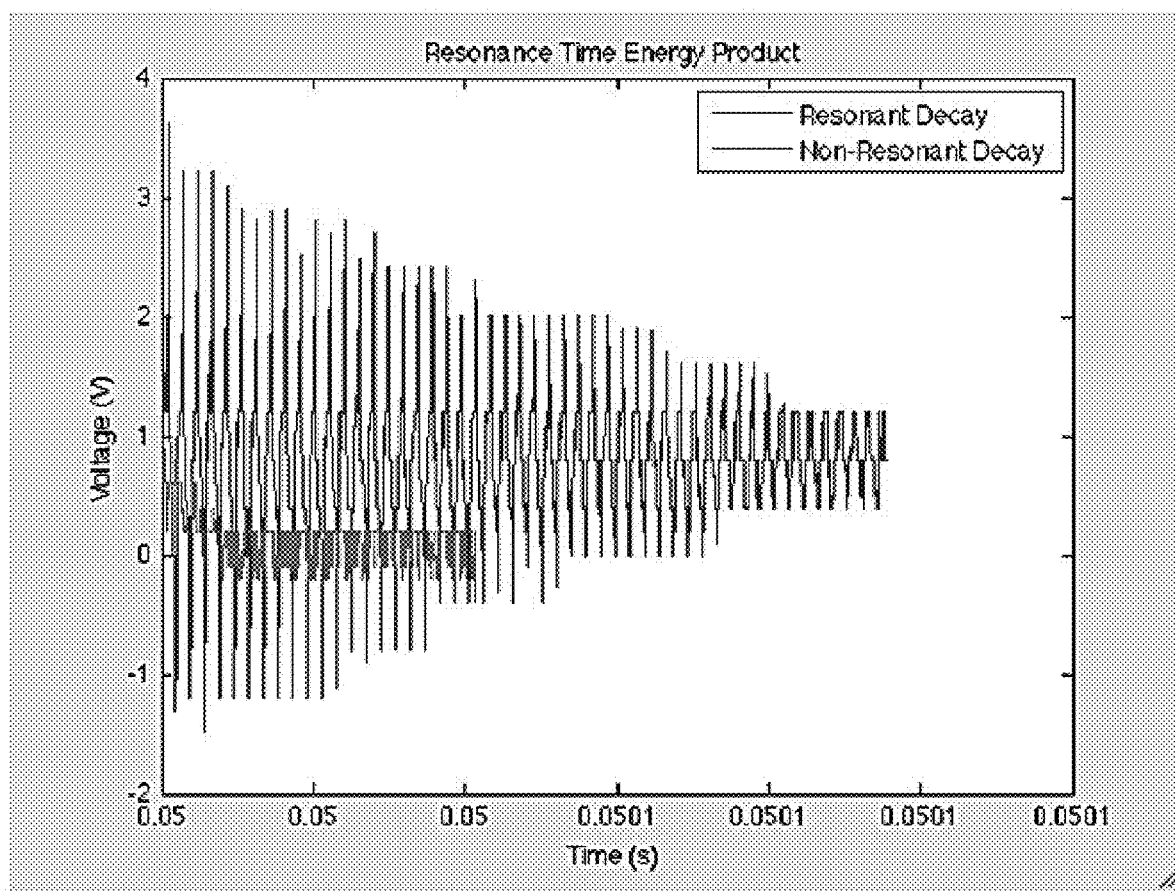
FIG. 19 is a Voltage vs. Time waveform showing resonant and non-resonant decay.

Regardless of the amplitude and/or frequency of the drive signal 130, when the piezoelectric actuator 540 is driven by a drive signal 530, some amount of energy will be both stored and released in the electromechanical mechanism 500. That said, the question of how much energy is stored and dissipated in the piezoelectric actuator 540 is a function of, among other things, the frequency of the drive signal 530, the ambient temperature, and the nature of the mechanical load 550. As described previously, piezoelectric actuators are often driven in resonance modes to provide increased or maximum displacement of the mechanical load. At the resonant frequency of the piezoelectric actuator 540, energy is stored and released at a different rate than when the piezoelectric is in a non-resonant mode. When the mechanism is in resonance, energy will remain in the mechanism and ring in the piezoelectric for some (measurable) period of time before it eventually decays and the mechanism returns to its initial resting state. When the mechanism is not in resonance, energy drains from the mechanism may be almost immediate. For example, FIG. 19 shows the time-varying voltage of one embodiment of a system according to the current disclosure, during this decay period in both resonant and non-resonant modes. It is possible to exploit this characteristic of electromechanical systems to determine when the mechanism is in resonance and when it is not.

Figure 20:
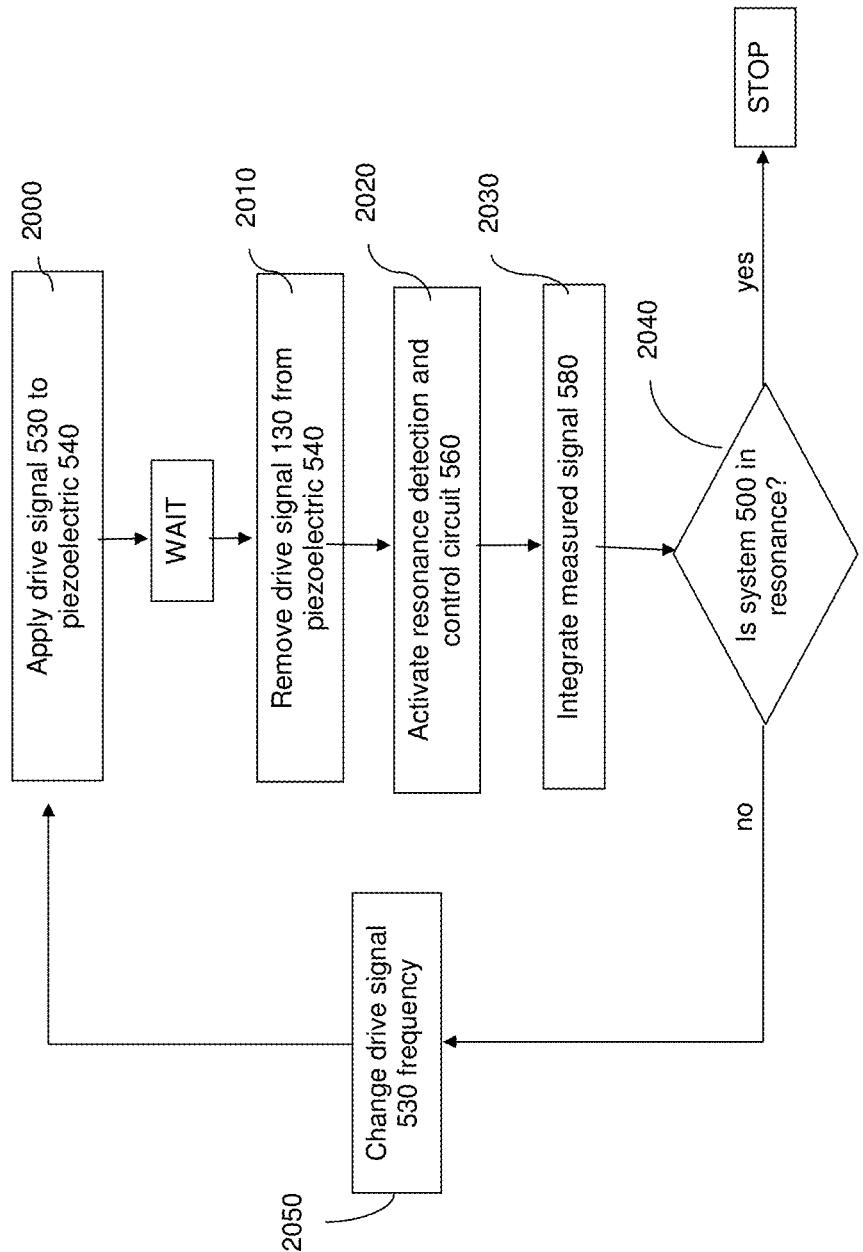
FIG. 20 is a flow diagram illustrating one embodiment of a method of determining resonance of an electromechanical mechanism.
Figure 21:
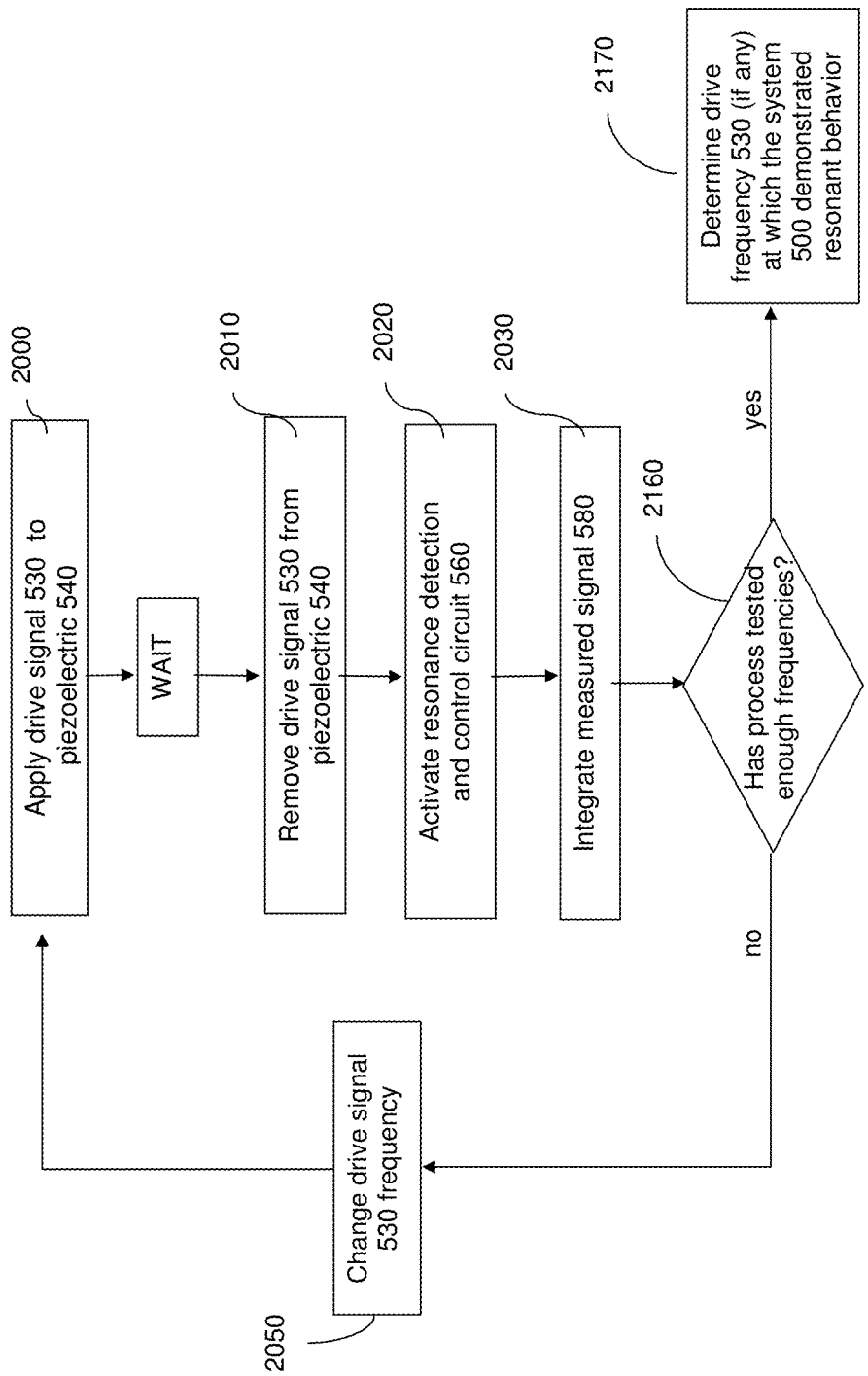
FIG. 21 is a flow diagram illustrating another embodiment of a method of determining resonance of an electromechanical mechanism.

FIGS. 20 and 21 show examples of methods of the disclosure for generating energy profiles of the mechanism 500, which can be used for determining whether or not the mechanism is in resonance. Similar steps in the flow charts are depicted by the same reference numerals for purposes of simplicity. As shown on FIG. 20, at step 2000 a drive signal 530 may be applied to the piezoelectric actuator 540 for a finite period of time. Depending on the overall mechanism requirements and the type of characteristics to be detected, the piezoelectric actuator 540 may or may not be coupled to a mechanical load (not pictured). Generally speaking, the drive signal 530 should be applied to the piezoelectric actuator 540 for at least one period of the waveform for piezoelectric modes (where the piezoelectric actuator is not coupled to a load) and two periods of the waveform for membrane modes (where the piezoelectric actuator is coupled to a load such as a fluid filled ejector mechanism), regardless of frequency, to obtain a detectable signal. The energy in the load builds for a period of time dictated by the quality factor of the resonance, and can be driven for any amount of time greater than the minimum number of periods required.

At step 2010, the signal 530 is no longer applied to the piezoelectric actuator 540. This "stop" may be caused by simply powering off the driver 520, disconnecting the driver 520 (e.g., electrically, by tri-stating drive FETs), or some other action sufficient to prevent the signal 530 from being applied to the piezoelectric actuator 540. At this point, the mechanism 570 will revert to its initial resting state, i.e., the piezoelectric actuator 540 will no longer be actuated to displace a mechanical load 550, and the energy remaining in the mechanism will dissipate. How quickly the signal 580 decays will, as discussed previously, depend on whether the mechanism is in resonance. To make the signal 580 more easily detectable, it may be desirable to increase the amplitude of the signal 580 by stopping the drive waveform at a peak of the drive signal 530 rather than at a zero crossing. It is noted, however, that stopping the drive signal 530 at a zero crossing may be more detrimental to measuring mechanical resonances than piezoelectric resonances.

At step 2020, a resonance detection and control circuit 560, coupled to the piezoelectric actuator 140 as shown on FIG. 5, for example, may be activated to measure various characteristics associated with the decay of the signal remaining in the piezoelectric mechanism 570. At step 2030, the resonance detection and control circuit 560 may integrate the detected signal 580. The integrated signal will have the greatest amplitudes, reflecting the maximum physical movement of the piezoelectric actuator 540 and corresponding displacement of the mechanical load 550, at the resonant frequencies of the mechanism 570. The resonance detection and control circuit 560 may be synchronized with the driver 520 so as to window the integration of the measured signal 580 over the relevant period of decay. For example, if integration began too early it could pick up the original drive signal 530, which is not of interest at this point in the analysis.

In the embodiment of FIG. 20 a resonance determination is made at step 2040 based on an increase in the detected signal 580 compared to the signal 580 taken at the previous input signal 530 frequency. If no such increase is detected, the frequency of the input signal 530 is changed at step 2050 to monitor the effect on the piezoelectric mechanism 170. Thus, at step 2040, an assessment could be made as to whether the mechanism is in resonance or not. In certain embodiments the process of steps 2000 through 2040 could be repeated several times to actually determine the resonant frequency of the system. Each time it is determined at step 2040 that the mechanism is not in resonant mode, the drive frequency 520 could be adjusted at step 2050. For example, the frequency of the drive signal 530 applied to the piezoelectric may be varied in steps of, for example, 1 kHz apart, so as to observe the response of the mechanism 500 at varying drive frequencies until a clear spike in amplitude—i.e., a resonant response—is observed.

In the embodiment of FIG. 21 a defined set of frequencies are tested for the input signal 530, by counting down the number of frequencies tested and determining at step 2160 whether the defined number of frequencies has been tested and if not, changing the frequency at step 2050 and applying the new input signal 530. Once the requisite number of frequencies has been run, a determination is made at step 2170 as to the frequency at which the highest amplitude detected signal 580 was obtained. Thus in the embodiment of FIG. 21, the order of the steps could be changed slightly such that the determination as to whether a resonant response was observed occurs at the end of the process. At step 2000 the drive signal 530 may be applied to the piezoelectric actuator 540, and then at step 2010 it may be removed. The resonance detection and control circuit may be activated at step 2020 and the measured signal 580 may be integrated at step 2030. At step 2160, the method might determine whether it has tested enough frequencies; for example, it might be required to test 10 different frequencies. If only one (or any number less than 10) has been tested, the method could jump to step 2050 and change the drive signal frequency. This process may be repeated until the requisite number of frequencies has been tested, at which point it could be determined whether one of the tested frequencies has demonstrated resonant behavior, i.e., as shown at step 2170.

The foregoing examples have assumed the use of single-tone drive frequencies to locate the resonant frequency. One having ordinary skill in the art will understand, however, that these processes could be expedited by, for example, using a multi-tone drive signal 530. For instance, the drive signal could have 10 tones spaced at 1 kHz, starting at 45 kHz, with the tones having equal amplitudes. In this manner, each of the 10 frequencies could be analyzed simultaneously, i.e., send the 10 frequency signal before waiting and evaluating the output signal 580. In yet another embodiment, the drive signal 530 could be a chirp, or an arbitrary wave form.

Figure 22:
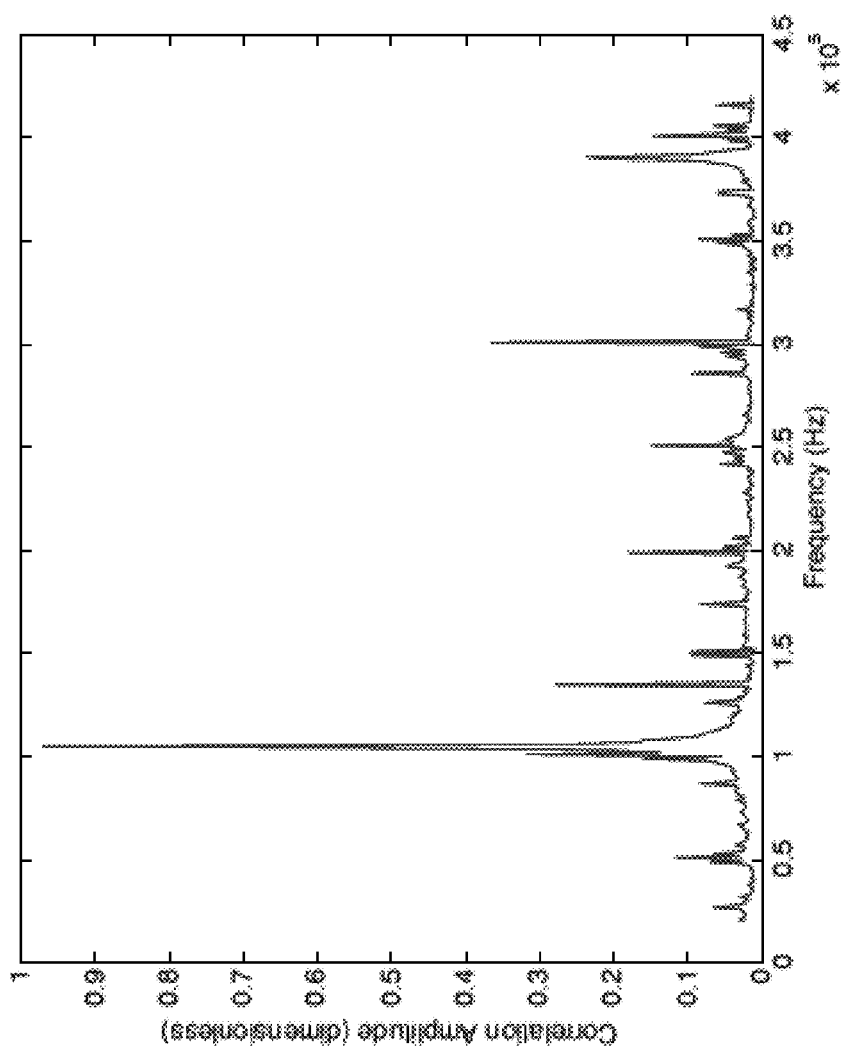
FIG. 22 shows a sample waveform (amplitude versus frequency) of an integrated signal of one embodiment of a mechanism according to the present disclosure.
Figure 23:
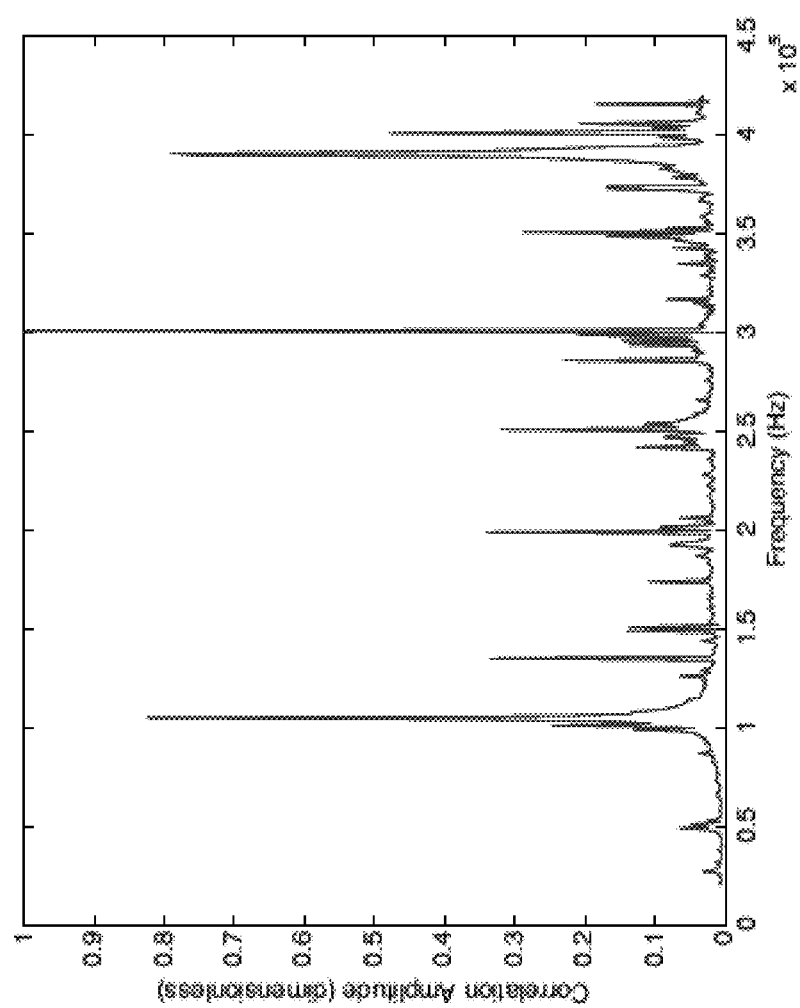
FIG. 23 shows a sample waveform (amplitude versus frequency) of an integrated signal of another embodiment of a mechanism according to the present disclosure.
Figure 24:
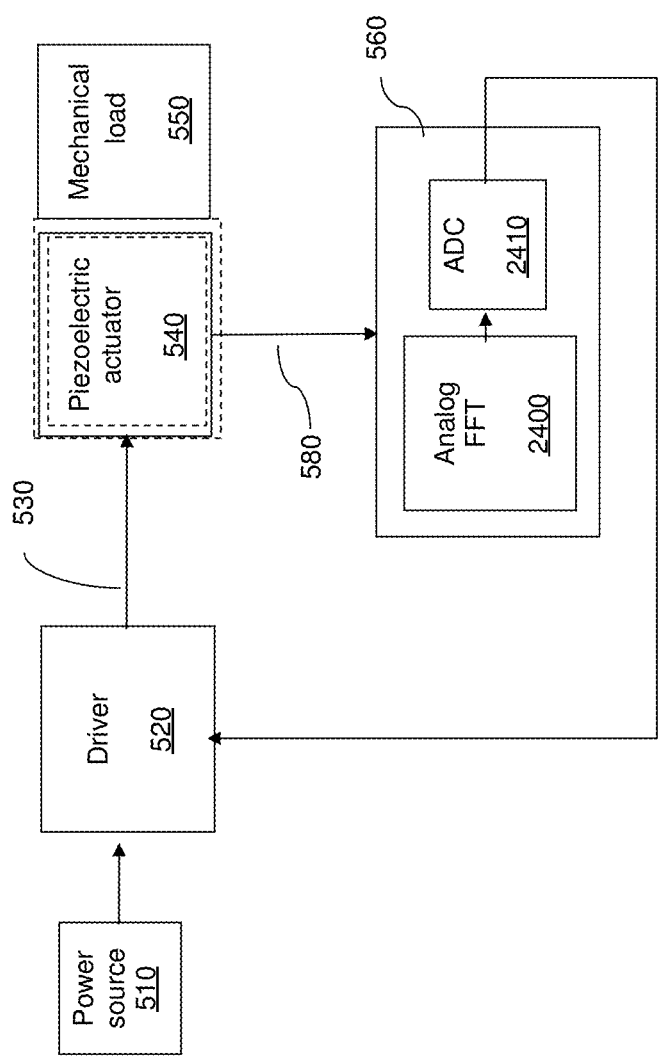
FIG. 24 is a block diagram of another embodiment of a driver and resonance detection and control circuit according to the present disclosure.
Figure 25:
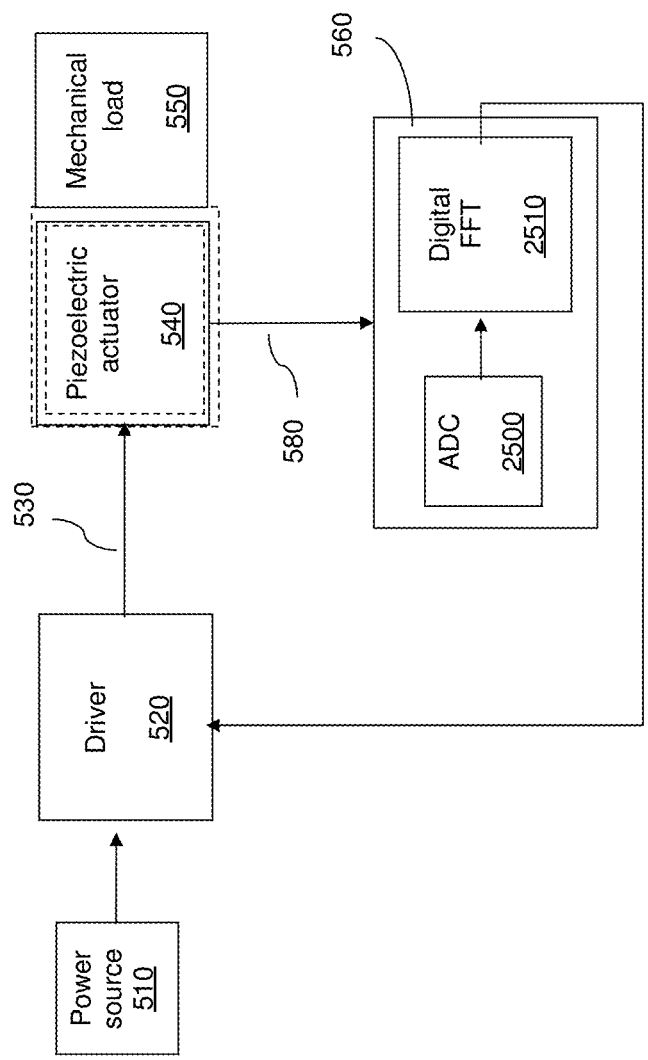
FIG. 25 is a block diagram of yet another embodiment of a driver and resonance detection and control circuit according to the present disclosure.

FIGS. 22 and 23 show the processed (integrated value at each frequency) sample waveforms (amplitude versus frequency) of the integrated signal of two exemplary systems according to the current disclosure. Specifically, FIG. 22 shows a sample waveform of a correlator-based system, i.e., as shown in FIG. 26 and described in further detail below, while FIG. 23 shows a sample waveform of a fast Fourier transform (FFT) based system, i.e., as shown in FIGS. 24 and 25 and described in further detail below.

The foregoing examples have assumed the use of single-tone drive frequencies. One having ordinary skill in the art will understand, however, that these processes could be expedited by, for example, using a multi-tone drive signal 530. For instance, the drive signal could have 10 tones spaced at 1 kHz, starting at 45 kHz, with the tones having equal amplitudes. In this manner, each of the 10 frequencies could be analyzed simultaneously. In yet another embodiment, the drive signal 130 could be a chirp, or an arbitrary wave form. For purposes of this application, a Chirp is a signal where the frequency of the signal is swept continuously at a specified rate. The rate can be a linear or nonlinear function.

The foregoing description describes at a high level how such a system works. One having ordinary skill in the art will understand that there are a variety of suitable electronic implementations. For example, a suitable resonance detection and control circuit 160 may be implemented in many different ways. In two embodiments, as shown in FIG. 24 and FIG. 25, the resonance detection and control circuit 560 may comprise a fast Fourier transform circuit. In the embodiment of FIG. 24, an analog FFT circuit 2400 is coupled to an analog-to-digital converter (ADC) 2410. In the embodiment of FIG. 25, a resonance detection and control circuit 560 may comprise an ADC 2500 coupled to a digital FFT 2510. A digital FFT may be preferable over an analog FFT implementation because of ease of implementation in a standard microprocessor or microcontroller, such as a PIC microprocessor.

Figure 26:
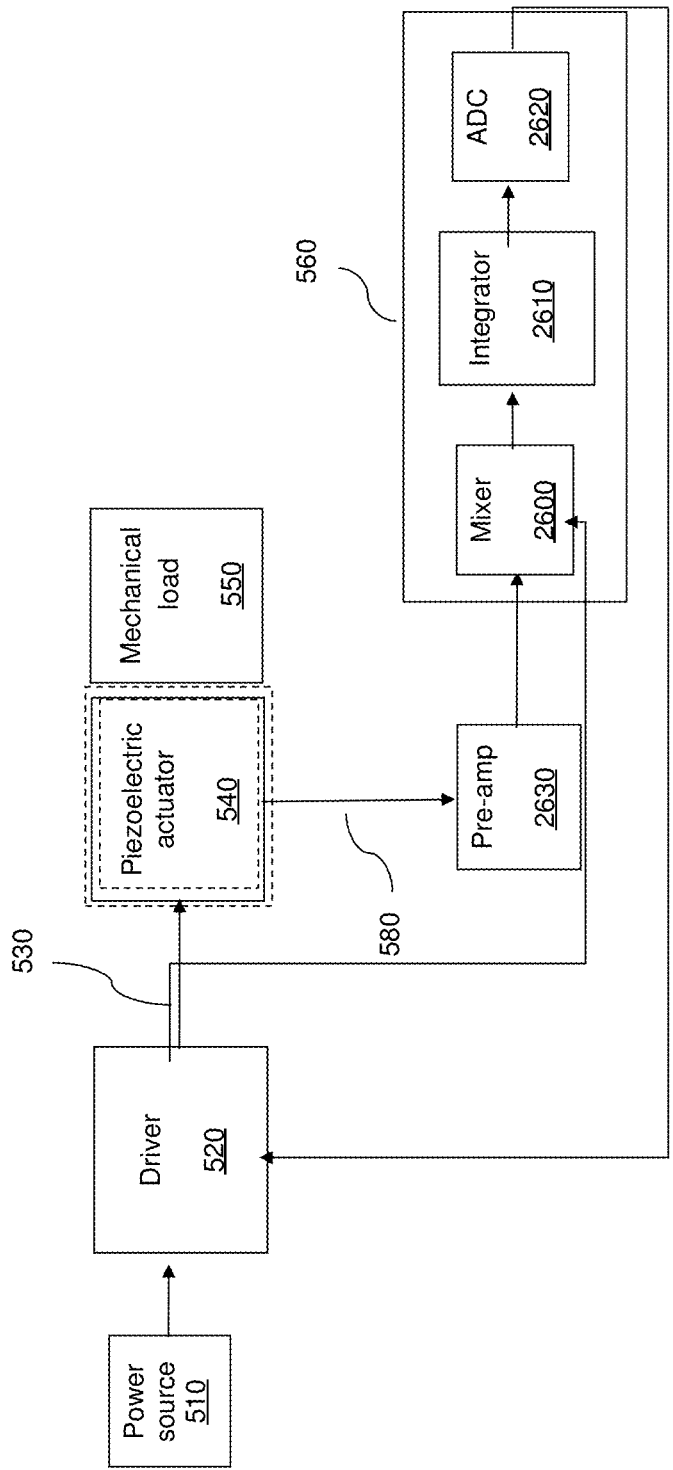
FIG. 26 is a block diagram of yet another embodiment of a driver and resonance detection and control circuit according to the present disclosure.

In yet another embodiment, as shown in FIG. 26, a resonance detection and control circuit 560 may receive the output signal 580 after it has been amplified in a pre-amplifier stage 2630. The resonance detection and control circuit 560, in this embodiment, comprises a mixer 2600 coupled to an integrator 2610. The mixer 2600 may be any form of digital or analog circuitry capable of multiplying the drive signal 530 and the measured signal 580. Such an implementation may be preferable in situations requiring very fast processing, as a mixer may be able to perform calculations in real time. The integrator 2610 may then be coupled to an ADC 2620 or any other amplitude measurement or tracking circuit.

One having ordinary skill in the art will understand that, depending on the characteristics of the overall system, it may be desirable to include certain optional pre-processing components. For example, as shown on FIG. 26, and as discussed above, it may be desirable to place a pre-amp 2630 between the piezoelectric actuator 540 and the resonance detection and control circuit 560 such that the measured signal 580 and/or the drive signal 530 is amplified before processing. Alternatively, a resistive or capacitive divider (not pictured) may be coupled to the resonance detection and control circuit 560 in order, for example, to convert the output 580 of the piezoelectric actuator 540 to a voltage suitable for input to the components implementing the resonance detection and control circuit 560. It will be understood that these components additionally may be desirable with respect to other implementations, including but not limited to those shown in FIGS. 24 and 25.

Figure 27:
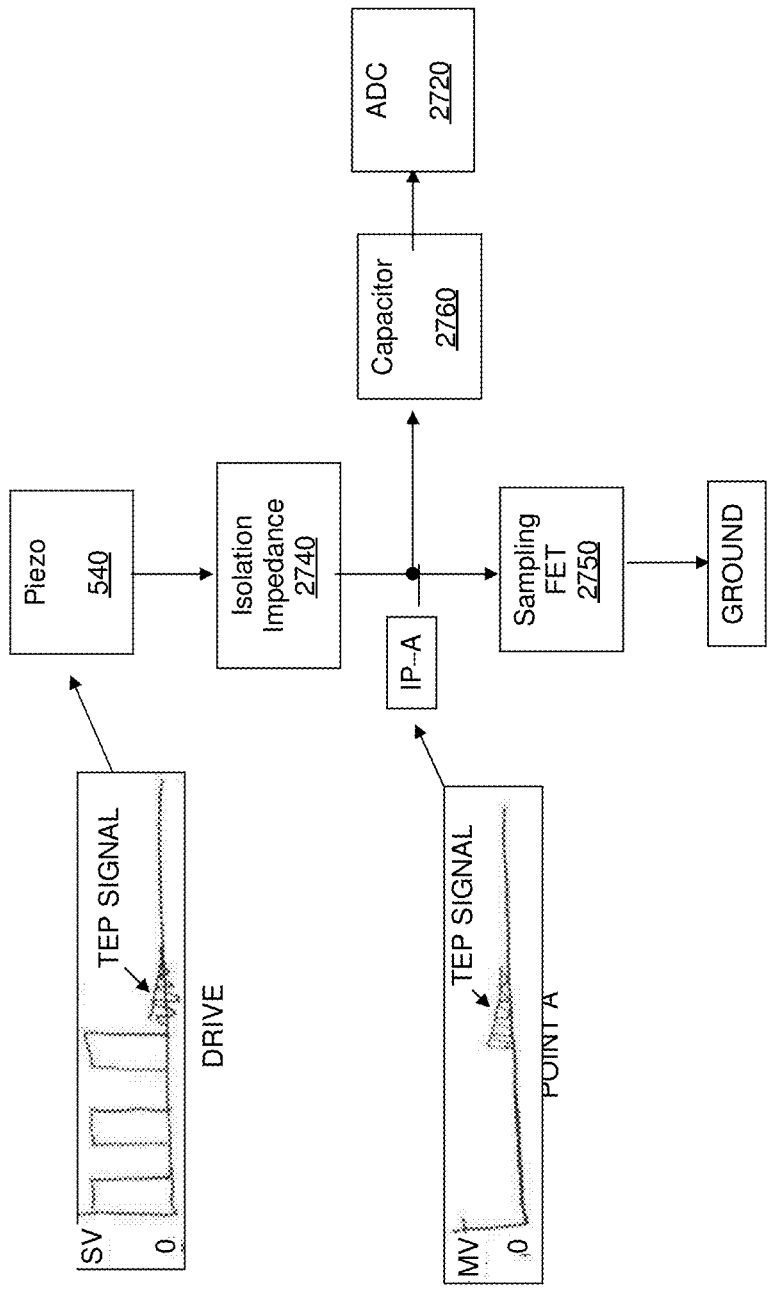
FIG. 27 is a block diagram of one embodiment of a TEP resonance detection circuit.

FIG. 27 is a block diagram of one embodiment of a resonant frequency detection circuit according to this disclosure. As shown in FIG. 27, piezoelectric element (or piezo) 540 is coupled to an isolation impedance 2740, sampling FET 2750, capacitor 2760 and ADC 2720.

Sampling FET 2750 may be utilized to maintain the circuit in its dynamic range, thereby ensuring that the circuit operates in its linear, operable range. Isolation impedance 2740 is configurable to allow the drive signal (e.g., a 45 V drive signal) to be isolated from point A between isolation impedance 2740 and sampling FET 2750, capacitor 2760 and ADC 2720, so that point A cannot go above a particular limiting voltage (e.g., 3 V), in order to protect other components including ADC 2720.

Thus, the drive signal may range up to a signal voltage SV (e.g., about 45 V), as shown by the square wave input to piezo 540. Following a drive signal a TEP signal (depicted by a decaying wave) is emitted by the piezo 540. This signal passes through the isolation impedance to present a reduced amplitude version at point A. The voltage at voltage-limiting or isolation point A, as defined between isolation impedance 2740 and one or more of sampling FET 2750, capacitor 2750 and ADC 2720, has a maximum value MV (e.g., about 3 V). The time-energy product (TEP) signal is also shown, for piezoelectric resonance detection and characterization, as disclosed herein, and as described in the incorporated references. In order to be able to analyze discrete samples of the drive signal, the sampling FET 2750 is selectively turned off or on. From the above discussion, it will be appreciated that the TEP (Time-Energy Product) is the energy stored in the piezoelectric/membrane combination i.e. in the fluid filled ejector mechanism. Depending on the quality factor of the mode, more or less energy will be stored. The less dampening in the mode, the longer the system will continue to move after the drive signal has terminated. This means that the piezoelectric will output a signal after the drive signal is turned off (based on the loading circuit). Thus, during this ring-down time the signal generated will have a maximum amplitude and ringing time based on the Quality factor of the mode and whether it is a piezoelectric mode or a system (membrane) mode. The TEP signal charges the capacitor and is used by the analog to digital converter (ADC) 2720 to determine the ring-down time. Thus the TEP signal can be correlated or integrated to determine the energy storage in the mode.

Figure 28:
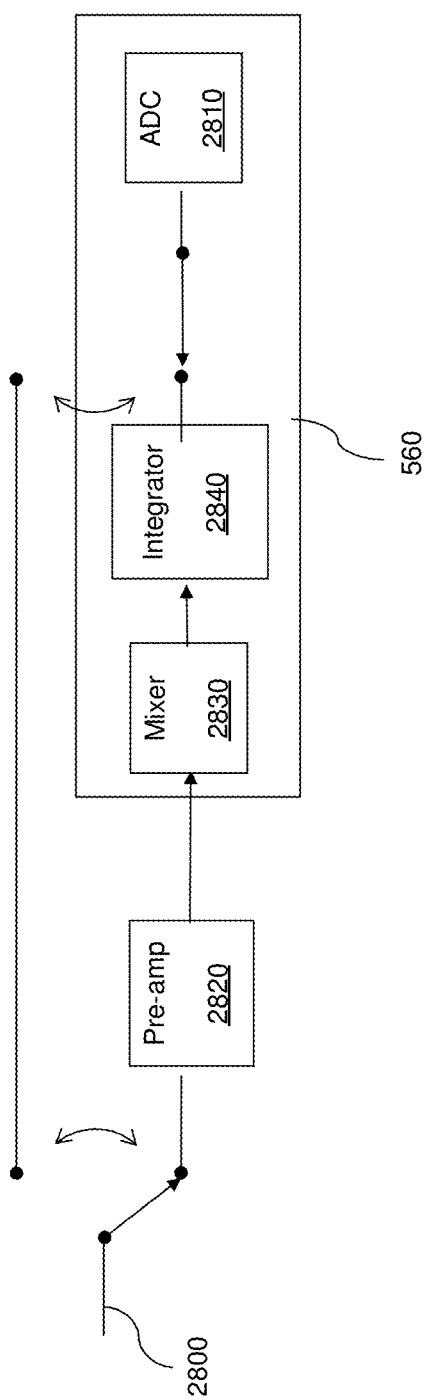
FIG. 28 is a block diagram of one embodiment of a bypass for a resonance detection and control circuit according to the present disclosure.

FIG. 28 shows selected components of one embodiment of a resonance detection and control circuit 560 with an optional bypass switch 2800. The bypass switch 2800 may be used to select between input directly to the ADC 2810 or first through a pre-amplifier 2820, mixer 2830, and integrator 2840. When the full resonance detection and control circuit 560 is enabled, the NCO or oscillator is turned on in single frequency mode and swept in frequency. If the output of the resonance detection and control circuit 2810 is greater than a defined value or a maximum, it defines a resonance. The strength of the resonance is determined by the amplitude of the resonance detection and control circuit 2810 output. The boost converter (not shown) is controlled by a gated oscillator using the Analog to Digital Convertor (ADC) output to sample the output voltage. In the case of inductors added to the full bridge output, the piezoelectric actuator voltage is monitored in order to control the boost voltage output. The boost voltage output is further amplified by the resonant converter formed by the piezo and inductors without increasing the input current as opposed to conventional resonant matching which results in real power transfer rather than energy storage in the resonant elements. In this embodiment, the measurement circuit is implemented as a resistor divider and a peak detector, which are used to monitor the voltage in the tank, both for voltage control, and also during Quality factor sweeps with electrically resonant tanks. This feeds the ADC. TEP cannot be used with a resonant converter because the electrical resonance is orders of magnitude stronger.

In another embodiment, with reference to FIG. 18 A, a resonance detection and control circuit operates such that the N-channel device, T7, is turned on throughout the full bridge drive cycle in order to ground the measurement node while the high drive voltages applied to the piezoelectric actuator (ejector) are activated (to protect the ADC). When the high voltage drive signal stops, the N-channel devices T5 and T6 are enabled (turned on) to temporarily short the piezoelectric actuator. This both drains off the high drive voltage to the piezoelectric actuator (that masks piezoelectric movement voltage) and allows the voltage induced by the movement of the actuator to be unmasked and directed to the ADC node. The N-channel device T5 is on for the entirety of the measurement cycle, while T6 is disabled (turned off) after a short amount of time (1 ns-50 us) to force the piezoelectric movement to output a voltage to the ADC node. Without the short of T6, the energy is not necessarily directed to the ADC measurement port. When T6 is disabled, T7 is also disabled, allowing the output of the piezoelectric to be voltage divided by R3/(R2+R3) and integrated by the capacitance from C1 and T7. The ADC samples the voltage at a prescribed time after T7 is disabled, usually between 1 µs and 500 µs. The transistor T7 may be switched at the rate of the original drive signal to correlate with specific frequencies.

Figure 29:
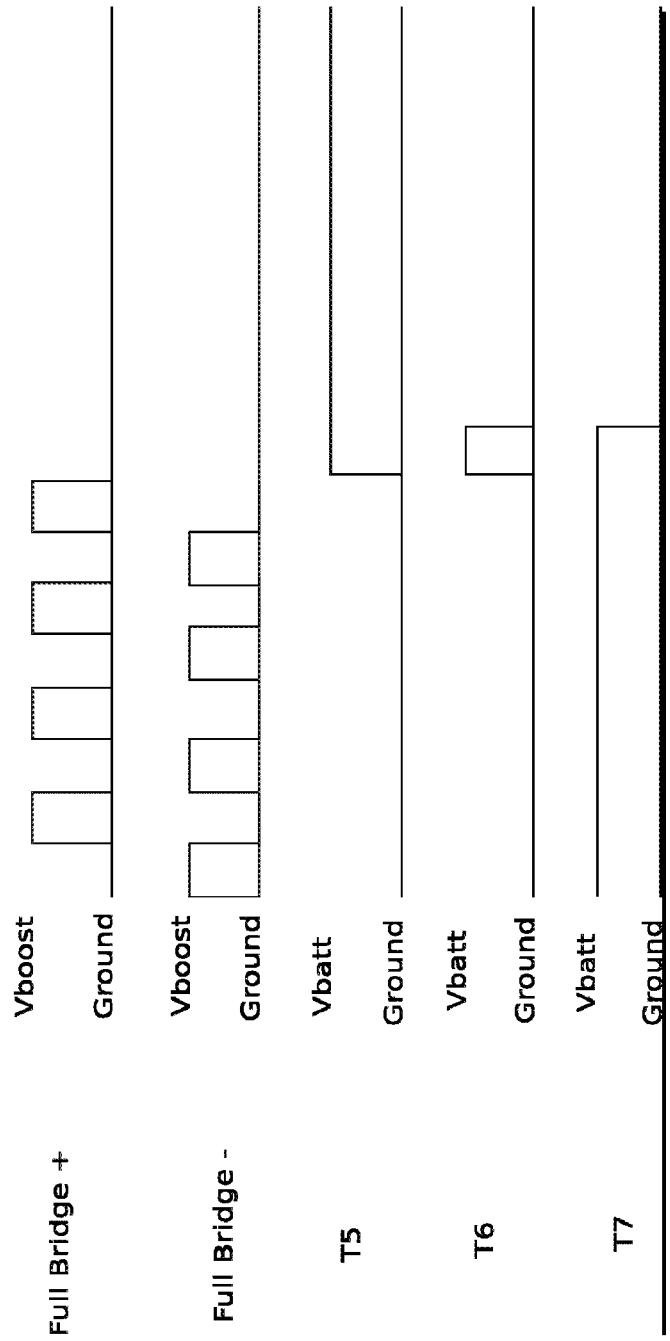
FIG. 29 shows driver signals and resonance detection and control circuit signals according to one embodiment of the present disclosure.
Figure 30:
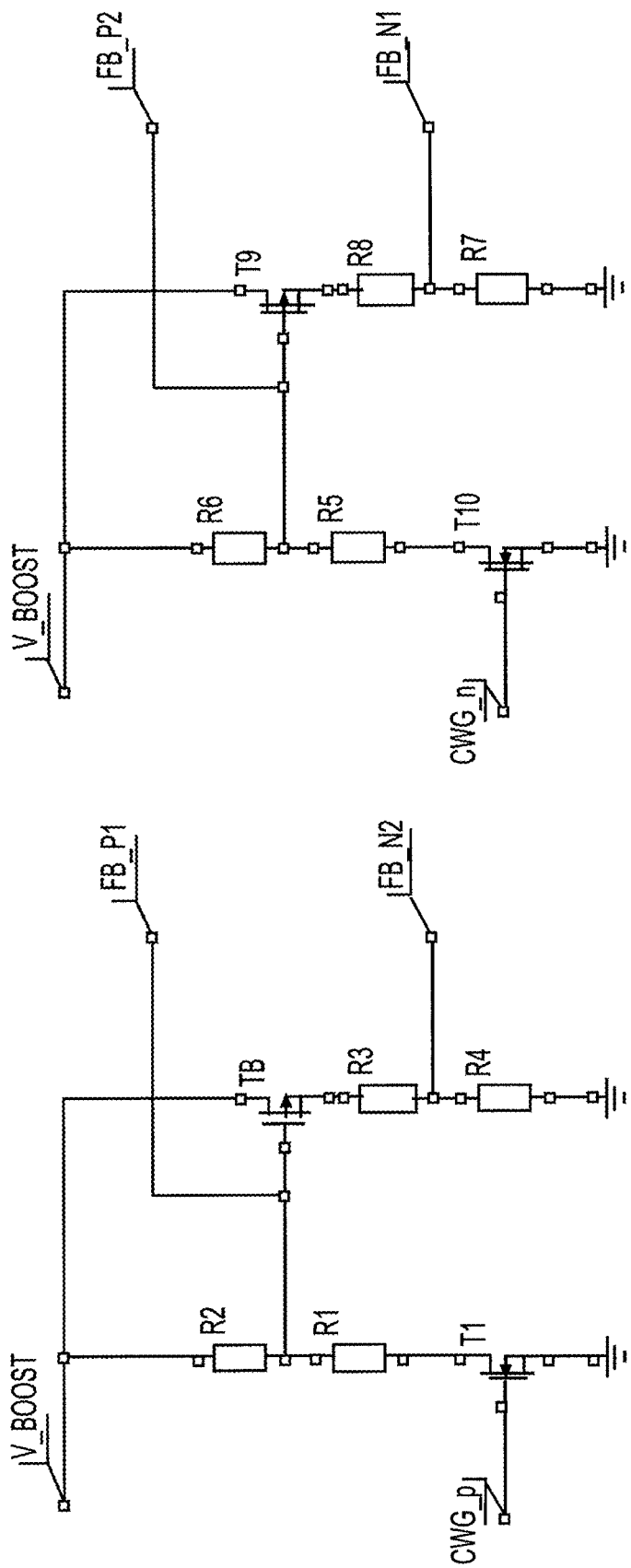
FIG. 30 is a schematic circuit diagram of one embodiment of a level shifting driver to take complementary waveform generator output to drive levels necessary for full bridge operation according to the present disclosure.
Figure 31:
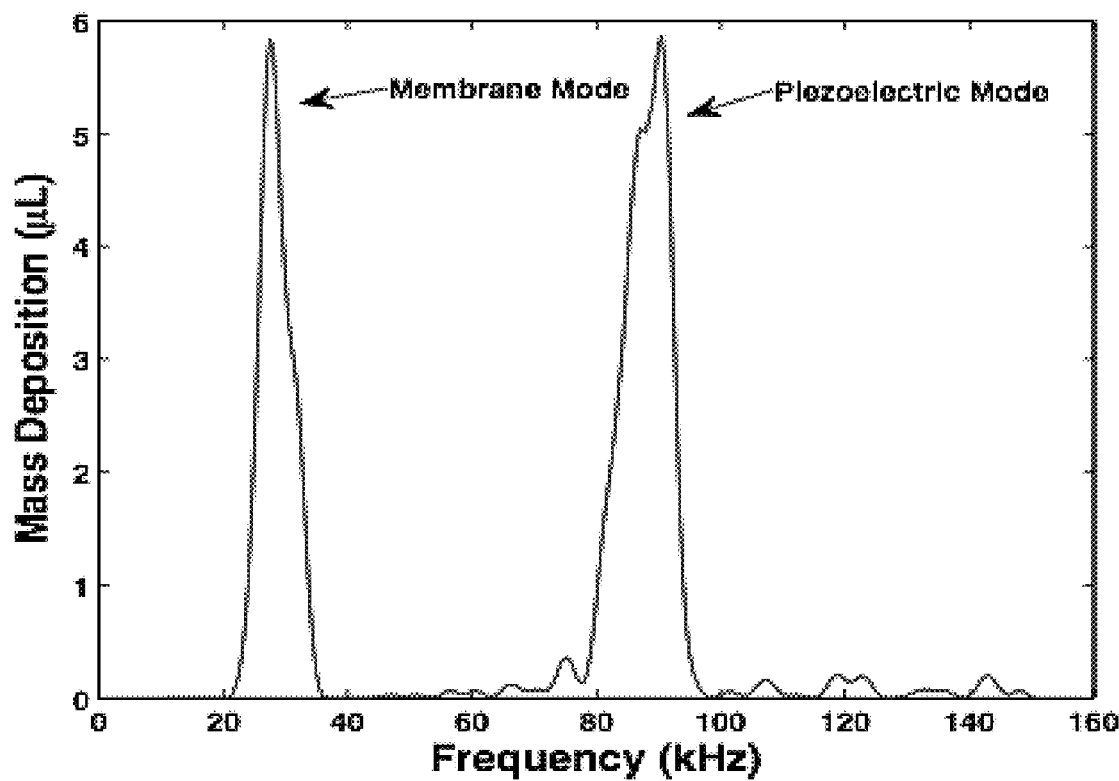
FIG. 31 is a Mass Deposition vs. Frequency waveform for one implementation of the present disclosure.
Figure 32:
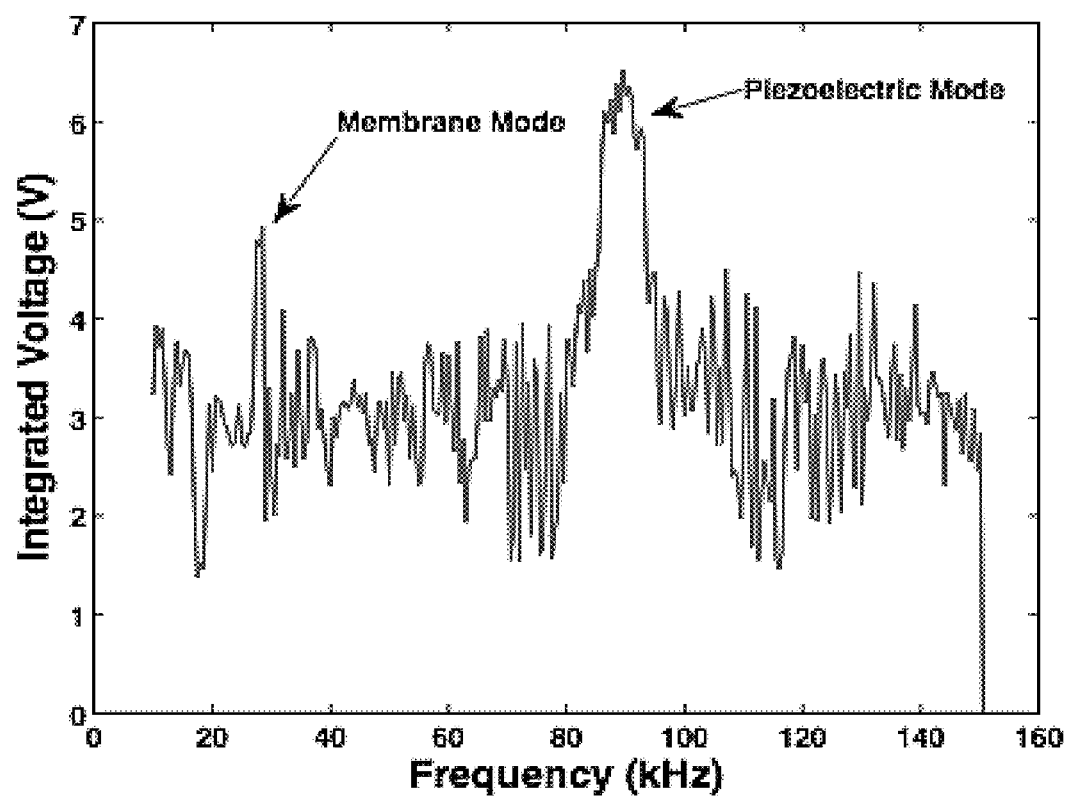
FIG. 32 is an Integrated Voltage vs. Frequency for a resonance measurement output according to one implementation of the present disclosure.

Examples of drive signals are shown in FIG. 29, for both sides of the piezoelectric actuator and the corresponding signals applied to T5, T6, and T7. This sequence and ADC measurement may be done at defined frequency steps from 1 Hz to 150 MHz, e.g., 150 kHz, 10 MHz, etc. The largest integration value may be chosen as the spray frequency, although mathematical corrections related to specific spray dynamics may be applied (such as increase in ejector velocity with frequency, and piezoelectric vs. membrane mode displacement) and voltage coupling coefficients can be applied to make the mechanism more accurate.

In one embodiment, an electromechanical system according to the present disclosure may determine the frequency and quality factor of its resonances. In another embodiment, an electromechanical system as described herein may permit tracking of its resonances as they change due to mechanical loading, applied drive signal, and ambient temperature, or any combination thereof. Such aspects and resonance tracking may be accomplished without a feedback electrode, the use of which may impact droplet generation, efficiency and mass deposition on a desired target in a fluid ejection system. Additional benefits in specific applications may also be realized in accordance with the present disclosure.

For instance, in certain embodiments, the resonance tracking described herein may be utilized in any of the droplet generator devices of the disclosure. The droplet generator device can thus be made to bring itself back into resonance mode. Short duration drives at different frequencies are used to map the resonance amplitude across a range of frequencies. (This range of frequencies can be calculated by determining the maximum statistical difference between parts in fabrication/manufacturing.) The output after a spray may be compared to the original resonance mapping of the droplet generator device to fix any drift and for spray verification. In such a use, resonance tracking can be accomplished without a feedback electrode, which would have the effect of reducing mass deposition in the fluid ejection mechanism as described therein.

A charge isolated ejector (double layer flex circuit, 50 μm SS316L annulus, gold coated 40×160, 57 hole ejector element, 19 mm OD×13 mm ID 250 μm thick PZT) was driven to eject at frequencies from 10 kHz to 150 kHz. Mass deposition and electrical waveforms were recorded at each frequency at the same instant.

The level shifting driver circuit shown in FIG. 30 is driven by a MICROCHIP PIC16LF1503 from the internal complementary waveform generator. The level shifting driver drives the Full Bridge which actuates the piezoelectric element. The MICROCHIP PIC16LF1503 waits 10 seconds between each frequency to allow the OHAUS PA214 scale to reach equilibrium during mass deposition measurement. The Microchip PIC16LF1503 also provides all necessary driver signals (for T5-T7 referenced in FIG. 18A). Electrical signals are recorded on an AGILIENT 3014A oscilloscope and are subsequently processed in MATLAB by integrating the signal up to the measurement time of the PIC16LF1503 to demonstrate operation of resonance measurement and control (Digitally implementing various analog filters to determine optimum circuit components).

The integrated piezoelectric output signal, sampled 30 μs from the time when T7 is disabled, closely tracks the movement and mass deposition of the mechanism across frequency, as shown in FIG. 31 and FIG. 32. FIG. 31 shows the mass deposition in membrane mode and piezoelectric mode, while FIG. 32 shows the resonance measurement output. Output is stronger for piezoelectric modes (where only a piezoelectric actuator is involved) as opposed to membrane mode (where the actuator is coupled to a membrane, which may take the form of a fluid-filled ejector mechanism), and must be corrected using a movement to voltage coupling parameter for both the piezoelectric modes and membrane modes. Coupling parameters are determined by sinusoidal excitation of the actuator and measurement of movement using the Digital Holographic Microscopy (DHM). Coupling parameters simply scale results in a given frequency region (weight them) to provide optimum ejection. Furthermore, frequency and amplitude of movement can be used to calculate ejector velocities which can be used to determine optimum spray. The circuit may be used without correction if operation is limited to either piezoelectric or membrane modes, i.e. mixed operation is not allowed. The circuit tracks only the displacement of the system, which is loosely correlated to spray. Accurate spray computation requires coupling constants and velocity computation. The resonance measurement and control system can be configured in either manner.

While specific embodiments have been discussed above to determine and provide resonance signals to an actuator (piezoelectric mode) or to an ejector mechanism (membrane mode), it will be understood by those skilled in the art that various changes may be made and equivalents may be substituted for elements thereof, without departing from the spirit and scope of the invention. In addition, modifications may be made to adapt the teachings of the invention to particular situations and materials, without departing from the essential scope thereof.

While the above discussion discussed the value of determining and using resonant frequencies in driving the piezoelectric actuator, the particular drive signal or drive waveform also impacts the stability and repeatability of the ejector device by influencing beading and wetting on the front or anterior surface of the ejector mechanism.

FIG. 33 is a schematic circuit diagram of one embodiment of a circuit 3300 for implementing a droplet generation system in any of configurations described above. In this particular embodiment, circuit 3300 is configured for a gated oscillator boost implementation of the driver, e.g., driver 520, as described herein, and as disclosed in the incorporated references.

As shown in FIG. 33, circuit 3300 includes one or more additional electronic components, including, but not limited to, switching components S1-S4, capacitors C1-C4, diode D1, comparator U1, inverter U3, pulse width modulation circuit (PWM), which includes PW envelope generator V2, invertors U5-U6, logical NAND gates U2 and U4, and NOR gate U8, controlling the gate of transistor Q1 to control the comparator U1 feeding the PWM circuit, and to control the voltage to the power rail of the switches S1-S4. These additional components are utilized to generate delay, phase shifts, gating, summing, signal boost, and other power and signal conditioning effects to generate pulse-width modulated PWM signals for driving actuator, e.g., actuator 540 discussed above. The mechanical load, e.g., load 550, may include, for example, an actuator attached to a fluid-loaded ejector plate, or to an ejector plate coupled to a fluid-loaded generator plate based on single-tone or multi-tone numerically controlled oscillator (NCO) signals, as described above.

FIGS. 34A, B are plots of a fluid relaxation waveform versus time using one embodiment of a device of this disclosure. The drive signal voltage is delivered in two bursts, from approximately 25 ms to just over 25.5 ms on the time axis (horizontal), and from approximately 27.5 ms to just over 28 ms on the time axis.

Figure 34A:
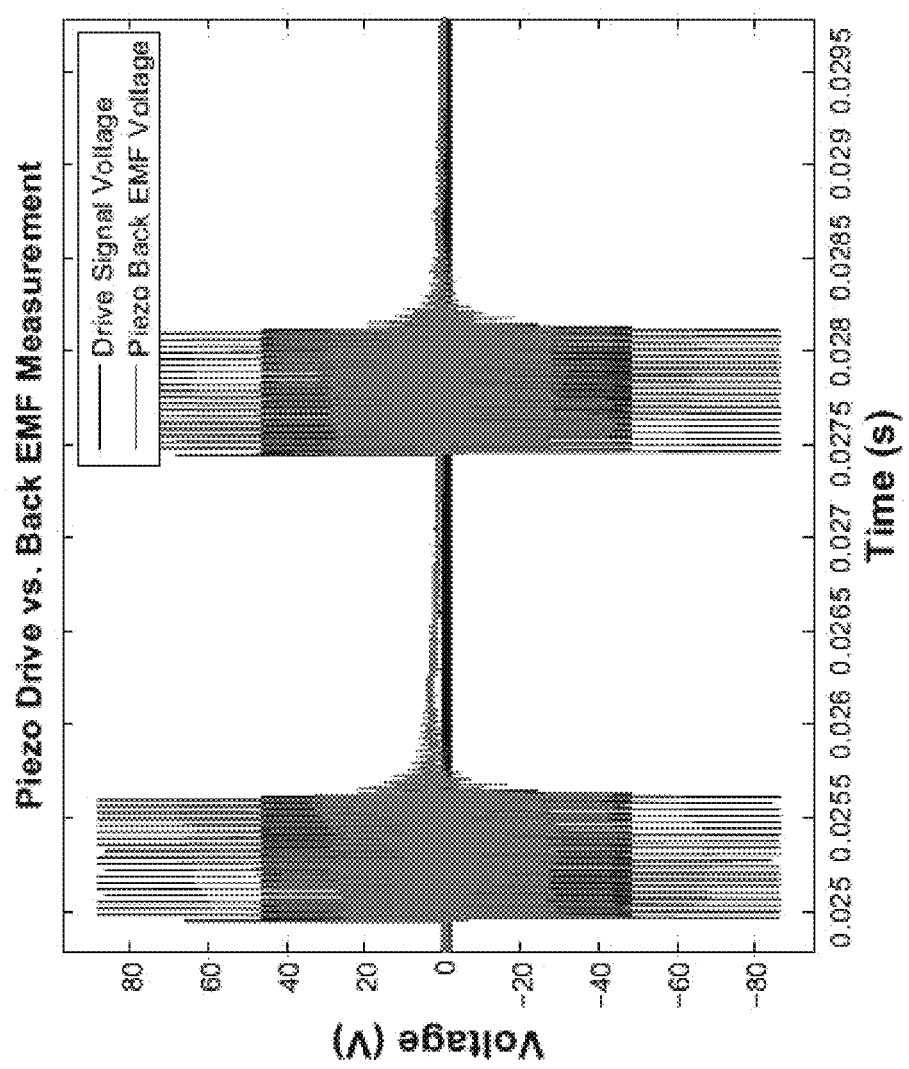
FIG. 34A is a plot of an exemplary fluid relaxation waveform.

As shown in FIG. 34A, the back EMF signal follows the drive signal and then decays with a characteristic time scale of a few tenths of a millisecond, for example with an exponential decay constant in a range of about 0.1-0.5 ms, or about 0.2-0.3 ms. As a result, there may be fluid ejection from the device after the drive signal is terminated. There may also be a residual bias that decays on a somewhat longer time scale of about 1 ms or more, as shown by the separation between the drive signal voltage (at zero) and the back EMF signal between the first and second burst.

Figure 34B:
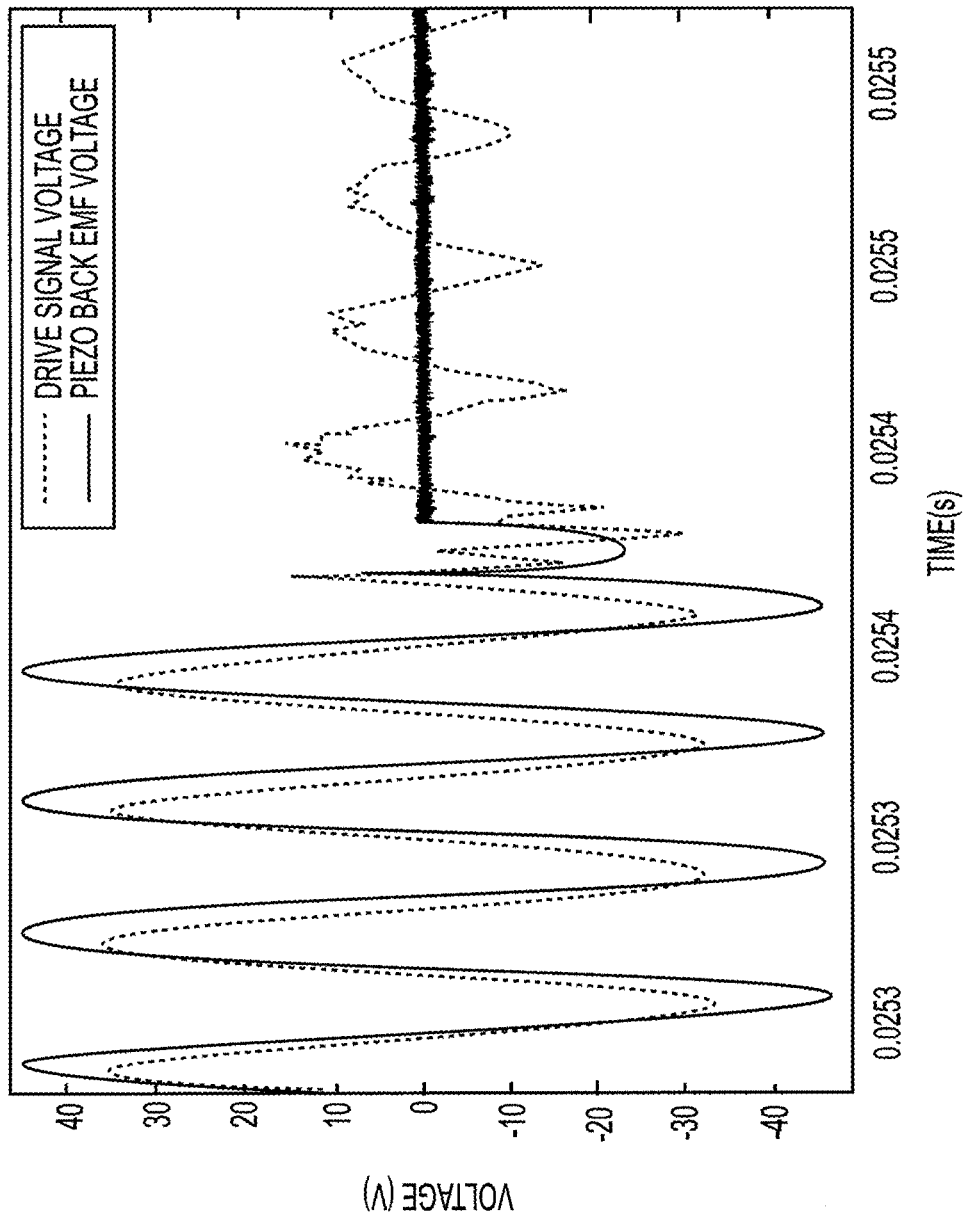
FIG. 34B is an expanded view of the fluid relaxation waveform in FIG. 34A.

FIG. 34B is an expanded view of the fluid relaxation waveform plot in FIG. 34A, showing the back EMF ring-down after termination of the drive signal. As shown in FIG. 34B, there may be substantial motion of the ejector plate after termination of the drive signal, leading to continued droplet formation as described above. There is also a phase shift between the drive signal and back EMF, which may cause the fluid-loaded ejector plate motion to lag (or in this case, lead) the drive signal waveform Prior to excitation by the drive waveform, the ejector plate assembly starts from a resting state, in which there is no mechanical movement. As the electrical drive signal is applied to induce movement, there is a finite time lag before droplets are ejected. Where there is more than one opening in the droplet generator, each opening may have a different characteristic time to reach the necessary velocity for fluid ejection, depending on the oscillation mode (or modes) and corresponding resonance frequency (or frequencies). Thus, the characteristic lead time before droplet formation is a function of drive voltage, frequency, aperture position, and eigenmode shape, as defined by the oscillating ejector plate or droplet generator.

Where fluid is expressed through an opening before reaching sufficient velocity for droplet generation, beading may occur, further delaying the onset of droplet formation and decreasing mass deposition and fluid delivery. Fluid beading may also increase the wetted ejector plate momentum, lengthening the characteristic ring-down time after termination of the drive signal.

To reduce beading, the ejector system may be driven for a selected time, herein also referred to as a continuous drive length. In particular, the time may be selected for the ejector plate to reach sufficient velocity to eject one (or more) droplets from one or more openings positioned in various locations on the drop generator, or in an ejection region in a central area of the ejector plate, depending on the eigenmodes of the particular structure. According to one aspect of the present disclosure the drive signal may be selected to operate in a drop on demand mode. In this mode the actuator is driven for a certain number of cycles determined by the fluid properties, then driving stops to allow the system to relax, whereafter the continuous drive length sequence is repeated. This may be performed the desired number of times to achieve the desired mass transfer of fluid. Droplet on demand mode has the effect of reducing fluid beading and thus reducing momentum of the ejector mechanism, thereby increasing mass transfer to the droplet stream and lowering ring-down time after the drive signal is cut off. The continuous drive length is also selected depending on desired dosage, fluid viscosity, oscillation mode and ejector configuration, and other parameters, and may vary from about 1 ms or less to about 10 ms or more, or in a range of about 1-2 ms, or less, or about 2-5 ms, or more.

Fluid beading may be reduced or suppressed by driving the piezoelectric actuator for a selected number of cycles, sufficient for one or more droplets to be ejected from one or more openings. The number of cycles is also selected based on parameters including, but not limited to, desired dosage, fluid viscosity, oscillation mode and ejector configuration, for example in a range of about 1 cycle to about 10 cycles, for example, in the range of about 2-5 cycles. Alternatively, the actuator 1604 may be driven for 10 cycles or more, for example about 10-20 cycles, or in a range of about 10-60 cycles or more, for example about 10, 20, 30, 40, 50 or 60 cycles.

In other applications, continuous fluid ejection via jetting is necessary in order to deliver relatively larger volumes of liquid (for example, in the range of 0.5-30 µl or more). Ejecting in continuous mode (that is, with a continuous drive signal), however, can also result in beading. Without intending to be limited by any particular theory, beading may arise, for example, due to chaotic jets, satellite droplet recapture, induction, and charge effects, as described above. Where a fluid bead forms over an opening, moreover, the bad fluid volume may tend to increase over additional cycles of the actuator, for example via pumping action and related hydrodynamic effects. Continuous pumping may eventually lead to wetting on the distal surface of the oscillating ejector plate (or droplet generator plate), resulting in increased momentum, Coulomb attraction, and related mechanical and electromechanical effects.

The piezoelectric actuator may also be driven for a selected number of cycles followed by a period between drive signals, which may be characterized as a relaxation time or relaxation time period. The cessation of the oscillating drive voltage during the relaxation time period results in decay of the fluid filled ejector plate oscillations, over the characteristic ring-down time. The ring-down time depends, for example, on the magnitude of the ejector plate and actuator motion, and the mass of the fluid-wetted ejector system. Depending on the application, a relaxation time period selected based on the ring-down time may reduce beading. This intermittent driving of the actuator will be referred to herein as pulsed operation mode. The mass ejection rate (per unit time) may be reduced in pulsed operation mode, depending on the drive pulse width and relaxation time, for example by about one third, about one half, or about two thirds, as compared to a continuous jetting mode of operation.

In some embodiments, movement of the piezoelectric actuator after cessation of the drive signal may be monitored by detecting the back EMF (or back voltage) induced by residual motion of the piezoelectric actuator, which is mechanically coupled to the ejector plate. For example, the back EMF may be monitored via a metallization layer or electronic sensor electrically isolated from the actuator surface, as described above with respect to FIG. 4, or using a back-voltage induced on the drive signal circuit, for example via the drive electrodes or other conducting layer in direct contact with the actuator surface.

The ring-down time may thus be determined by the time required for the residual ejector plate and fluid oscillations to drop below a particular threshold, based on the back EMF signal. This has an advantage over fixed relaxation time applications, because the relaxation time is automatically adjusted for droplet formation, wetting, fluid viscosity, and other factors, based on their effect on the ring-down time of the fluid-wetted ejector assembly.

For example, the relaxation time may be defined by the time required for the back EMF voltage to become less than a selected fraction of its initial value, on cessation of the drive signal, for example about one tenth (10%) of the initial value. Alternatively, a different fraction may be selected, for example about one twentieth (5%) or less, or about one fifth (20%), about one third (33%), about half (50%), or a different ratio such as 1/e, or a multiple thereof. In additional applications, the relaxation time period may be selected based on an absolute threshold, for example based on correlating the back EMF signal to a selected magnitude or velocity of oscillation for the fluid-loaded ejector plate.

FIG. 35 is a set of amplitude vs. time plots of drive signal waveforms and corresponding piezoelectric movement waveforms, showing the phase shift between the two waveforms over time. Each of FIGS. 35A-D shows a different approach for generating ring-down damping signals in order to reduce residual motion after termination of the drive signal. A cancellation waveform may be generated in the form of an active damping or braking signal, based on the observed magnitude and phase of the ring-down feedback signal. For instance in FIG. 35A the cancellation signal simply comprises generating a half wave that is opposite or phase shifted by 180 degrees relative to the original wave signal. In FIG. 35B, in addition to generating an opposite half wave, the amplitude of the opposite waveform is adjusted. In FIG. 35C the opposite half wave is also time shifted to achieve an additional phase shift. In FIG. 35D a small pulse of opposite phase and higher frequency is generated.

Figure 33:
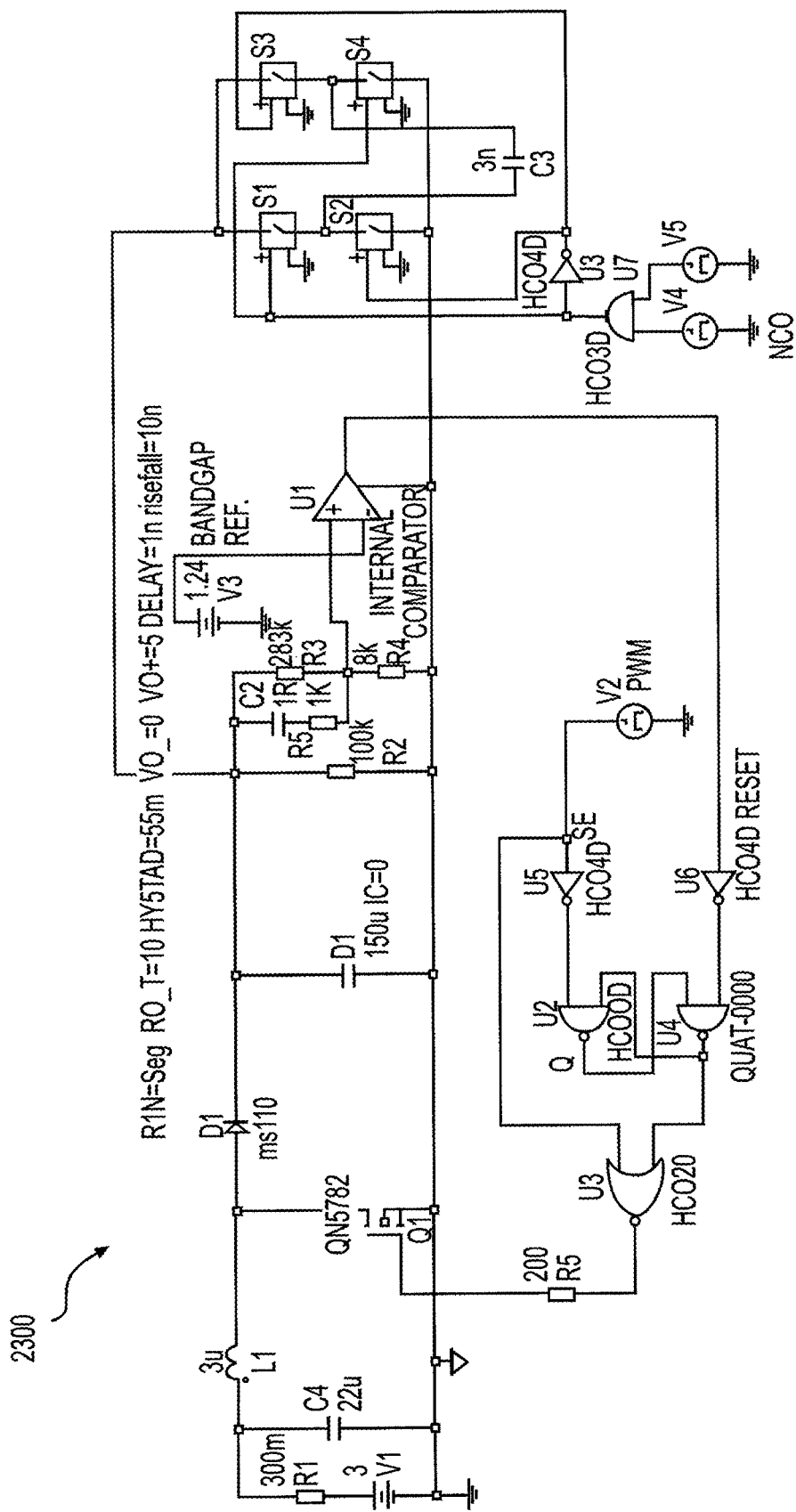
FIG. 33 is a schematic circuit diagram of one embodiment of a gated oscillator boost circuit for a driver system.
Figure 35A:
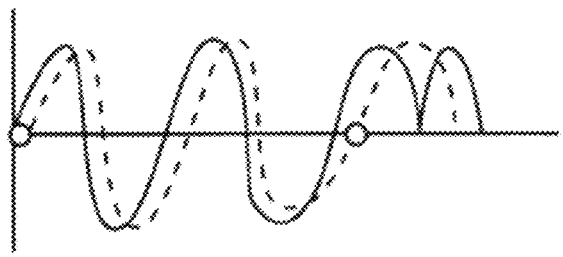
FIGS. 35A-35D are plots of examples of waveforms for ring-down damping.
Figure 35B:
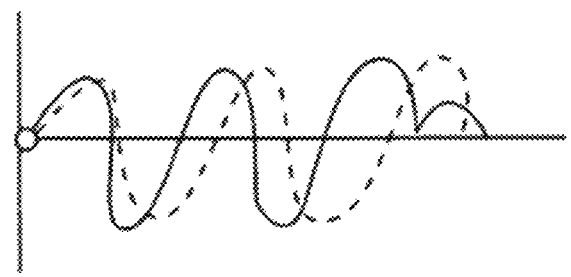
Figure 35C:
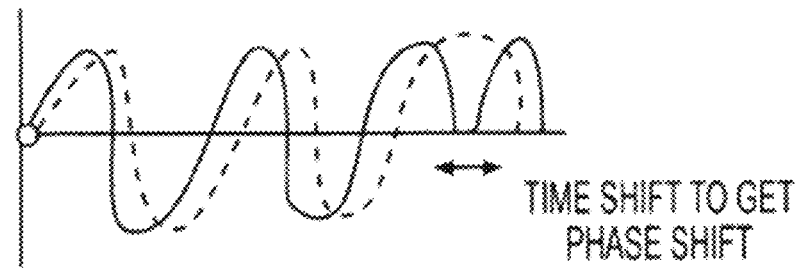
Figure 35D:
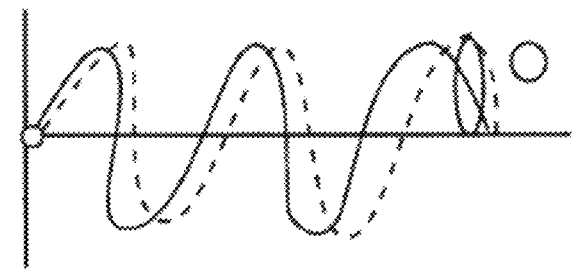

In general, the damping signal may be shifted in phase with respect to the drive signal, and reduced in magnitude (combination of FIGS. 35B and 35C). The magnitude is determined based on the magnitude of the back EMF signal, for example using an actuator sensor or back voltage in the drive circuit to generate ring-down or feedback signal 580 for resonance detection and control circuit 560, as shown in the piezoelectric systems above. Relaxation waveform and ring-down analyses are performed on the back EMF signal in order to generate a pulse width modulated (PWM) damping signal with appropriate magnitude and phase delay, for example as described above with respect to the various components of circuit 3300 of FIG. 33.

Depending on the application, the fluid oscillation on the drop generator may or may not occur at the same frequency as ring-down oscillation of the ejector plate itself. To the extent that this occurs, or in any case where multiple modes are excited, the back EMF signal will exhibit multiple frequencies and beating, as described below, and the active damping signal may be modified accordingly, for example by providing a combination of two or more different damping signals with different magnitude, phase and frequency.

Alternatively, a single short pulse or "chirp" signal may be utilized, based on the desired level of signal complexity and the required effect on the ring-down signal. For example, an "anti-phase" cancellation or damping signal may be applied, either based on the phase of the drive waveform itself, or based on the timing of the back EMF signal. In this application a smaller, opposite polarity damping signal may be provided with timing and amplitude selected to absorb or cancel residual oscillation energy and cause the actuator and load to brake in a manner similar to that of a vehicle.

Once any cancellation waveform or active damping (braking) signal is applied, a relaxation period may be utilized before applying another drive signal, as described above. Thus, the droplet generator may be driven in a pulsed or continuous pulsed mode, with or without damping waveforms following each pulse.

Droplets may also be generated in single-pulse mode, with fluid delivery over a single, finite drive waveform extending over a particular number of cycles, with or without a following active damping signal. In this single-pulse mode of operation, the relaxation time may be considered arbitrary, extending until an independently triggered (e.g., user-selected) activation of the device.

Thus, a range of different methods may be utilized to generate damping signals. For example, an equal amplitude waveform may be applied, with amplitude based on energy stored in the piezoelectric, and 180° phase shifting (opposite polarity) based on the phase of the back EMF signal. Alternatively, one or more unequal amplitude pulses may be applied with opposite polarity or a different phase shift, based on the available positive or negative supply voltages. In single-pulse or "chirp" damping waveforms, the energy in the waveform may be selected to match that of the fluid-loaded ejector plate and actuator system, and delivered with opposite polarity or other phase shift selected for maximum energy absorption, utilizing time-energy balancing to cancel the residual oscillations and reduce ring-down time.

In pulsed or "limited cycle" modes of operation, the actuator may be driven for a limited number of cycles, below the characteristic beading time of the ejector system, followed by a relaxation period based on the characteristic ring-down time, and repeated as necessary to reach the desired fluid dosage or mass deposition. While mass ejection per unit time is nominally reduced, as described above, this may be offset by the benefits of reduced beading. The relaxation or "dead" time between delivery pulses can be lowered by application of an appropriate damping signal.

In this mode, the droplet generator may be driven for a limited number of cycles below the characteristic beading time of the ejector plate system, followed by application of an anti-phase (opposite polarity) waveform, based on the corresponding phase of the back EMF signal. The amplitude and phase may be selected for energy balance, in order to absorb a substantial fraction of the residual oscillation energy in a single pulse, or the amplitude and phase may vary, as described above. The damping waveform or "braking" signal may be controlled to reduce the motion of the actuator and ejector plate membrane, followed by additional ring-down of the fluid itself, during which no new drive signal is applied.

The complete waveform thus includes a limited-cycle drive signal, followed by a damping signal and relaxation or dead time for fluid ring-down, and is repeated as necessary in order to achieve the desired fluid dosage or mass deposition. Based on the reduced ring-down time, as compared to a limited cycle drive without active damping or braking signal, this mode provides both a reduced beading and increased fluid delivery rate, as defined in terms of fluid mass per unit time.

EXAMPLES

Example 1

Ejector Mechanism. In this example, a symmetric (e.g., 21 mm diameter stainless steel) ejector plate 104 was utilized, with a pattern of openings 126 provided in a droplet generator 132 formed in the central region of ejector plate 104. A driver circuit 520 was used to generate the drive signals, with a resonance or feedback circuit 560, to measure the back EMF or feedback voltage signal from the (e.g., piezoelectric) actuator, and control the driver circuit to provide a damping signal after each drive waveform. Other techniques for generating different drive waveforms and damping signals are also contemplated, as described above, and as disclosed in the incorporated references.

The ejector mechanism was operated in contact with a fluid reservoir, and provided with a driver signal (e.g., sinusoidal or square wave) to pump fluid through the openings of the droplet generator and eject the fluid in the form of a droplet stream. Where a continuous drive signal may result in beading of the fluid, a short burst or limited-cycle time may be used, for example about 150 ms or less, about 100 ms or less, about 50 ms or less, or about 25 ms or less. An electrically isolated pad or back EMF sensor may be attached to the actuator in order to monitor motion of the ejector assembly with respect to the drive signal, and to provide a residual oscillation cancellation signal after termination of the drive signal, in order to reduce ring-down time and increase the net fluid delivery rate.

Example 2

Piezoelectric Relaxation and Fluid Relaxation. In this example, an actuator driven in a resonant mode will continue to oscillate after the drive signal ceases, for a given period defined by the relaxation time. Even as the motion of the actuator and ejector system is reduced, the membrane or droplet generator will continue to oscillate due to the additional energy in the fluid-loaded mechanism. Fluid beading will occur if the piezoelectric is driven before the fluid has been allowed to relax, and beading and fluid oscillations will increase over repeated cycles if the dead time between cycles is insufficient.

Figure 36:
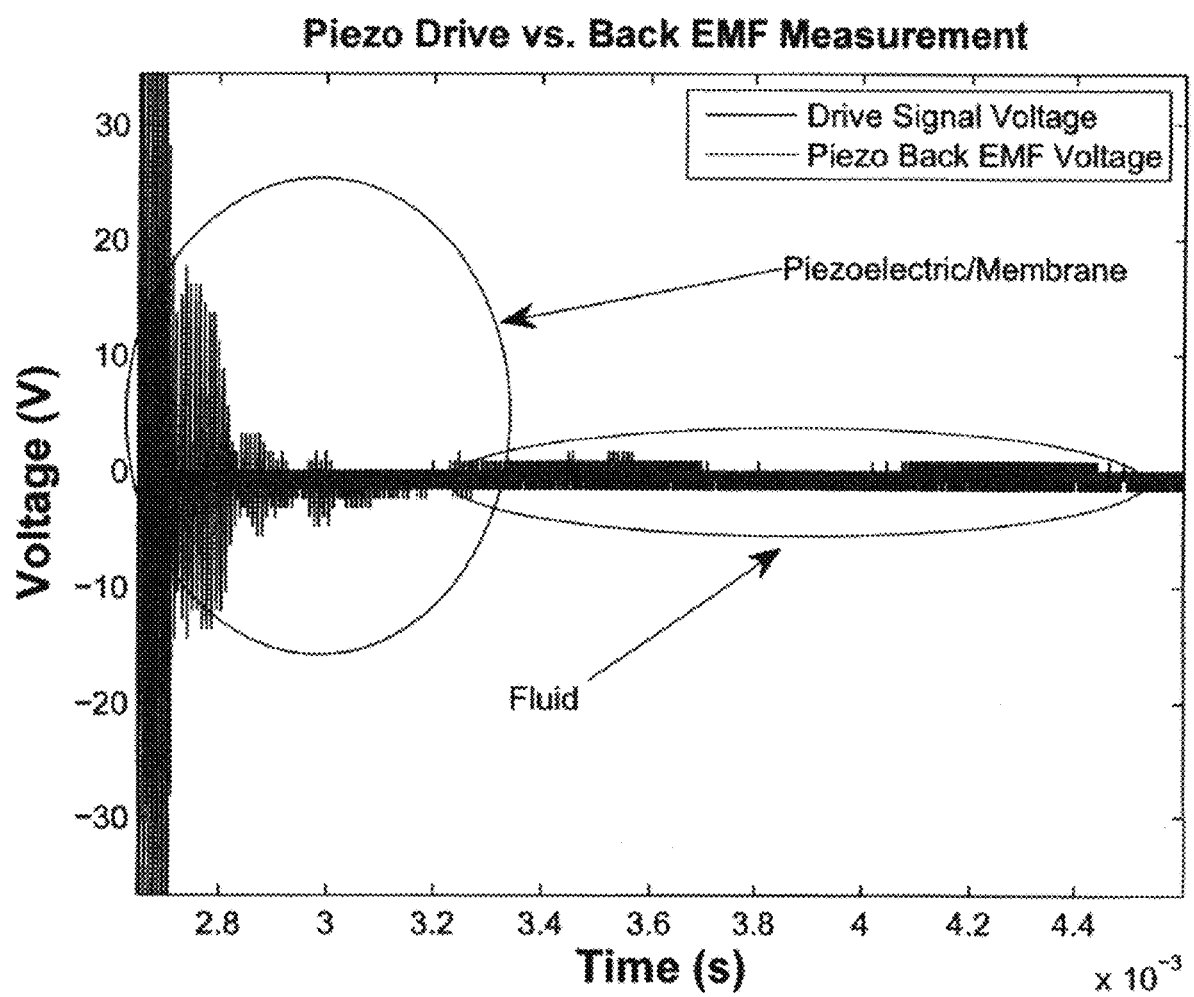
FIG. 36 is a plot of a relaxation waveform following removal of a drive signal.

FIG. 36 is a plot of a fluid relaxation waveform, illustrating these phenomena following removal of a drive signal. The piezoelectric back EMF voltage (vertical scale) is generated by movement of the piezoelectric actuator, and may be taken from an electrically isolated metal pad or back EMF sensor on top of the piezoelectric, as described above. The back EMF indicates that ring-down of the actuator assembly occurs on a time scale of a millisecond or so, for example about a half millisecond or less, or about 0.2-0.3 ms, depending on relative amplitude threshold. Over this relaxation period, the magnitude of oscillation may result in fluid ejection for a significant time period after the drive signal is terminated, for example up to 1-10 times the length of the drive signal waveform itself.

The fluid relaxation time of the fluid-filled mechanism (also referred to herein as the ejector mechanism) may be two to three times the ring-down time of the actuator itself, for example a millisecond or more, or in the range of about 1-2 ms or about 2-4 ms, depending on ejector design, fluid loading, hole size, and other factors. The fluid must be allowed to relax over this typically slower relaxation time, in order to prevent beading.

Figure 37:
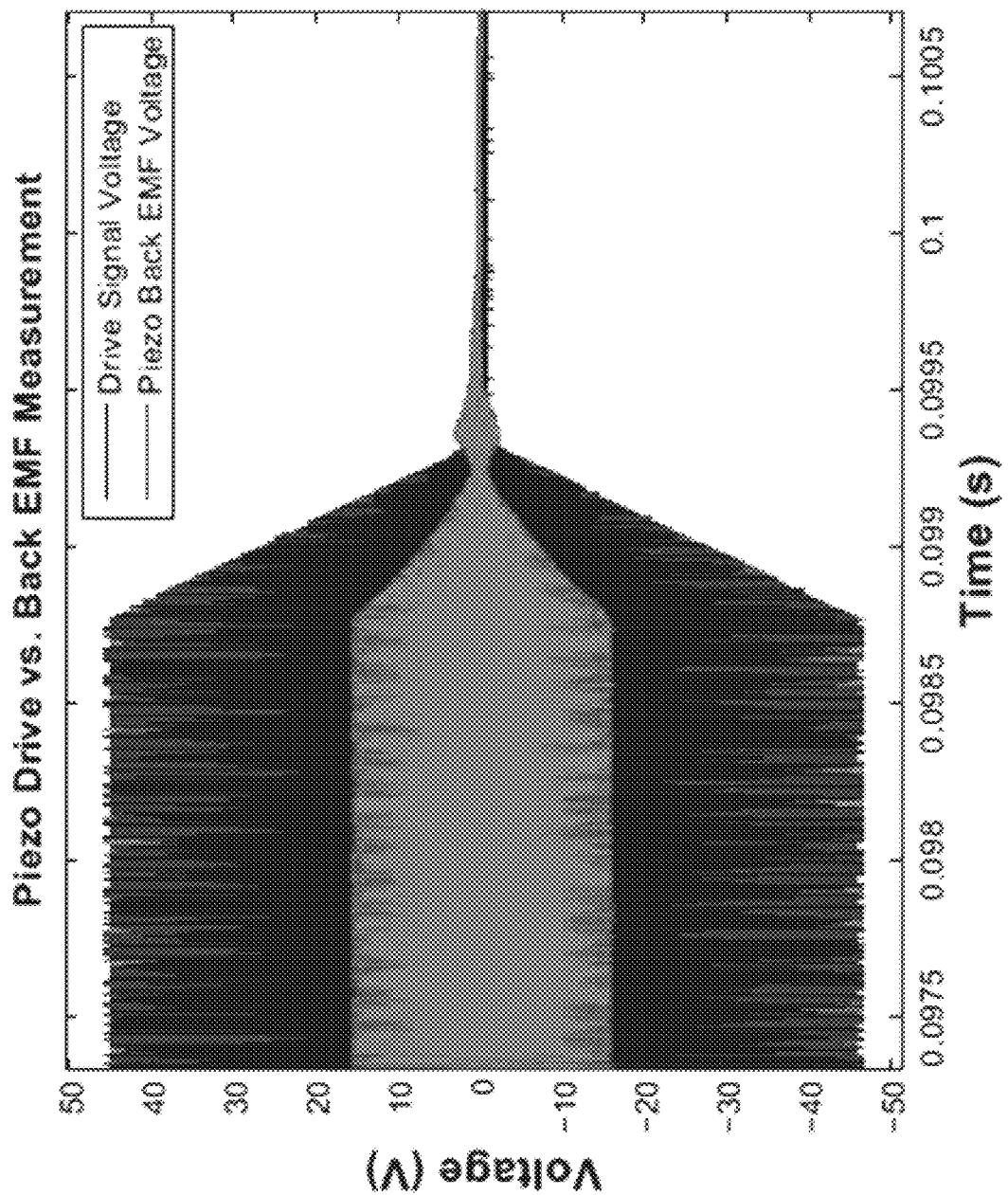
FIG. 37 is a plot of a relaxation waveform following a soft ramp down of the drive signal.

FIG. 37 is a plot of the fluid relaxation waveform following a soft ramp down, illustrating how the actuator assembly reacts when the drive signal is reduced linearly. The amplitude of the residual oscillation actually increases during the ramp-down period, and even after the drive signal reaches zero, due to energy storage in the actuator itself (for example, in the piezoelectric element, which may be a ceramic element). This energy is dissipated relatively slowly, for example over a few hundred cycles of the harmonic oscillation.

Figure 38A:
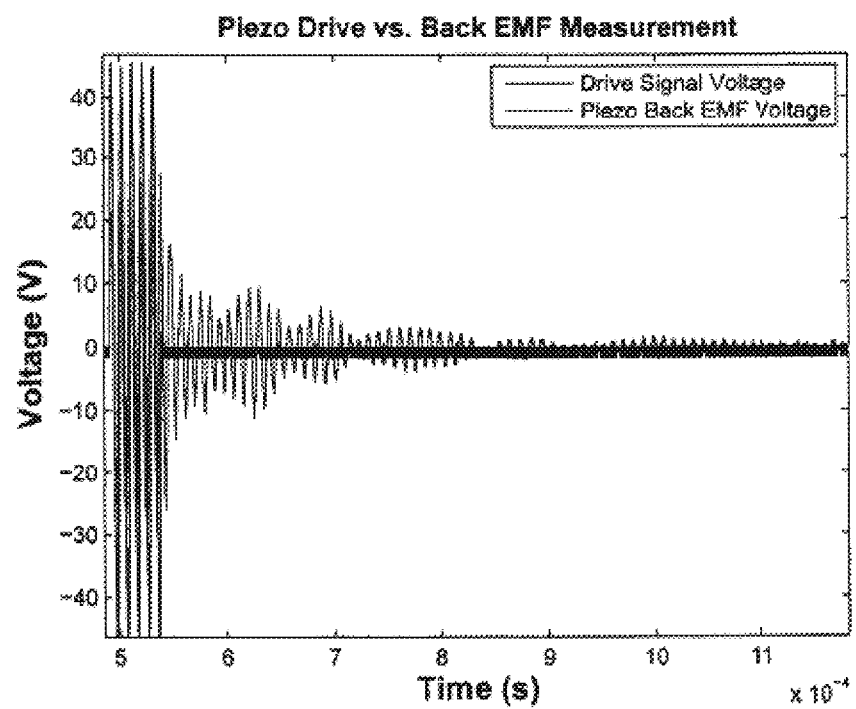
FIG. 38A is a plot of a relaxation waveform after a five-cycle excitation, showing harmonic production ("beating") of the ring-down signal.
Figure 38B:
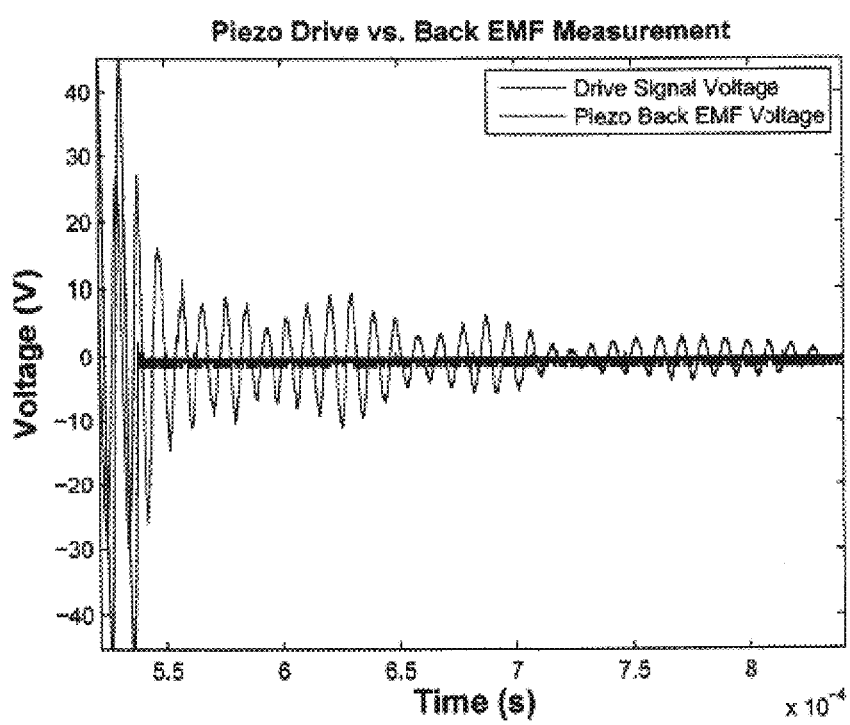
FIG. 38B is an expanded view of the relaxation waveform in FIG. 38A.

FIG. 38A is a plot of a relaxation waveform after a five-cycle excitation, where the drive signal was stopped abruptly. FIG. 38B is an expanded view of the relaxation waveform in FIG. 38A, showing harmonic production ("beating") in the ring-down signal. As shown in FIGS. 38A and 38B, not only does the actuator assembly continue moving after the drive signal is terminated, it can also generate relatively large harmonics and cross modulation products, which in turn may generate motion in resonant modes ("eigenmodes") having shapes favorable for beading.

Example 3

Cancellation Waveforms. In this example, cancellation waveforms were used to reduce such residual motion and ring-down time.

Figure 39A:
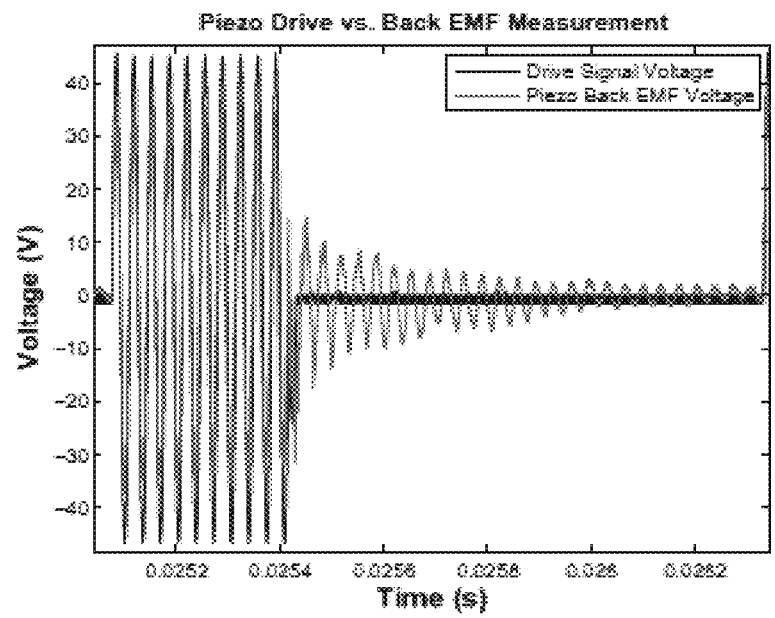
FIG. 39A is a plot of a fluid relaxation waveform after a ten-cycle excitation with an added damping signal, showing reduced relaxation time and harmonic production.
Figure 39B:
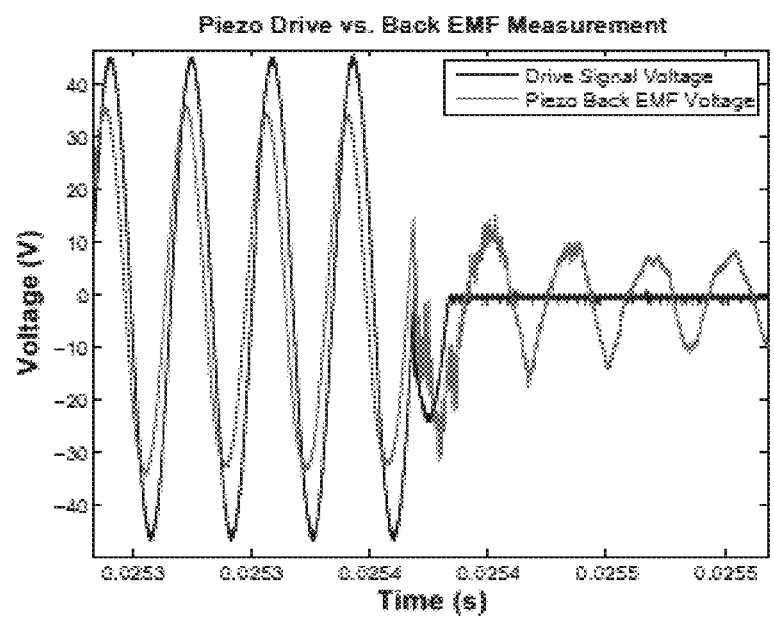
FIG. 39B is an expanded view of the relaxation waveform in FIG. 39A.

FIG. 39A is a plot of a fluid relaxation waveform after a ten-cycle excitation with an active damping waveform. FIG. 39B is an expanded view of the relaxation waveform in FIG. 39A, illustrating reduced relaxation time and harmonic production. As shown in FIGS. 39A and 39B, a damping signal is generated after the drive signal in order to absorb energy stored in the (piezoelectric) actuator. Although the ejector mechanism still continues to move after the damping signal is applied, the relaxation time is substantially lower, and harmonics and cross modulation products ("beats") are suppressed. This enables higher mass deposition rates, with reduced beading.

Figure 40:
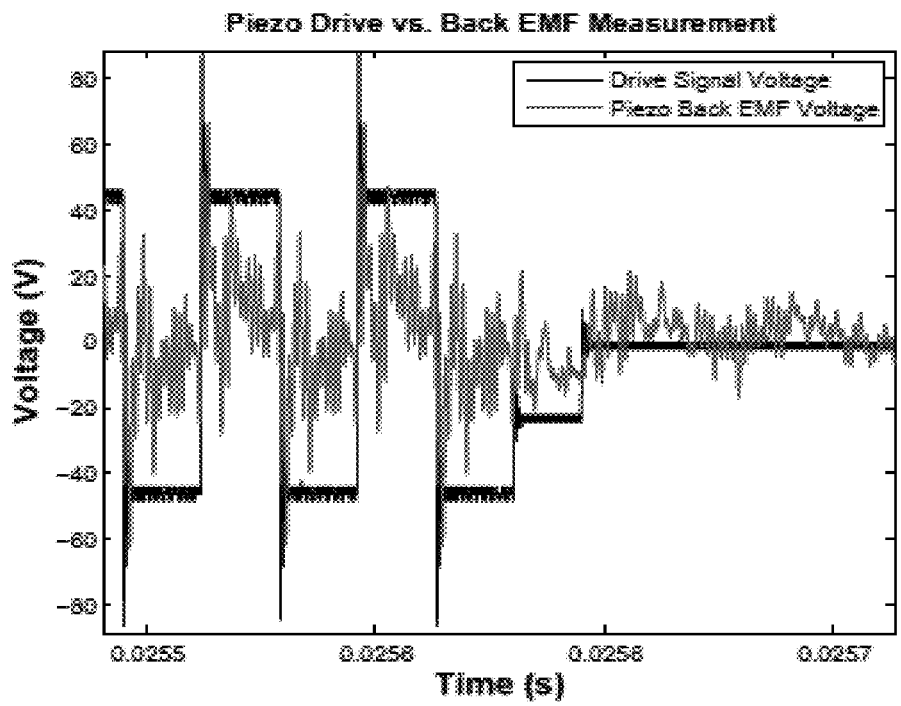
FIG. 40 is a plot of a relaxation waveform after a ten-cycle square wave excitation, with a damping signal.

FIG. 40 is a plot of a relaxation waveform after a ten-cycle square wave excitation, with active damping signal. As shown, both the drive signals and damping signals may be provided as substantially square waves.

Figure 41:
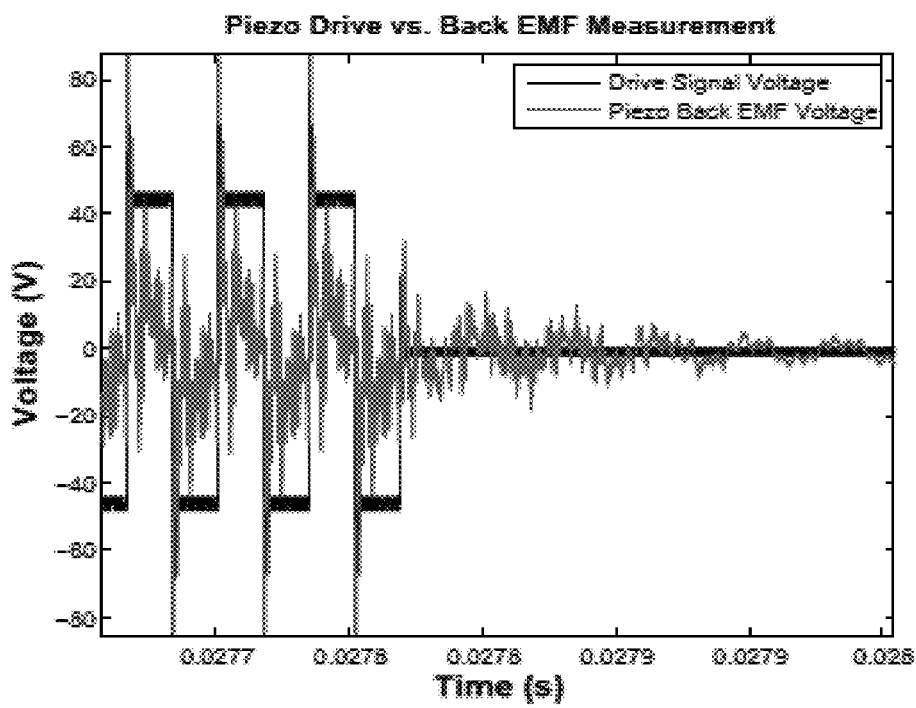
FIG. 41 is a plot of the relaxation waveform without a damping signal.

FIG. 41 is a plot illustrating the relaxation waveform for the same square wave excitation as used in FIG. 40, but without the damping signal.

Figure 42:
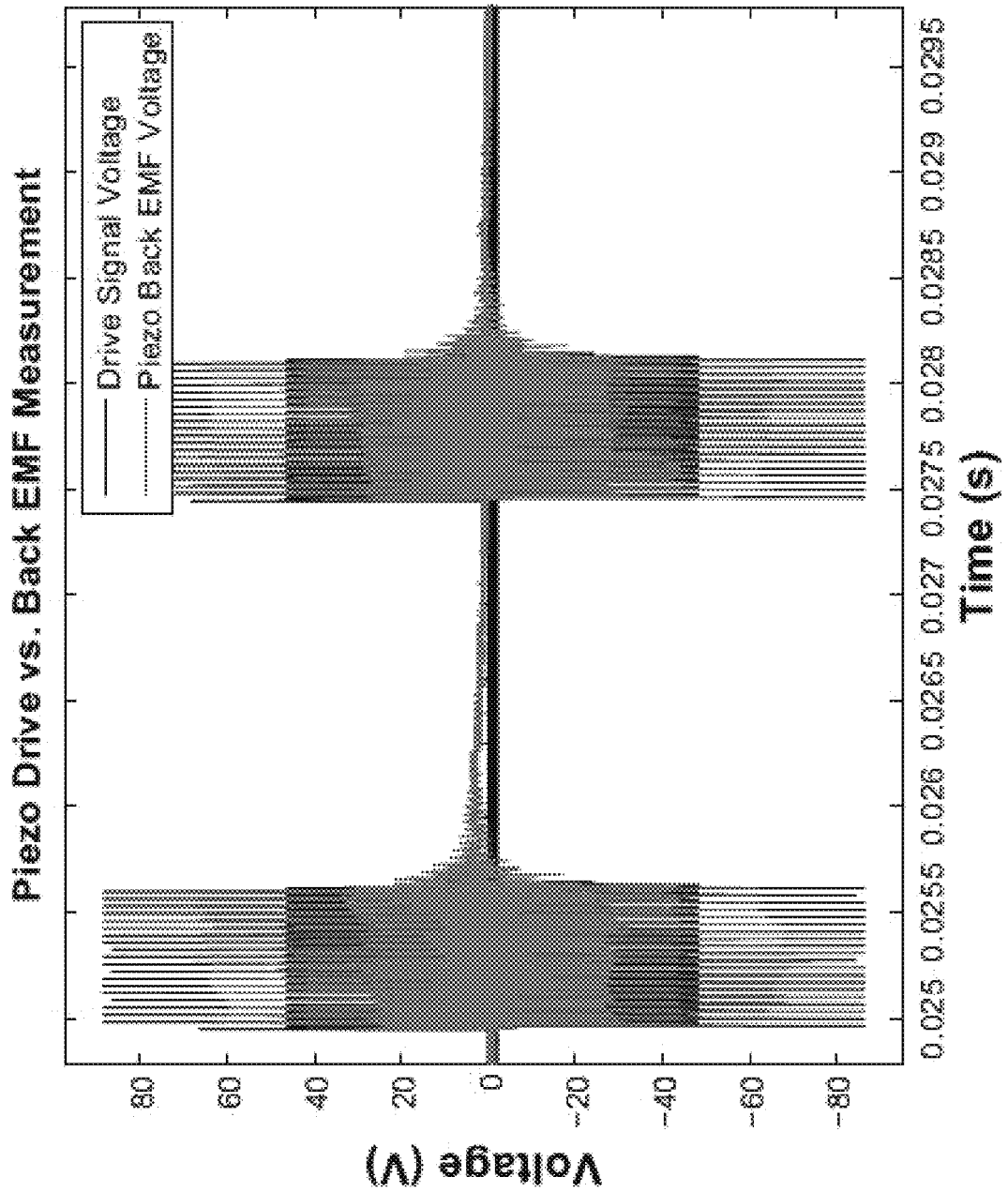
FIG. 42 is a plot of a relaxation waveform after two periods of a ten cycle square wave drive with damping signal and relaxation dead time.

FIG. 42 is a plot illustrating piezoelectric and fluid relaxation after two periods of a ten cycle square wave drive signal, with active damping signal and relaxation dead time. FIG. 42 shows two complete cycles of a fully assembled waveform, including a ten-cycle square wave drive signal, active damping signal for braking the piezoelectric actuator, and fluid relaxation (dead) time between repetitions.

Example 4

Beading of Fluid. This example utilized an ejector mechanism according to Example 1, above, in which beading was observed when the drive voltage is a simple sinusoidal or square wave. In this particular example, the drive signal waveform was 50 ms long.

In order to illustrate the benefits of relaxation time and an active damping signal, pictures were taken of an ejector at various stages, using two different viscosity liquids: distilled water and latanaprost, a topical medication used to reduce pressure inside the eye.

The distilled water and latanaprost images were captured with a high-speed (75,000 frames per second). For both fluids, the initial spray demonstrated a resonant mode of the generator plate, but not every hole ejected droplets. At 30% through the spray signal, continuous spraying without allowing for relaxation or "ring-down" resulted in the formation of large beads. At 60% through the spray signal, satellite droplets were created from chaotic spray collisions, which increased when there was no relaxation time, and level of beading and collisions increased as the spray continued. After the cycle was complete, large satellite droplets and beading were observed.

Example 5

Suppression of Beading and Satellite Droplet Formation. This example also utilized an ejector mechanism according to Example 1, above, but beading was suppressed utilizing one or more of the limited-cycle (repeated pulse), relaxation time, and active damping techniques described above.

Again water was compared to latanaprost but using active damping and relaxation. Again the initial spray images showed a resonant mode of the generator plate, but not every hole ejected fluid. This demonstrates that mode is non-trivial, and must be carefully determined in combination with the selected hole pattern and ejector plate geometry. At mid-cycle, droplets emerged from a majority of the ejection sites (openings) in a linear stream. There were fewer chaotic streams, thereby reducing satellite droplet formation, as compared to spray modes that show poor ejection. Beading was suppressed for both fluids in this example, and larger beads were substantially absent, or not observed. After the cycle was complete, large satellite droplets were significantly reduced, and substantially no beading was observed in the openings. Some satellite droplets could be observed, but they were substantially absent from the droplet formation sites.

In various additional examples, a method was provided for applying a first alternating voltage for one or more cycles to a piezoelectric actuator operable to oscillate an ejector mechanism so as to generate droplets of a fluid, stopping the first alternating voltage and applying a cancellation waveform or active damping signal, waiting for a first relaxation time period, applying a second alternating voltage for one or more cycles to said piezoelectric actuator, stopping the second alternating voltage and applying a cancellation waveform, and waiting for a second relaxation time period. The ejector mechanism may include an ejector plate having a proximal surface in contact with a fluid and one or more openings, with a piezoelectric actuator to oscillate the plate upon application of a drive voltage. The steps may be repeated one or more times to generate or deliver a selected volume of the fluid, for example in the form of a stream of droplets. The volume may be selected between about 5 μl and about 30 μl. The ejector mechanism may also be configured to eject the stream of droplets with an average ejected droplet diameter greater than about 15 microns.

The ejector may be configured for passivation and charge isolation with respect to the drive voltage. The cancellation waveform may be phase shifted with respect to the drive voltage and have amplitude substantially equal to or different from the drive voltage. The phase shift may be 180 degrees, so that the cancellation waveform has an opposite polarity with respect to one or both of the alternating drive voltages. Alternatively, the cancellation waveform may be substantially in phase with one or both of the alternating drive voltages, or have a time delay selected for a different phase shift with respect to one or both of the alternating voltages.

The cancellation waveform may also have unequal amplitude with respect to one or both of the alternating voltages, for example smaller amplitude than one or both of the alternating drive voltages. The cancellation waveform may also have amplitude selected for the waveform to have energy substantially equal to energy stored in the piezoelectric actuator.

Any one or more of the first and second alternating voltages and the cancellation waveform may be pulse width modulated, or comprise or consist essentially of a substantially square wave or a substantially sinusoidal wave. For example, both of the alternating voltages may be substantially sinusoidal, or substantially a square wave, or a combination of a sinusoidal and a square wave.

One or both of the relaxation time periods may be based on resonance monitoring of the actuator, for example by detecting a back EMF voltage. One or both relaxation time periods may be proportional to the number of cycles of one or both of the alternating voltages, and the number of cycles may be between one and about thirty. One or both relaxation time periods may also be determined when the back EMF voltage has a certain threshold value, for example as a fraction of an initial value, or one or both relaxation time periods may be proportional to the number of cycles of one or more of the alternating voltages.

Example 6

In one embodiment the ejector device is implemented as a two part device comprising an ejector assembly with fluid reservoir (also referred to herein as a cartridge) and a base system. The base system is configured to receive and engage with the cartridge in complementary fashion. When a user inserts the cartridge into the base system, electrical contact is made and the cartridge becomes active. In one embodiment, a cartridge EEPROM is read to start a countdown on disabling the cartridge.

A front rotary seal may be provided that covers the ejector mechanism of the cartridge, and is configured to be turned in order to open or provide line of sight access to the ejector holes of the ejector mechanism. The turning also triggers a magnetic switch in the cartridge which is relayed to a microcontroller unit to bring it out of sleep mode. A targeting system (blue LED) is also turned on and the boost converter started.

An auto-tuning or quality sweep (Q-sweep) is initiated to set the spray frequency. In this embodiment the Q-sweep involves the generation of three cycles of each of a range of frequencies within a predetermined frequency range and TEP feedback is obtained to find the optimal spray frequency regions. This is discussed in greater detail below. The initiation of the sweep may be triggered either by turning the front rotary seal or by activating a spray button, and in one embodiment the activation mechanism can be software selected. After the Q-sweep is complete, a boost converter configured to act as a charge pump raises the annulus (piezo ejector) voltage to a prescribed voltage for that product by charging up a boost rail to the desired voltage. The range can for instance be 0 to 120V.

A second switch is triggered when the user depresses the spray button. Upon this event, a gated complementary waveform generator (CWG) drives a level shifter circuit, which in turn drives a full bridge to drive the piezoelectric actuator and deliver the drug. The ejector mechanism ejects via either constant voltage drive (the boost duty cycle is constantly adjusted to balance the boost output voltage and thus the amplification in the resonant tank) or an overshoot drive, which is accomplished by charging the boost up and then turning the drive on causing massive overshoot for high velocity spray. While constant voltage can be used in either continuous or droplet on demand modes (ON for x cycles—OFF for y cycles—Repeat), overshoot can only be used with droplet on demand.

Further, the drive signal frequency can be constant frequency or dithered. Dithered means the frequency is swept (like a chirp) over a set bandwidth (3 k, 5 k, 10 k, 20 k). Dithering causes abrupt velocity changes in the piezoelectric movement resulting in better ejection. Dithering can for instance be performed quickly (within the decay time of the resonant tank) to generate a constant multi-tone signal.

An IR based volume detection circuit may be included to measure volume of liquid delivered during the spray and extends or contracts the spray time to deliver the correct dosing volume. After a predefined period of time (in this embodiment, after 10 seconds), all LED's are shut down and the device goes back into sleep mode until the user closes and reopens the front rotary seal.

Since the auto-tuning comprises one aspect of the present invention, a particular implementation will be described in more detail below.

The purpose of the auto-tuning system is to allow the piezoelectric ejector system to dynamically adjust itself to slight material differences and changing environmental variables and is critical to a reliable and manufacturable product.

The frequency generated by the numerically controlled oscillator (NCO) and CWG is incremented in set amounts over a defined range as high as 1 kHz to 200 kHz, but often 80-150 kHz in 1 kHz or 0.5 kHz increments. The battery voltage is compensated to take account of gradual depletion of the battery, whereafter the boost rail is charged to a constant voltage using analog-to-digital (ADC) sampling feedback. The tank (resonant structure defined by the capacitive piezoelectric actuator (piezo) and one or more inductors) is then driven for a brief period, preferably the minimum possible sample size, e.g., 1.5-2.5 periods at a single frequency. The drive signal is repeated 3-5 times in quick succession at this frequency in order to charge the capacitor in an integrating peak detector with the same amplitude coefficient (voltage) each time. The amplitude coefficient is recorded and the procedure repeated at the next frequency. This repetition of a low voltage signal significantly improves the signal to noise ratio of the measurement and prevents the system from ejecting while determining the optimum resonant frequencies to spray at.

Auto-tuning is achieved by driving the ejectors with a low voltage and measuring the piezo/inductor tank response (Q-factor.) When done across a broad frequency range this characterizes the ejector system and finds the peak frequency.

In order for the Q sweep to work properly the drive voltage needs to be high enough to properly drive energy into the piezoelectric, however, it must be low enough to not cause any unwanted ejection. Therefore the drive voltage has to be closely monitored by the microcontroller.

The Analog to Digital converter (ADC) used to monitor the drive voltage is mathematically compensated to maintain accurate measurement as the batteries de-rate and drop in voltage.

In this embodiment the sweep is software controlled by means of an algorithm that first checks the output range to ensure the proper voltage threshold has been met. The sweep will be a constant output without a high enough voltage for ejection of fluid, therefore if the output range is too low the voltage is increased slightly and the sweep is repeated.

The sweep is repeated in bursts looking for a consistent peak frequency across multiple measurements. If the peak is inconsistent the voltage is slightly increased and the burst is repeated. If two peaks remain equal the microcontroller will select the peak in the prior programmed optimal frequency range for ejection.

Figure 43:
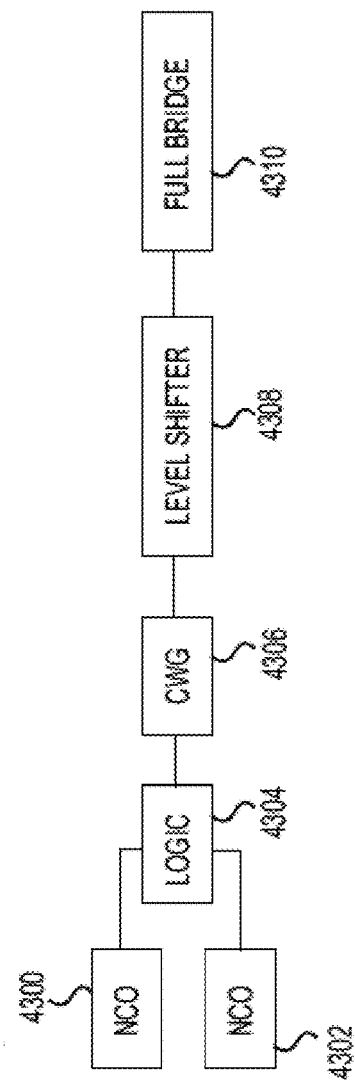
FIG. 43 is block diagram of one embodiment of a drive signal generator.

The components for generating the drive signal are depicted in the block diagram of FIG. 43, which shows a full bridge driver with integrated drive gating. A numerically controlled oscillator (NCO) 4300 creates the drive signal with high frequency resolution. A second numerically controlled oscillator 4302 is gated by means of logic 4304 with the first NCO in order to disable the complementary waveform generator (CWG) 4306 periodically without a huge software load on processor resources. This allows both extended FET life and relaxation of the ejector system at any frequency to combat spray "beading" issues as was discussed above. Timers could also be used to accomplish this. The logic combined signal is input into the complementary waveform generator 4306 which outputs two anti-phase square waves with adjustable dead bands to the level shifter circuit 4308, which translates 2.0V-3.5V to +35 for the PMOS (not shown) and +10 for the NMOS (not shown) of the full bridge 4310 to minimize switching losses and ON resistance. The CWG 4306 effectively alternates the number of "on" cycles driving the piezo with the number of "off" cycles to allow fluid relaxation.

Figure 44:
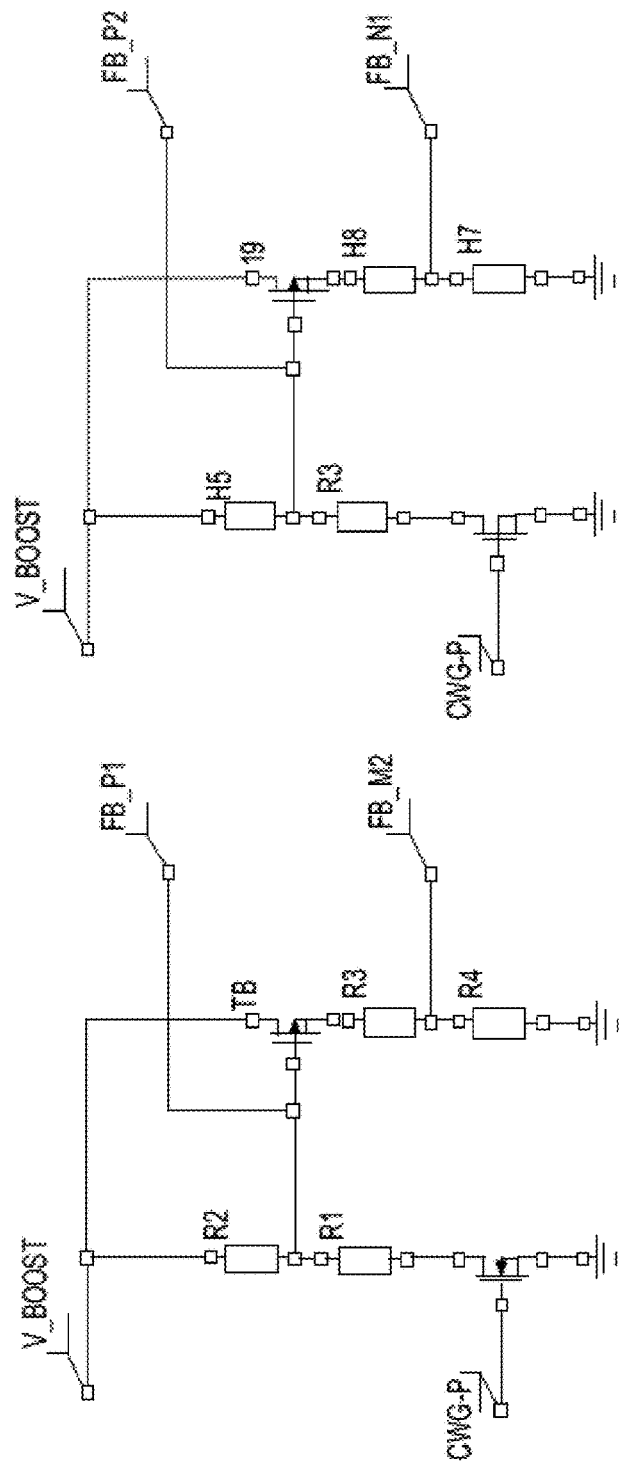
FIG. 44 is a schematic circuit diagram of one embodiment of a level shifter circuit.

A circuit diagram of one embodiment of a level shifter circuit 4308 for driving NMOS and PMOS is shown in FIG. 44.

It differentially drives the actuator using a 45V boost converter output (V_Boost) and is driven with anti-phase square waves from the CWG (CWG_P and CWG_N), which control the gates of FETs T1 and T10. The PMOS outputs (FB_P1 and FB_P2) are +45V to +35V, while the NMOS outputs (FB_N1 and FB_N2) are 0V to +10V.

As discussed above, the present embodiment also provides for infra-red (IR) spray volume detection. An IR LED is driven with up to 1.8V forward drop and a current of 65 mA. A phototransistor measures the light intensity and provides an analog output voltage between 0V and the battery voltage, which is read by the ADC. The spray has been shown to have a substantially linear voltage to spray volume response.

Figure 45:
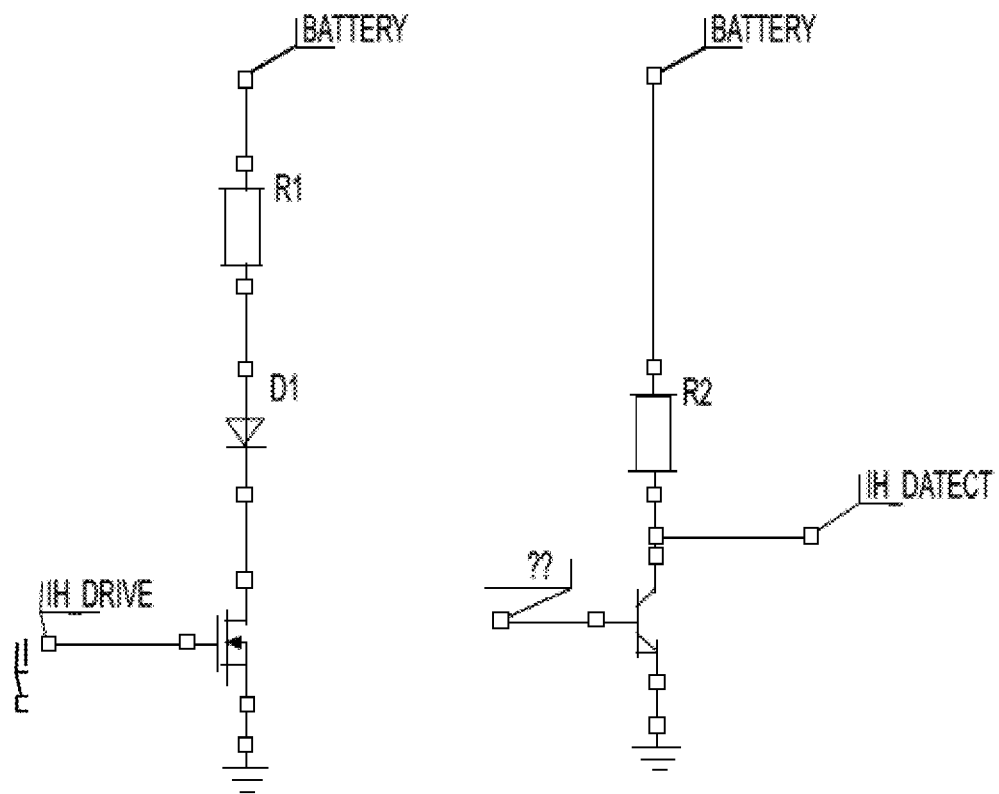
FIG. 45 is a schematic circuit diagram of one embodiment of an IR volume detection circuit.

One embodiment of such an IR spray volume detection circuit is shown in FIG. 45.

Figure 46:
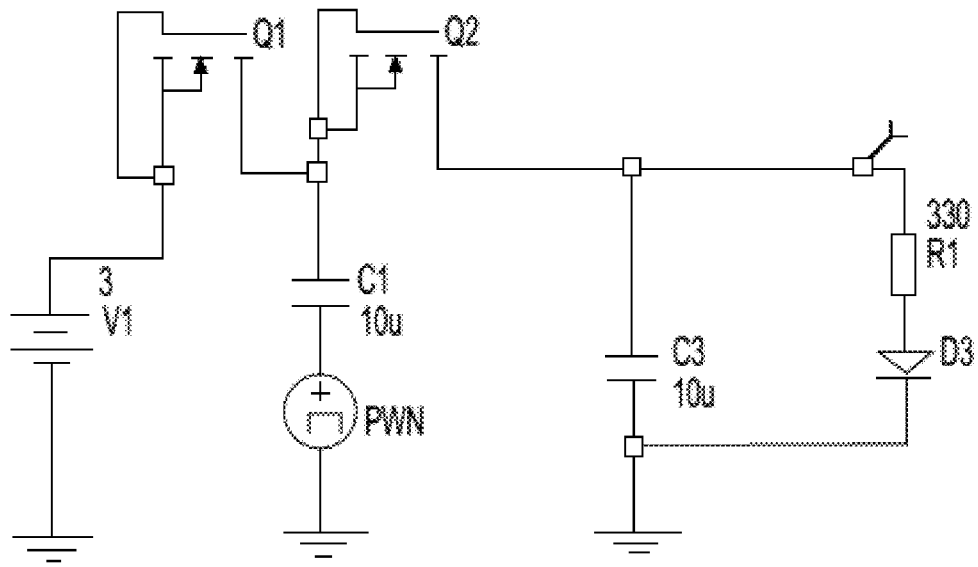
FIG. 46 is a schematic circuit diagram of one embodiment of a 2× charge pump.

In the present embodiment three batteries each providing approximately 1.5 V are used as the portable power source. In another embodiment only two batteries were used, necessitating the use of a 2× charge pump to raise the battery voltage sufficiently to drive the high luminosity targeting system LED. One embodiment of such a charge pump used a pulse width modulated signal from the microcontroller peripheral. A schematic circuit diagram of one embodiment of a charge pump circuit for a targeting LED is shown in FIG. 46.

As a further aspect of the present embodiment, the device provides a Drug Cartridge Enable/Disable/Timer. This is implemented in the present embodiment as a two wire serial interface EEPROM that is provided on the cartridge to allow unique identification, e.g., by means of a serial number. The serial number could be erased after a pre-defined usage period to permanently disable the cartridge. The serial number could be configured in different ways, e.g., the first few bits could be a manufacturer's identifier, while the remaining bits could provide a unique serial number for device to identify the drug in the reservoir. The microcontroller in this embodiment can keep track of up to 30 devices for up to 60 days.

The electronics, which could be implemented in an ASIC could be configured to receive input from a temperature sensor or the ASIC could have an internal temperature sensor for disabling cartridges if drug temperature exceeds a pre-defined temperature.

Figure 47:
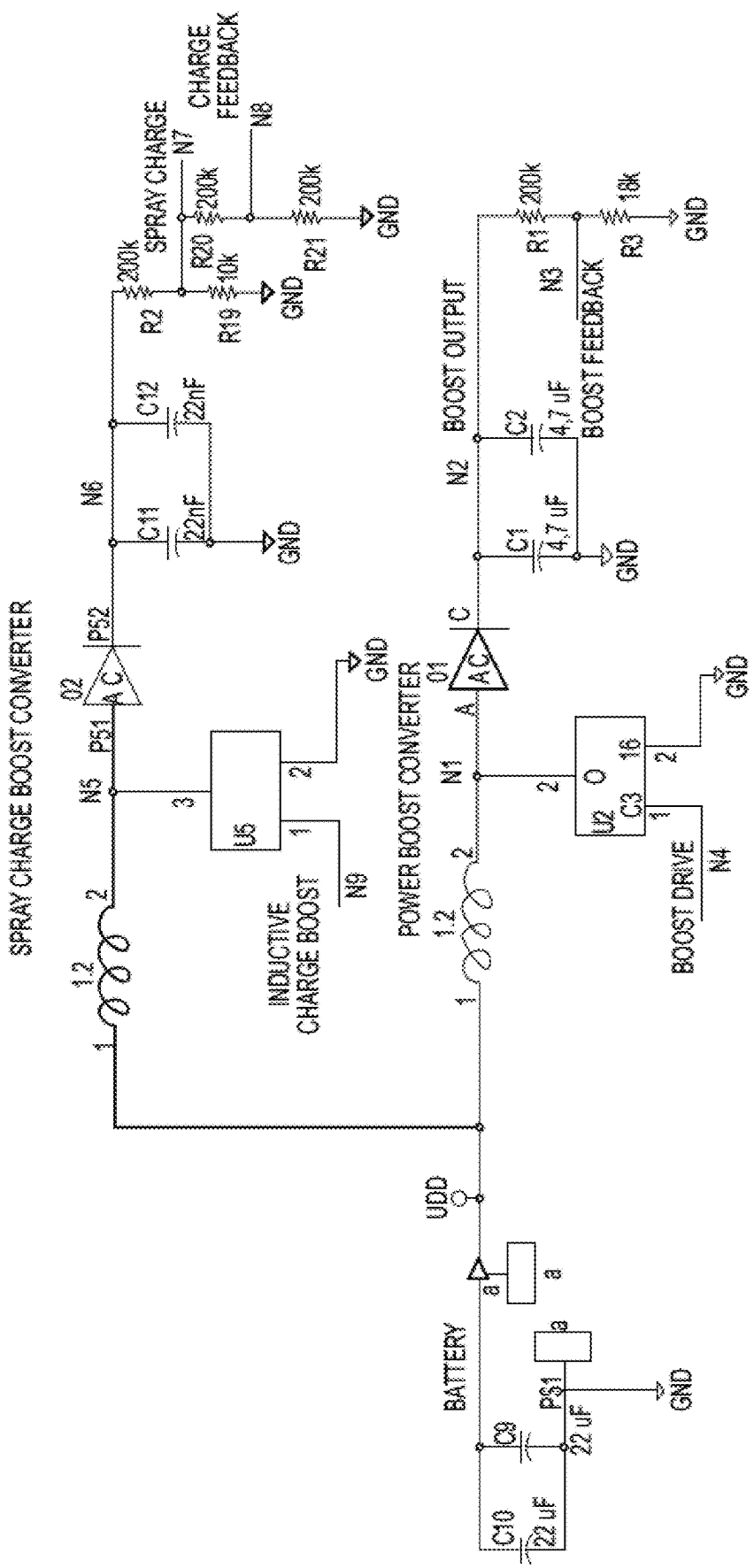
FIG. 47 is a schematic circuit diagram of one embodiment of two boost converters acting as a charge pump and piezo driver, according to the disclosure.

As discussed above, in order to provide the appropriate voltage to the actuator, a boost rail is charged to the desired voltage by making use of a boost converter configured to act as a charge pump. FIG. 47 is a circuit diagram of two boost converters—one that powers the piezo drive and another that provides a prescribed low current annulus charge (voltage).

Figure 48:
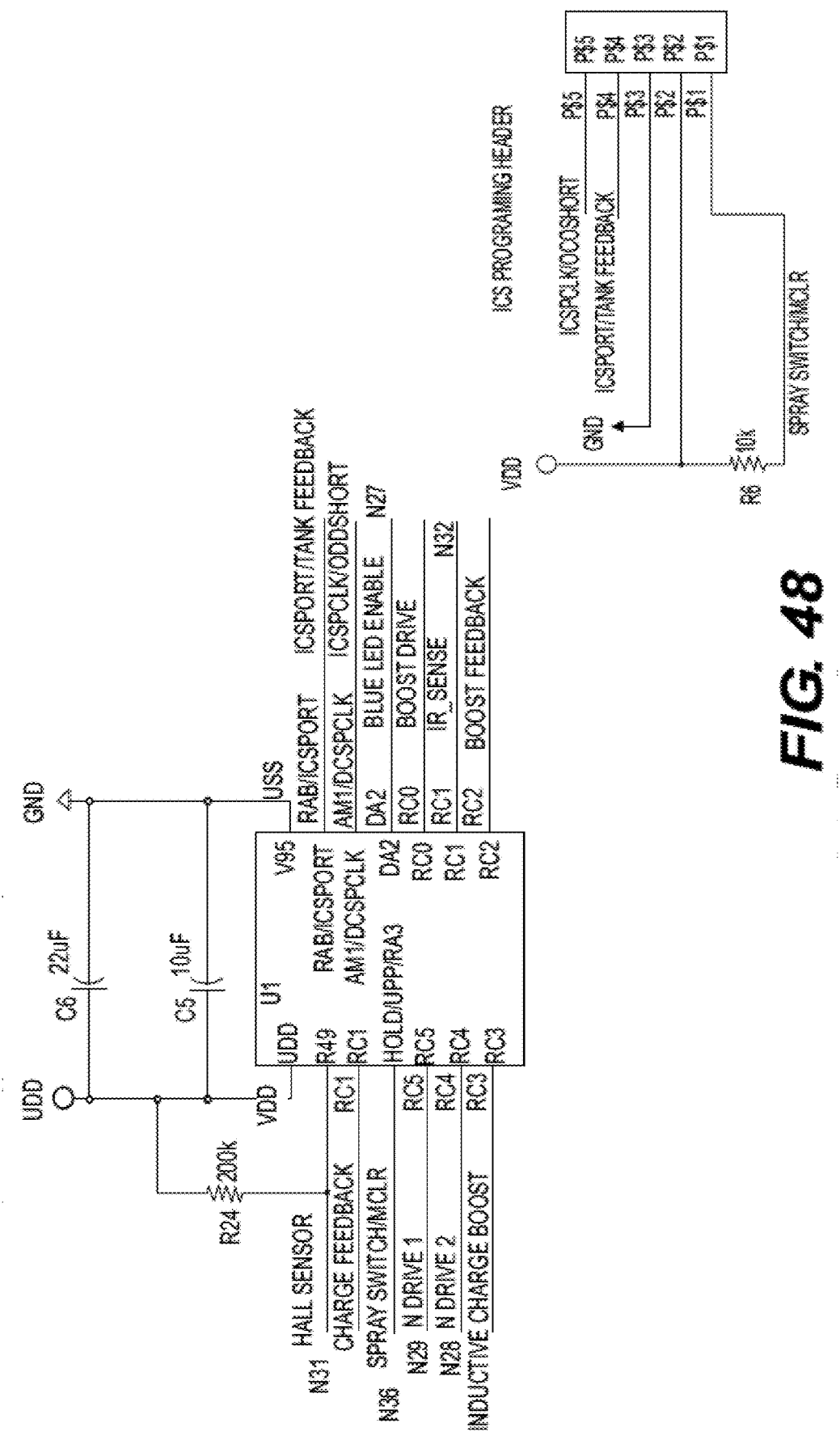
FIG. 48 is a schematic circuit diagram of one embodiment of a microcontroller of the disclosure.

The monitoring is performed by an ADC in conjunction with a microcontroller. FIG. 48 is a circuit diagram of one embodiment of a microcontroller. The ADC, NCO, CWG, PWM, are all internal to that part. The ADC in this embodiment is an integrated device and can be switched inside the chip between various pins. Initially it starts on pin RC2 where it is used to monitor and maintain voltage of boost during Q-sweep (auto-tuning). As discussed above, the voltage has to be nearly constant or the result of the frequency sweep will provide a wrong result. The ADC is then switched to RA4, which allows the actuator (annulus) voltage to be charged and calibrated. Last of all, the ADC is switched to RA0, where the integrating peak detector scales the peak voltage to the voltage range of the ADC. The measurement from the peak detector can be used to keep constant tank voltage or to grab amplitude coefficients from the Q-sweep.

Figure 49:
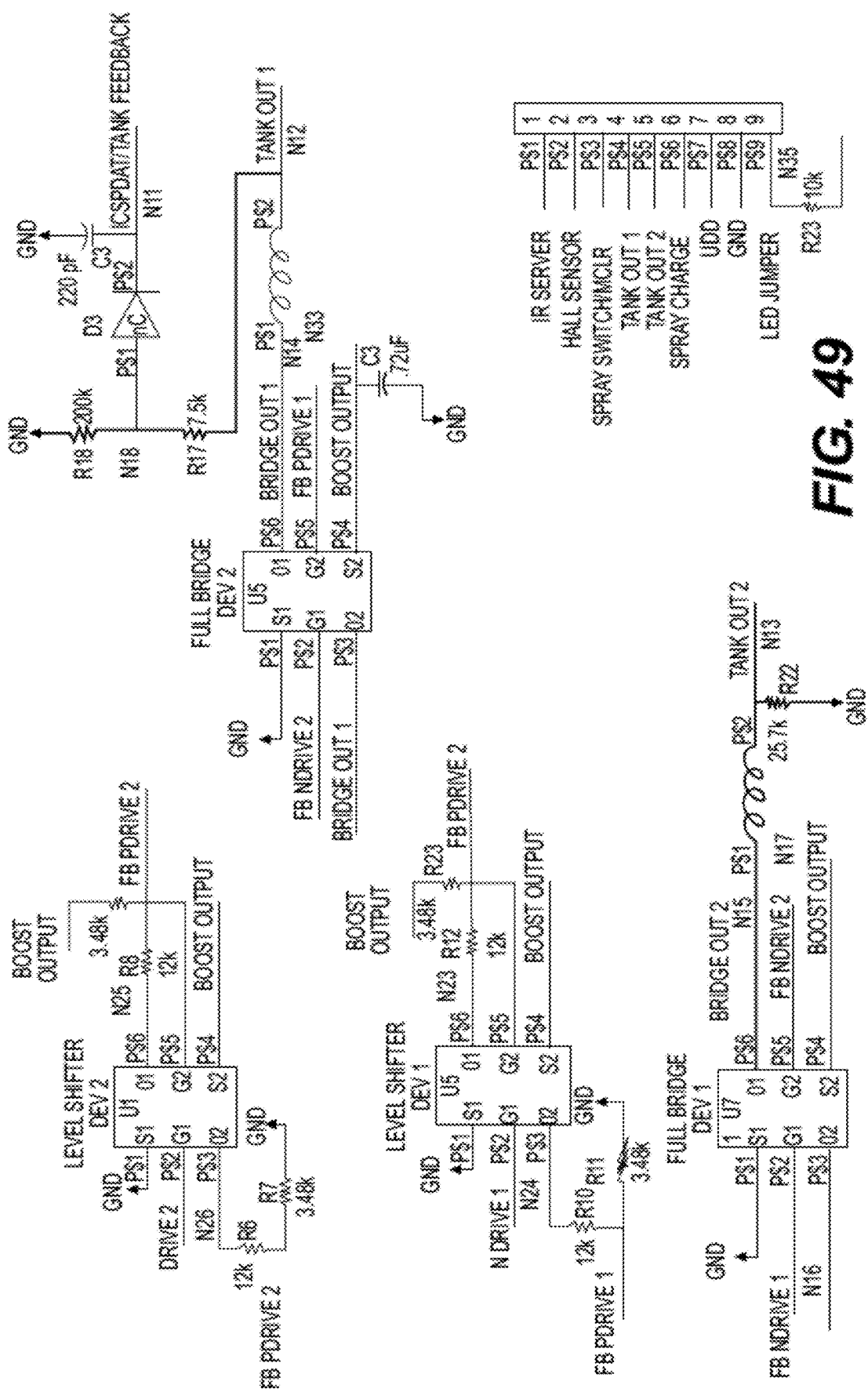
FIG. 49 shows a circuit diagram of one embodiment of a set of level shifters driving a full bridge loaded with a resonant tank (including piezo).

FIG. 49 shows a circuit diagram of one embodiment of a set of level shifters driving a full bridge loaded with a resonant tank (including piezo). It also has peak detector feedback.

Figure 50:
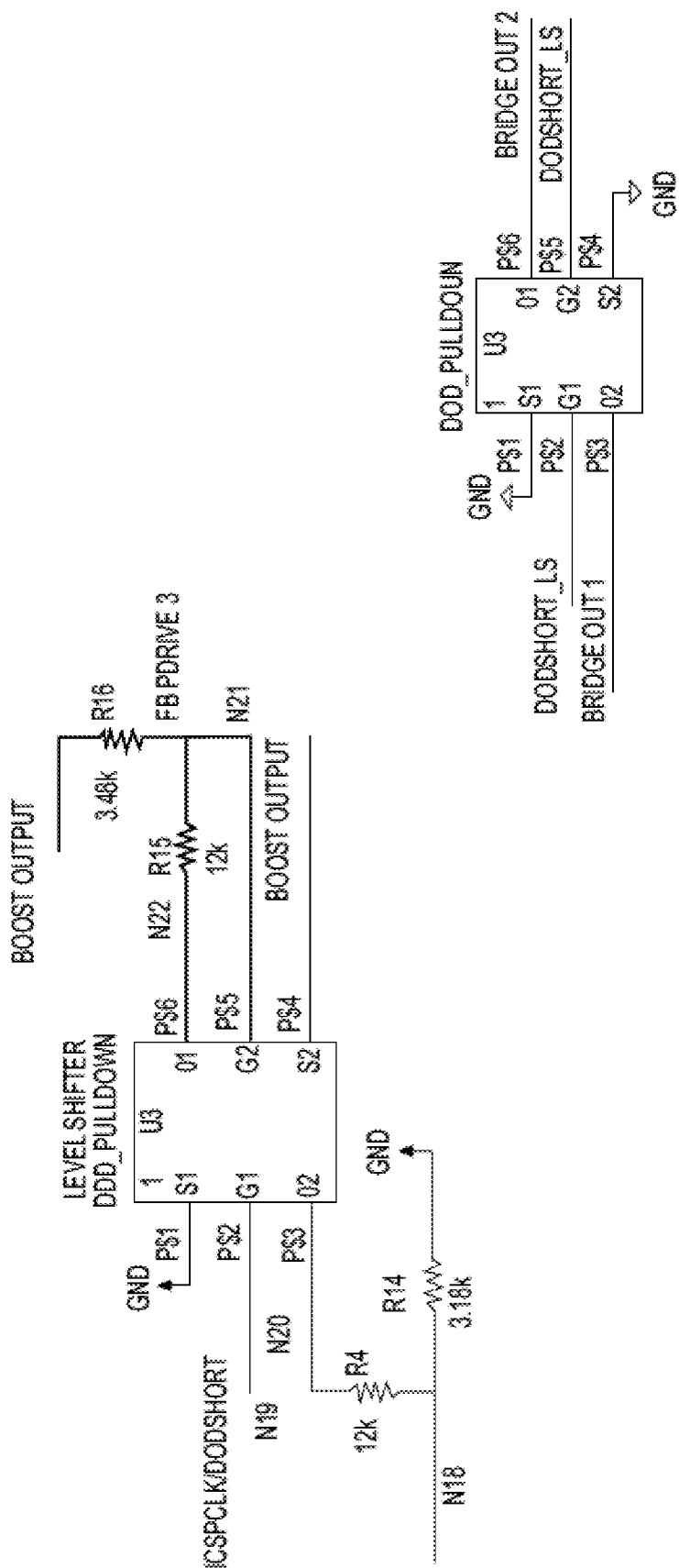
FIG. 50 shows one embodiment of a TEP pulldown/ droplet on demand pulldown circuit.

FIG. 50 shows one embodiment of a TEP pulldown/droplet on demand pulldown circuit composed of a level shifter and two NMOS FETS that drain the tank rather than letting it float when the full bridge stops driving.

While this invention has been described with reference to specific embodiments, it will be understood by those skilled in the art that various changes may be made and equivalents may be substituted for elements thereof, without departing from the spirit and scope of the invention. In addition, modifications may be made to adapt the teachings of the invention to particular situations and materials, without departing from the essential scope thereof. Thus, the invention is not limited to the particular examples that are disclosed herein, but encompasses all embodiments falling within the scope of the appended claims.

The invention claimed is:

1. A system comprising:
a droplet ejector assembly including a piezoelectric actuator coupled to a droplet generator plate having a plurality of openings therethrough, the droplet generator plate defining a fluid-filled droplet generator plate when the openings are filled with fluid;
a drive signal generator electrically coupled to the piezoelectric actuator, the drive signal generator being configured to generate a drive signal for driving the piezoelectric actuator, and
a controller electrically coupled to the actuator and the drive signal generator, wherein the controller is configured to control the drive signal to drive the piezoelectric actuator at a resonance frequency of the droplet generator assembly;
wherein the controller is configured to determine the resonance frequency based on a decay signal from the piezoelectric actuator; and
wherein the controller includes a capacitor and an ADC to determine a time-energy product (TEP) of the decay signal.

2. The system of claim 1, wherein the controller comprises a resonant measurement and control circuit configured to determine the resonance frequency of the droplet ejector assembly by controlling the drive signal generator to produce a set of frequency signals across a range of frequencies and monitoring the effect on the decay signal.

3. The system of claim 2, wherein the each frequency signal is repeated multiple times and a resultant time-energy product (TEP) signal is monitored each time to ensure consistency.

4. The system of claim 1, wherein the drive signal comprises at least two different frequency signals, the resonance frequency being defined by interference between the at least two different frequency signals.

5. The system of claim 4, wherein each of the different frequency signals is non-resonant with respect to the droplet ejector assembly.

6. A method of operating a droplet ejector assembly, the method comprising:
applying a drive signal to a droplet ejector assembly including a piezoelectric actuator coupled to a fluid-loaded droplet generator plate;
determining a resonance frequency of the ejector assembly based on accumulated magnitude or peak value of a feedback signal from the piezoelectric actuator, and
controlling the drive signal to drive the piezoelectric actuator at a resonance frequency of the ejector assembly;
wherein the feedback signal is defined by a decay signal following a drive or test signal to the actuator, wherein the controlling is performed by a controller coupled to the piezoelectric actuator, the controller comprising a capacitor and an ADC to determine a time-energy product (TEP) of the decay signal.

7. The method of claim 6, wherein the drive signal is adjusted to account for changes in the resonance frequency of the ejector assembly due to changes in one or more of an amount of fluid loading of the droplet generator plate, temperature, humidity, and pressure.

8. The method of claim 6, wherein applying the drive signal to the actuator comprises generating at least a first and a second different drive frequency signals that separately are non-resonant with respect to the fluid-loaded droplet generator plate, but together are resonant with respect to the fluid-loaded droplet generator plate.

* * * * *